(12) United States Patent
Rendler et al.

(10) Patent No.: US 11,440,910 B2
(45) Date of Patent: Sep. 13, 2022

(54) PESTICIDALLY ACTIVE HETEROCYCLIC DERIVATIVES WITH SULFUR CONTAINING SUBSTITUENTS

(71) Applicant: SYNGENTA PARTICIPATIONS AG, Rosentalstrasse (CH)

(72) Inventors: Sebastian Rendler, Stein (CH); Andrew Edmunds, Stein (CH); Pierre Joseph Marcel Jung, Stein (CH); Michel Muehlebach, Stein (CH); Girish Rawal, Ilhas Goa (IN); Indira Sen, Ilhas Goa (IN); Vikas Sikervar, Ilhas Goa (IN)

(73) Assignee: SYNGENTA PARTICIPATIONS AG, Basel (CH)

( * ) Notice: Subject to any disclaimer, the term of this patent is extended or adjusted under 35 U.S.C. 154(b) by 302 days.

(21) Appl. No.: 16/487,278

(22) PCT Filed: Feb. 16, 2018

(86) PCT No.: PCT/EP2018/053854
§ 371 (c)(1),
(2) Date: Aug. 20, 2019

(87) PCT Pub. No.: WO2018/153778
PCT Pub. Date: Aug. 30, 2018

(65) Prior Publication Data
US 2019/0367514 A1 Dec. 5, 2019

(30) Foreign Application Priority Data
Feb. 21, 2017 (IN) .............................. 201711006112

(51) Int. Cl.
*A01N 43/90* (2006.01)
*C07D 471/04* (2006.01)
*C07D 487/04* (2006.01)

(52) U.S. Cl.
CPC ........... *C07D 471/04* (2013.01); *A01N 43/90* (2013.01); *C07D 487/04* (2013.01)

(58) Field of Classification Search
None
See application file for complete search history.

(56) References Cited

U.S. PATENT DOCUMENTS 9,018,134 B2   4/2015   Takahashi et al.

FOREIGN PATENT DOCUMENTS

| RU | 2606119 C2 | 1/2017 |
| WO | 2016026848 A1 | 2/2016 |
| WO | 20160026848 A1 | 2/2016 |
| WO | 2016071214 A1 | 5/2016 |
| WO | 2016096584 A1 | 6/2016 |

OTHER PUBLICATIONS

DATABASE PubChem Compound [IOnline] NCBI; Apr. 9, 2016, XP002780100; Database accession No. CID 118892648, p. 3.
International Search Report of PCT/EP2018/053854 dated May 3, 2018.
Belikov V.G. Pharmaceutical Chemisty, Chapter 2.6: "Relationship between the chemical structure properties of substances their impact on an organism"; Moscow: MEDpress-inform; 2007, pp. 27-29.

*Primary Examiner* — Alton N Pryor
(74) *Attorney, Agent, or Firm* — Bakerhostetler; Toni-Junell Herbert

(57) ABSTRACT

Compounds of formula (I), wherein the substituents are as defined in claim 1, and the agrochemically acceptable salts salts, stereoisomers, enantiomers, tautomers and N-oxides of those compounds, can be used as insecticides and can be prepared in a manner known per se.

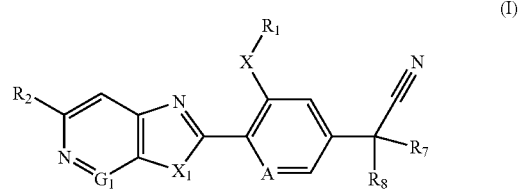

28 Claims, No Drawings

PESTICIDALLY ACTIVE HETEROCYCLIC DERIVATIVES WITH SULFUR CONTAINING SUBSTITUENTS

CROSS-REFERENCE TO RELATED APPLICATIONS

This application is a 371 National Stage application of International Application No. PCT/EP2018/053854, filed Feb. 16, 2018, which claims priority to Indian Application No. 201711006112 filed Feb. 21, 2017, the entire contents of which applications are hereby incorporated by reference.

The present invention relates to pesticidally active, in particular insecticidally active heterocyclic derivatives containing sulfur substituents, to intermediates for the preparation of those compounds, to compositions comprising those compounds, and to their use for controlling animal pests (including arthropods and in particular insects or representatives of the order Acarina).

Heterocyclic compounds with pesticidal action are known and described, for example, in WO 2012/086848, WO 2013/018928 and WO 2016/026848.

It has now surprisingly been found that certain novel pesticidally active heterocyclic 6/5-bicyclic ring derivatives with sulfur containing phenyl and pyridyl substituents have favourable properties as pesticides.

The present invention therefore provides compounds of formula I,

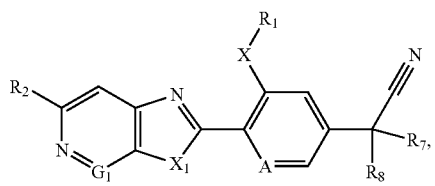

wherein
A is CH or N;
X is S, SO or $SO_2$;
$R_1$ is $C_1$-$C_4$alkyl, $C_1$-$C_4$haloalkyl or $C_3$-$C_6$cycloalkyl-$C_1$-$C_4$alkyl;
$G_1$ is N or CH;
$X_1$ is O, S or $NR_3$; wherein $R_3$ is hydrogen or $C_1$-$C_4$alkyl;
$R_2$ is halogen, $C_1$-$C_6$haloalkyl, $C_1$-$C_4$haloalkylsulfanyl, $C_1$-$C_4$haloalkylsulfinyl, $C_1$-$C_4$haloalkylsulfonyl or $C_1$-$C_6$haloalkoxy;
$R_7$ is hydrogen, halogen, cyano, $C_1$-$C_6$alkyl, $C_1$-$C_6$haloalkyl, $C_3$-$C_6$cycloalkyl, $C_1$-$C_4$alkoxy, $C_1$-$C_4$alkoxy$C_1$-$C_4$alkyl, $C_1$-$C_4$alkylsulfanyl, $C_1$-$C_4$alkylsulfanyl-$C_1$-$C_4$alkyl, $C_1$-$C_4$alkylsulfinyl-$C_1$-$C_4$alkyl, $C_1$-$C_4$alkylsulfonyl-$C_1$-$C_4$alkyl or $C_1$-$C_4$alkyloxycarbonyl; and
$R_8$ is halogen, cyano, $C_1$-$C_6$alkyl, $C_1$-$C_6$haloalkyl, $C_3$-$C_6$cycloalkyl, $C_1$-$C_4$alkoxy, $C_1$-$C_4$alkoxy-$C_1$-$C_4$alkyl, $C_1$-$C_4$alkylsulfanyl, $C_1$-$C_4$alkylsulfanyl-$C_1$-$C_4$alkyl, $C_1$-$C_4$alkylsulfinyl-$C_1$-$C_4$alkyl, $C_1$-$C_4$alkylsulfonyl-$C_1$-$C_4$alkyl or $C_1$-$C_4$alkyloxycarbonyl; and agrochemically acceptable salts, stereoisomers, enantiomers, tautomers and N-oxides of the compounds of formula I.

Compounds of formula I which have at least one basic centre can form, for example, acid addition salts, for example with strong inorganic acids such as mineral acids, for example perchloric acid, sulfuric acid, nitric acid, nitrous acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds of formula I which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

The alkyl groups occurring in the definitions of the substituents can be straight-chain or branched and are, for example, methyl, ethyl, n-propyl, isopropyl, n-butyl, sec-butyl, iso-butyl, tert-butyl, pentyl, hexyl, nonyl, decyl and their branched isomers. Alkylsulfanyl, alkylsulfinyl, alkylsulfonyl, alkoxy, alkenyl and alkynyl radicals are derived from the alkyl radicals mentioned. The alkenyl and alkynyl groups can be mono- or polyunsaturated.

Halogen is generally fluorine, chlorine, bromine or iodine. This also applies, correspondingly, to halogen in combination with other meanings, such as haloalkyl or halophenyl.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl.

Alkoxy groups preferably have a preferred chain length of from 1 to 6 carbon atoms. Alkoxy is, for example, methoxy, ethoxy, propoxy, i-propoxy, n-butoxy, isobutoxy, sec-butoxy and tert-butoxy and also the isomeric pentyloxy and hexyloxy radicals.

Alkoxyalkyl groups preferably have a chain length of 1 to 6 carbon atoms. Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

The cycloalkyl groups preferably have from 3 to 6 ring carbon atoms, for example cyclopropyl, cyclobutyl, cyclopentyl and cyclohexyl.

Free radicals represent methyl groups.

The compounds of formula I according to the invention also include hydrates which may be formed during the salt formation.

Preferred values of $R_1$, $R_2$, X, $R_7$, $R_8$, A, $G_1$ and $X_1$, are, in any combination thereof, as set out below:

Preferably $R_1$ is $C_1$-$C_4$alkyl or $C_3$-$C_6$cycloalkyl-$C_1$-$C_4$alkyl.

More preferably $R_1$ is $C_1$-$C_4$alkyl or cyclopropylmethyl.

Even more preferably $R_1$ is methyl, ethyl, n-propyl, i-propyl or cyclopropylmethyl.

Most preferably $R_1$ is ethyl.

Preferably $R_2$ is halogen, $C_1$-$C_4$haloalkyl, $C_1$-$C_4$haloalkylsulfanyl, $C_1$-$C_4$haloalkylsulfinyl or $C_1$-$C_4$haloalkylsulfonyl.

More preferably $R_2$ is halogen or $C_1$-$C_3$haloalkyl.

Even more preferably $R_2$ is $C_1$-$C_2$haloalkyl.
Most preferably $R_2$ is trifluoromethyl.
Preferably X is S or $SO_2$.
Most preferably X is $SO_2$.
Preferably $R_7$ is hydrogen, fluoro, cyano, $C_1$-$C_4$alkoxycarbonyl, $C_1$-$C_4$alkyl.
More preferably $R_7$ is hydrogen methyl, ethyl or fluoro.
Even more preferably $R_7$ is methyl or fluoro.
Most preferably $R_7$ is methyl.
Preferably $R_8$ is cyano, fluoro or $C_1$-$C_4$alkyl.
More preferably $R_8$ is fluoro, methyl or ethyl.
Even more preferably $R_8$ is fluoro or methyl.
Most preferably $R_8$ is methyl.
Preferably A is N.
Preferably $G_1$ is N.
Preferably $X_1$ is $NR_3$, wherein $R_3$ is $C_1$-$C_4$alkyl.
Most preferably $X_1$ is $NCH_3$.
Embodiments according to the invention are provided as set out below.

Embodiment 1 provides compounds of formula I, or an agrochemically acceptable salt, stereoisomer, enantiomer, tautomer or N-oxide thereof, as defined above.

Embodiment 2 provides compounds, or an agrochemically acceptable salt, stereoisomer, enantiomer, tautomer or N-oxide thereof, according to embodiment 1 wherein $R_1$ is $C_1$-$C_4$alkyl or $C_3$-$C_6$cycloalkyl-$C_1$-$C_4$alkyl.

Embodiment 3 provides compounds, or an agrochemically acceptable salt, stereoisomer, enantiomer, tautomer or N-oxide thereof, according to embodiment 1 or 2 wherein $R_2$ is halogen, $C_1$-$C_4$haloalkyl, $C_1$-$C_4$haloalkylsulfanyl, $C_1$-$C_4$haloalkylsulfinyl or $C_1$-$C_4$haloalkylsulfonyl.

Embodiment 4 provides compounds, or an agrochemically acceptable salt, stereoisomer, enantiomer, tautomer or N-oxide thereof, according to any one of embodiments 1, 2 or 3 wherein X is S or $SO_2$.

Embodiment 5 provides compounds, or an agrochemically acceptable salt, stereoisomer, enantiomer, tautomer or N-oxide thereof, according to any one of embodiments 1, 2, 3 or 4 wherein $R_7$ is hydrogen, fluoro, cyano, $C_1$-$C_4$alkoxycarbonyl, $C_1$-$C_4$alkyl.

Embodiment 6 provides compounds, or an agrochemically acceptable salt, stereoisomer, enantiomer, tautomer or N-oxide thereof, according to any one of embodiments 1, 2, 3, 4 or 5 wherein $R_8$ is cyano, fluoro or $C_1$-$C_4$alkyl.

Embodiment 7 provides compounds, or an agrochemically acceptable salt, stereoisomer, enantiomer, tautomer or N-oxide thereof, according to any one of embodiments 1, 2, 3, 4, 5 or 6 wherein $X_1$ is $NR_3$, wherein $R_3$ is $C_1$-$C_4$alkyl.

Embodiment 8 provides compounds, or an agrochemically acceptable salt, stereoisomer, enantiomer, tautomer or N-oxide thereof, according to any one of embodiments 1, 2, 3, 4, 5, 6 or 7 wherein $R_1$ is $C_1$-$C_4$alkyl or cyclopropylmethyl.

Embodiment 9 provides compounds, or an agrochemically acceptable salt, stereoisomer, enantiomer, tautomer or N-oxide thereof, according to any one of embodiments 1, 2, 3, 4, 5, 6, 7 or 8 wherein $R_2$ is halogen or $C_1$-$C_6$haloalkyl.

Embodiment 10 provides compounds, or an agrochemically acceptable salt, stereoisomer, enantiomer, tautomer or N-oxide thereof, according to any one of embodiments 1, 2, 3, 4, 5, 6, 7, 8 or 9 wherein $R_7$ is hydrogen methyl, ethyl or fluoro.

Embodiment 11 provides compounds, or an agrochemically acceptable salt, stereoisomer, enantiomer, tautomer or N-oxide thereof, according to any one of embodiments 1, 2, 3, 4, 5, 6, 7, 8, 9 or 10 wherein $R_8$ is fluoro, methyl or ethyl.

Embodiment 12 provides compounds, or an agrochemically acceptable salt, stereoisomer, enantiomer, tautomer or N-oxide thereof, according to any one of embodiments 1, 2, 3, 4, 5, 6, 7, 8, 9, 10 or 11 wherein $X_1$ is $NCH_3$.

Embodiment 13 provides compounds, or an agrochemically acceptable salt, stereoisomer, enantiomer, tautomer or N-oxide thereof, according to any one of embodiments 1, 2, 3, 4, 5, 6, 7, 8, 9, 10, 11 or 12 wherein $R_1$ is methyl, ethyl, n-propyl, i-propyl or cyclopropylmethyl.

Embodiment 14 provides compounds, or an agrochemically acceptable salt, stereoisomer, enantiomer, tautomer or N-oxide thereof, according to any one of embodiments 1, 2, 3, 4, 5, 6, 7, 8, 9, 10, 11, 12 or 13 wherein $R_2$ is $C_1$-$C_2$haloalkyl.

Embodiment 15 provides compounds, or an agrochemically acceptable salt, stereoisomer, enantiomer, tautomer or N-oxide thereof, according to any one of embodiments 1, 2, 3, 4, 5, 6, 7, 8, 9, 10, 11, 12, 13 or 14 wherein X is $SO_2$.

Embodiment 16 provides compounds, or an agrochemically acceptable salt, stereoisomer, enantiomer, tautomer or N-oxide thereof, according to any one of embodiments 1, 2, 3, 4, 5, 6, 7, 8, 9, 10, 11, 12, 13, 14 or 15 wherein $R_7$ is methyl or fluoro.

Embodiment 17 provides compounds, or an agrochemically acceptable salt, stereoisomer, enantiomer, tautomer or N-oxide thereof, according to any one of embodiments 1, 2, 3, 4, 5, 6, 7, 8, 9, 10, 11, 12, 13, 14, 15 or 16 wherein $R_8$ is fluoro or methyl.

Embodiment 18 provides compounds, or an agrochemically acceptable salt, stereoisomer, enantiomer, tautomer or N-oxide thereof, according to any one of embodiments 1, 2, 3, 4, 5, 6, 7, 8, 9, 10, 11, 12, 13, 14, 15, 16 or 17 wherein $R_1$ is ethyl.

Embodiment 19 provides compounds, or an agrochemically acceptable salt, stereoisomer, enantiomer, tautomer or N-oxide thereof, according to any one of embodiments 1, 2, 3, 4, 5, 6, 7, 8, 9, 10, 11, 12, 13, 14, 15, 16, 17 or 18 wherein $R_2$ is trifluoromethyl.

Embodiment 20 provides compounds, or an agrochemically acceptable salt, stereoisomer, enantiomer, tautomer or N-oxide thereof, according to any one of embodiments 1, 2, 3, 4, 5, 6, 7, 8, 9, 10, 11, 12, 13, 14, 15, 16, 17, 18 or 19 wherein $R_7$ is methyl.

Embodiment 21 provides compounds, or an agrochemically acceptable salt, stereoisomer, enantiomer, tautomer or N-oxide thereof, according to any one of embodiments 1, 2, 3, 4, 5, 6, 7, 8, 9, 10, 11, 12, 13, 14, 15, 16, 17, 18, 19 or 20 wherein $R_8$ is methyl.

Embodiment 22 provides compounds, or an agrochemically acceptable salt, stereoisomer, enantiomer, tautomer or N-oxide thereof, according to any one of embodiments 1, 2, 3, 4, 5, 6, 7, 8, 9, 10, 11, 12, 13, 14, 15, 16, 17, 18, 19, 20 or 21 wherein A is CH.

Embodiment 23 provides compounds, or an agrochemically acceptable salt, stereoisomer, enantiomer, tautomer or N-oxide thereof, according to any one of embodiments 1, 2, 3, 4, 5, 6, 7, 8, 9, 10, 11, 12, 13, 14, 15, 16, 17, 18, 19, 20 or 21 wherein A is N.

Embodiment 24 provides compounds, or an agrochemically acceptable salt, stereoisomer, enantiomer, tautomer or N-oxide thereof, according to any one of embodiments 1, 2, 3, 4, 5, 6, 7, 8, 9, 10, 11, 12, 13, 14, 15, 16, 17, 18, 19, 20, 21, 22 or 23 wherein $G_1$ is N.

Embodiment 25 provides compounds, or an agrochemically acceptable salt, stereoisomer, enantiomer, tautomer or N-oxide thereof, according to any one of embodiments 1, 2, 3, 4, 5, 6, 7, 8, 9, 10, 11, 12, 13, 14, 15, 16, 17, 18, 19, 20, 21, 22 or 23 wherein $G_1$ is CH.

One group of compounds of formula I is represented by the compounds of formula I-1

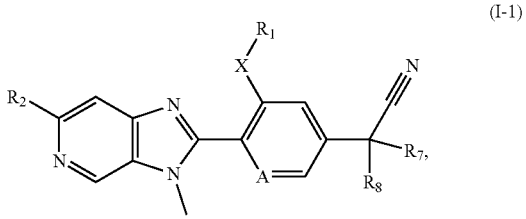
(I-1)

wherein A, X, $R_1$, $R_2$, $R_7$, and $R_8$ are as defined under formula I above. In said preferred group of compounds of formula I-1, $R_1$ is preferably methyl, ethyl, n-propyl, i-propyl or cyclopropylmethyl;

$R_2$ is preferably $C_1$-$C_4$haloalkyl, $C_1$-$C_4$haloalkylsulfanyl, $C_1$-$C_4$haloalkylsulfinyl or $C_1$-$C_4$haloalkylsulfonyl;

and X is preferably $SO_2$.

Especially preferred compounds of formula I-1 are those, wherein $R_1$ is ethyl and X is $SO_2$.

One group of compounds of formula I-1 is represented by the compounds of formula I-1a

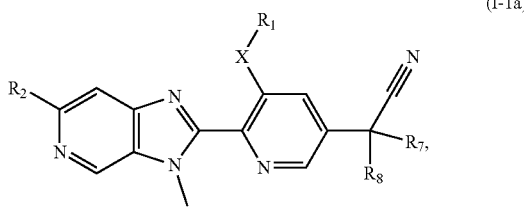
(I-1a)

wherein X, $R_1$, $R_2$, $R_7$, and $R_8$ are as defined under formula I above. In said preferred group of compounds of formula I-1, $R_1$ is preferably methyl, ethyl, n-propyl, i-propyl or cyclopropylmethyl;

$R_2$ is preferably $C_1$-$C_4$haloalkyl, $C_1$-$C_4$haloalkylsulfanyl, $C_1$-$C_4$haloalkylsulfinyl or $C_1$-$C_4$haloalkylsulfonyl;

and X is preferably $SO_2$.

Especially preferred compounds of formula I-1a are those, wherein $R_1$ is ethyl and X is $SO_2$.

Another group of compounds of formula I-1 is represented by the compounds of formula I-1b

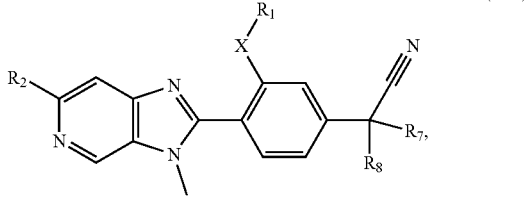
(I-1b)

wherein X, $R_1$, $R_2$, $R_7$, and $R_8$ are as defined under formula I above. In said preferred group of compounds of formula I-1, $R_1$ is preferably methyl, ethyl, n-propyl, i-propyl or cyclopropylmethyl;

$R_2$ is preferably $C_1$-$C_4$haloalkyl, $C_1$-$C_4$haloalkylsulfanyl, $C_1$-$C_4$haloalkylsulfinyl or $C_1$-$C_4$haloalkylsulfonyl;

and X is preferably $SO_2$.

Especially preferred compounds of formula I-1b are those, wherein $R_1$ is ethyl and X is $SO_2$.

Another group of compounds of formula I is represented by the compounds of formula I-2

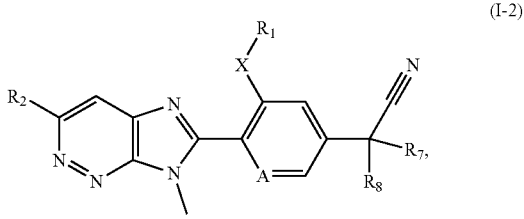
(I-2)

wherein A, X, $R_1$, $R_2$, $R_7$, and $R_8$ are as defined under formula I above. In said preferred group of compounds of formula I-1, $R_1$ is preferably methyl, ethyl, n-propyl, i-propyl or cyclopropylmethyl;

$R_2$ is preferably $C_1$-$C_4$haloalkyl, $C_1$-$C_4$haloalkylsulfanyl, $C_1$-$C_4$haloalkylsulfinyl or $C_1$-$C_4$haloalkylsulfonyl;

and X is preferably $SO_2$.

Especially preferred compounds of formula I-2 are those, wherein $R_1$ is ethyl and X is $SO_2$.

One group of compounds of formula I-2 is represented by the compounds of formula I-2a

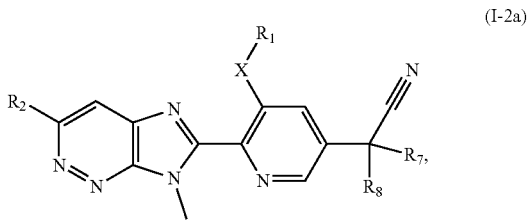
(I-2a)

wherein X, $R_1$, $R_2$, $R_7$, and $R_8$ are as defined under formula I above. In said preferred group of compounds of formula I-1, $R_1$ is preferably methyl, ethyl, n-propyl, i-propyl or cyclopropylmethyl;

$R_2$ is preferably $C_1$-$C_4$haloalkyl, $C_1$-$C_4$haloalkylsulfanyl, $C_1$-$C_4$haloalkylsulfinyl or $C_1$-$C_4$haloalkylsulfonyl;

and X is preferably $SO_2$.

Especially preferred compounds of formula I-2a are those, wherein $R_1$ is ethyl and X is $SO_2$.

Another group of compounds of formula I-2 is represented by the compounds of formula I-2b

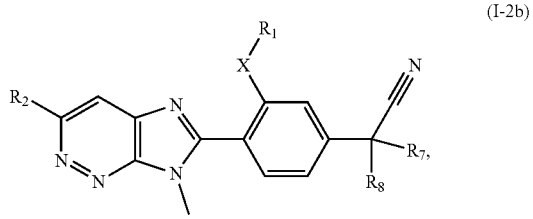

(I-2b)

wherein X, $R_1$, $R_2$, $R_7$, and $R_8$ are as defined under formula I above. In said preferred group of compounds of formula I-1, $R_1$ is preferably methyl, ethyl, n-propyl, i-propyl or cyclopropylmethyl;

$R_2$ is preferably $C_1$-$C_4$haloalkyl, $C_1$-$C_4$haloalkylsulfanyl, $C_1$-$C_4$haloalkylsulfinyl or $C_1$-$C_4$haloalkylsulfonyl;

and X is preferably $SO_2$.

Especially preferred compounds of formula I-2b are those, wherein $R_1$ is ethyl and X is $SO_2$.

Compounds according to the invention may possess any number of benefits including, inter alia, advantageous levels of biological activity for protecting plants against insects or superior properties for use as agrochemical active ingredients (for example, greater biological activity, an advantageous spectrum of activity, an increased safety profile, improved physico-chemical properties, or increased biodegradability). In particular, it has been surprisingly found that certain compounds of formula (I) may show an advantageous safety profile with respect to non-target arthropods, in particular pollinators such as honey bees, solitary bees, and bumble bees. Most particularly, Apis mellifera.

In another aspect the present invention provides a composition comprising an insecticidally, acaricidally, nematicidally or molluscicidally effective amount of a compound of formula (I), or an agrochemically acceptable salt, stereoisomer, enantiomer, tautomer or N-oxide thereof, as defined in any of embodiments 1, 2, 3, 4, 5, 6, 7, 8, 9, 10, 11, 12, 13, 14, 15, 16, 17, 18, 19, 20, 21, 22, 23, 24 or 25 (above) or any of the embodiments under compounds of formula (I-1), (I-1a), (I-1b), (I-2), (I-2a) and (I-2b) (above), and, optionally, an auxiliary or diluent.

In a further aspect the present invention provides a method of combating and controlling insects, acarines, nematodes or molluscs which comprises applying to a pest, to a locus of a pest, or to a plant susceptible to attack by a pest an insecticidally, acaricidally, nematicidally or molluscicidally effective amount of a compound of formula (I), or an agrochemically acceptable salt, stereoisomer, enantiomer, tautomer or N-oxide thereof, as defined in any of embodiments 1, 2, 3, 4, 5, 6, 7, 8, 9, 10, 11, 12, 13, 14, 15, 16, 17, 18, 19, 20, 21, 22, 23, 24 or 25 (above) or any of the embodiments under compounds of formula (I-1), (I-1a), (I-1b), (I-2), (I-2a) and (I-2b) (above) or a composition as defined above.

In a yet further aspect the present invention provides a method for the protection of plant propagation material from the attack by insects, acarines, nematodes or molluscs, which comprises treating the propagation material or the site, where the propagation material is planted, with a composition as defined above.

The process according to the invention for preparing compounds of formula I is carried out by methods known to those skilled in the art. Compounds of formula I-a3, wherein X is $SO_2$ and A, $X_1$, $G_1$, $R_1$, $R_2$, $R_7$, and $R_8$ are defined as under formula I above, may be prepared by oxidation of compounds of formula I-a2, wherein X is SO and A, $X_1$, $G_1$, $R_1$, $R_2$, $R_7$, and $R_8$ are defined as under formula I above. The reaction can be performed with reagents such as a peracid, for example peracetic acid or m-chloroperbenzoic acid, or a hydroperoxide, as for example, hydrogen peroxide or tert-butylhydroperoxide, or an inorganic oxidant, such as a monoperoxo-disulfate salt or potassium permanganate. In a similar way, compounds of formula I-a2, wherein X is SO and A, $X_1$, $G_1$, $R_1$, $R_2$, $R_7$, and $R_8$ are defined as under formula I above, may be prepared by oxidation of compounds of formula I-a1, wherein X is S and A, $X_1$, $G_1$, $R_1$, $R_2$, $R_7$, and $R_8$ are defined as under formula I above, under analogous conditions described above. These reactions can be performed in various organic or aqueous solvents compatible to these conditions, by temperatures from below 0° C. up to the boiling point of the solvent system. The transformation of compounds of the formula I-a1 into compounds of the formula I-a2 and I-a3 is represented in Scheme 1.

Scheme 1

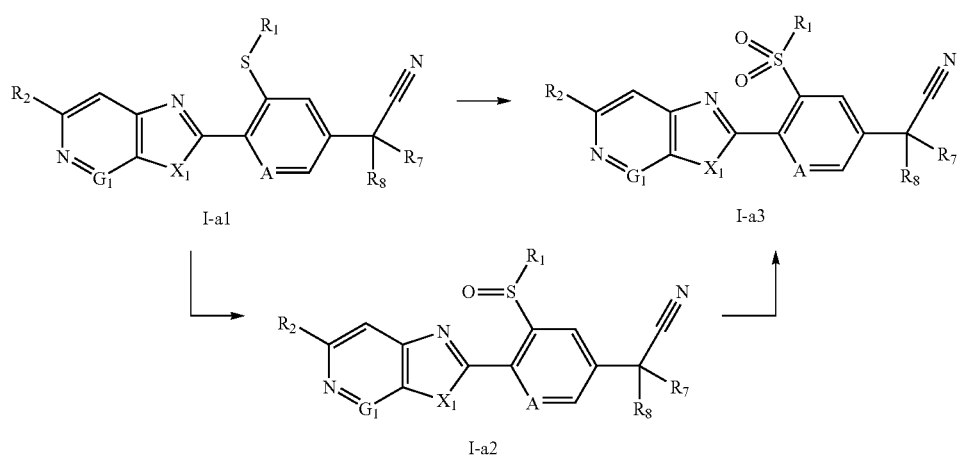

Compounds of formula I, wherein Q is defined as the radical shown at the bottom of the Scheme 2, and wherein X, A, $X_1$, $G_1$, $R_1$, $R_2$, $R_7$, and $R_8$ are defined as under formula I above, may be obtained by methods described in Scheme 2. Treatment of compounds of formula III, wherein Q, and A and $R_1$ are defined as under formula I above, X is S or $SO_2$, and $Xb_1$ is preferably halogen (even more preferably chlorine, bromine or iodine), with a compound of formula V (trimethylsilyl-acetonitrile), in the presence of zinc(II)fluoride, and a palladium(0) catalyst such as tris(dibenzylideneacetone)dipalladium(0)-chloroform adduct ($Pd_2(dba)_3$), a ligand, for example Xantphos, in an inert solvent, such as DMF at temperatures between 100-160° C., optionally under microwave heating, leads to compounds of formula II, wherein A, Q, and $R_1$ are defined as under general formula I above and X is S or $SO_2$. Such methods have been described in the literature, for example, *J. Am. Chem. Soc.* 2005, 127, 15824-15832. Compounds of formula II can be treated sequentially with alkylating reagents of general formula VIa and VIb wherein $Xb_2$ is preferably Br, I, $OSO_3Me$ or OTf, and $R_7$ are $R_8$ are defined under formula I, in the presence of a base, such as sodium hydride, $K_2CO_3$, or $Cs_2CO_3$, in an inert solvent such as THF, DMF, 1,4-dioxane or acetonitrile, to give compounds of formula I.

Alternatively, compounds of formula II can be subjected to an excess of the abovementioned base and reagent VIb to obtain compounds of general type Ia-4, wherein $R_7=R_8$. Alternatively, compounds of formula II can be obtained from compounds of formula VII, wherein A, Q, X, and $R_1$ are defined as under formula I above, and $R_{11}$ stands for a $C_1$-$C_6$alkyl group, preferably methyl or ethyl, by Krapcho decarboxylation. Such methods have been described, for example in, *Tetradehron Lett.* 1974, 15, 1091-1094. Compounds of formula VII may be obtained by reaction of compounds of formula III with cyanoacetates of general formula VIII, wherein $R_{11}$ stands for a $C_1$-$C_6$alkyl group, preferably methyl or ethyl. This reaction may proceed in polar aprotic solvents such as dimethylsulfoxide (DMSO), N,N-dimethylformamide (DMF), or N-methylpyrrolidone (NMP), in the presence of a base, such as $K_2CO_3$ or $Na_2CO_3$, in the presence of absence of a phase-transfer catalyst ("PTC") at temperatures between 20-180° C., preferably 80-140° C. Similarly, transition metal-catalyzed processes are known, see for example, *Angew. Chem. Int. Ed.* 2011, 50, 4470-4474. Alternatively, compounds of formula I can be prepared directly from compounds of formula III by treatment with compounds of formula IV, wherein $R_7$ and $R_8$ are defined as above for formula I, in the presence or absence of a catalyst such as $Pd_2(dba)_3$, and a ligand, such as BINAP, using a strong base such as LiHMDS, in an inert solvent such as THF at temperatures between −20 and 120° C. Such methods have been described in the literature, for example, *Org. Lett.* 2014, 16, 6314-6317; *J. Org. Chem.* 2005, 70, 10186-10189 or *Org. Lett.* 2011, 13, 1690-1693.

Scheme 2

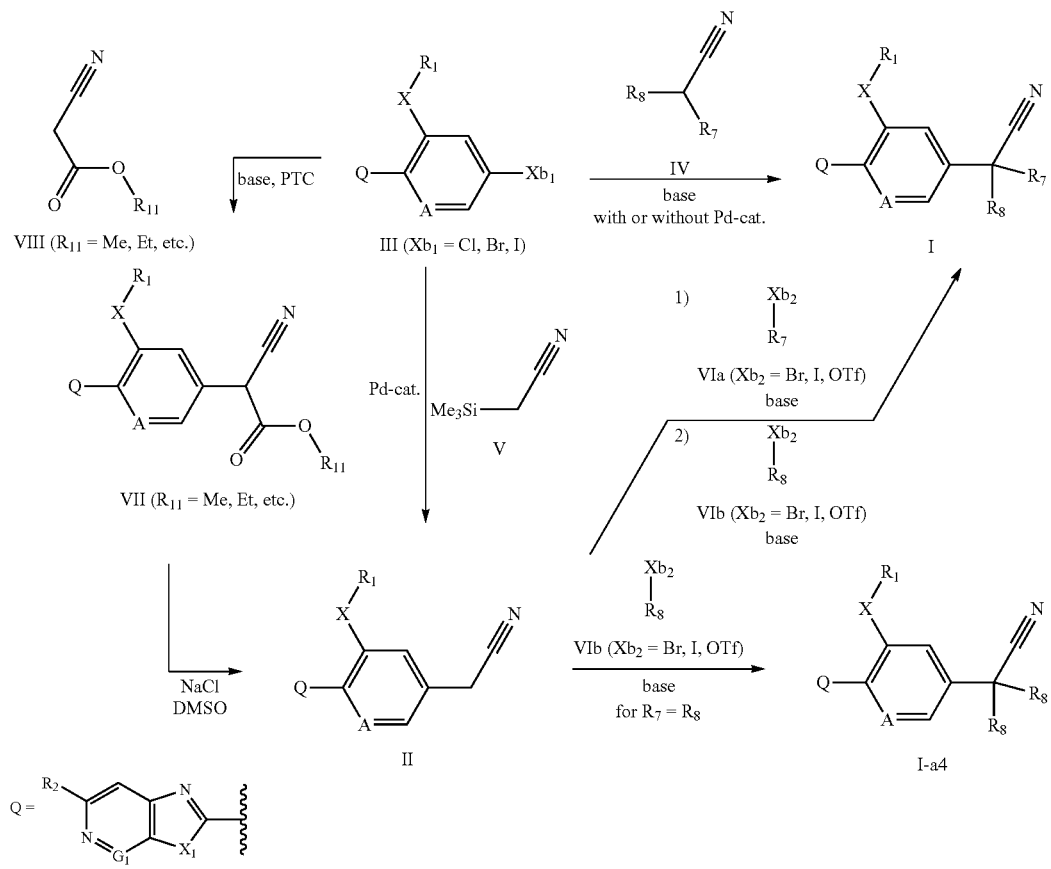

Alternatively, compounds of formula I may be prepared as described in Scheme 3. Treatment of compounds of formula XII, wherein $R_1$, A, X, $R_7$ and $R_8$ are defined as above for formula I, can be activated to compounds of formula XI by methods known to those skilled in the art and described, for example, in *Tetrahedron* 2005, 61 (46), 10827-10852. For example compounds of formula XI where $X_0$ is chlorine are formed by treatment with, for example, oxalyl chloride or thionyl chloride in the presence of catalytic quantities of DMF in inert solvents such as dichloromethane or THF at temperatures between 20° C. to 100° C., preferably 25° C. Treatment of XI with compounds of formula X, wherein $R_2$, $G_1$ and $X_1$ are defined as described in formula I, optionally in the presence of a base, e.g. triethylamine or pyridine, leads to compounds of formula IX. Alternatively, compounds of formula XI can be prepared by treatment of compounds of formula XII with dicyclohexyl carbodiimide (DCC) or 1-ethyl-3-(3-dimethylaminopropyl)carbodiimide (EDC) to give the activated species XI, wherein $X_0$ is $X_{01}$ and $X_{02}$, respectively, in an inert solvent, e.g. pyridine, or tetrahydrofuran (THF) optionally in the presence of a base, e.g., triethylamine, at temperatures between 50-180° C. The obtained compounds of formula IX can then be converted to compounds of formula I by dehydration, e.g., by heating under microwave irradiation, in the presence of an acid catalyst, for example methanesulfonic acid, or para-toluenesulfonic acid, in an inert solvent such as N-methyl pyrrolidone at temperatures between 25-180° C., preferably 130-170° C. Such processes have been described previously in WO 2010/125985. Alternatively, compounds of formula IX can be converted to compounds of formula I (wherein $X_1$ is O) using triphenylphosphine, di-isopropyl azodicarboxylate in an inert solvent such as THF at temperatures between 25-50° C. Such Mitsunobu conditions have been previously described for such transformations (see WO 2009/131237). Compounds of formula X have been previously described, e.g., in WO 2012/086848, WO 2015/000715, and WO 2016/116338.

Compounds of formula XII, wherein $R_1$, A, X, $R_7$ and $R_8$ are defined as above for formula I, can be prepared by methods described in Scheme 4. Synthesis of the required starting materials of formula XV, wherein $R_1$, X, A are defined as above for formula I, and wherein $Xb_1$ can be a halogen, preferentially chlorine, bromine or iodine, or a sulfonate, like for example a trifluoromethanesulfonate, most preferably bromine or iodine, and $R_{LG}$ is $C_1$-$C_4$alkyl, have been previously described, for example in WO 2016/026848. Treatment of compounds of formula XV with trimethylsilyl acetonitrile (V), in the presence of zinc(II) fluoride, and a palladium(0)catalyst such as tris(dibenzylideneacetone)-dipalladium(0)-chloroform adduct ($Pd_2(dba)_3$), a ligand, for example Xantphos, in an inert solvent, such as DMF at temperatures between 100-160° C., optionally under microwave heating, leads to compounds of formula XIV, wherein X is S or $SO_2$, $R_1$, and A are defined as in formula I above and $R_{LG}$ is $C_1$-$C_4$alkyl. Such methods have been described in the literature, e.g. in *J. Am. Chem. Soc.* 2005, 127, 15824-15832. Compounds of formula XIV can be sequentially treated with alkylating reagents of formula VIa or VIb wherein $Xb_2$ is preferably Br, I, or OTf and $R_7$ and $R_8$ is defined under formula I, in the presence of a base, such as sodium hydride, $K_2CO_3$, or $Cs_2CO_3$, in an inert solvent such as THF, DMF, or acetonitrile, to give compounds of formula XIII, wherein X is S or $SO_2$, $R_1$, A, $R_7$ and $R_8$ are defined as in formula I above and $R_{LG}$ is $C_1$-$C_4$alkyl. Alternatively, compounds of formula XIV can be subjected to an excess of the abovementioned base and reagent VIb to obtain compounds of general type XIII-a, wherein $R_7$=$R_8$. Alternatively, compounds of formula XIII can be prepared directly from compounds of formula XV by treatment with compounds of formula IV, wherein $R_7$ and $R_8$ are defined as above for formula I, in the presence or absence of a catalyst such as $Pd_2(dba)_3$, and a ligand, such as BINAP, Scheme 3

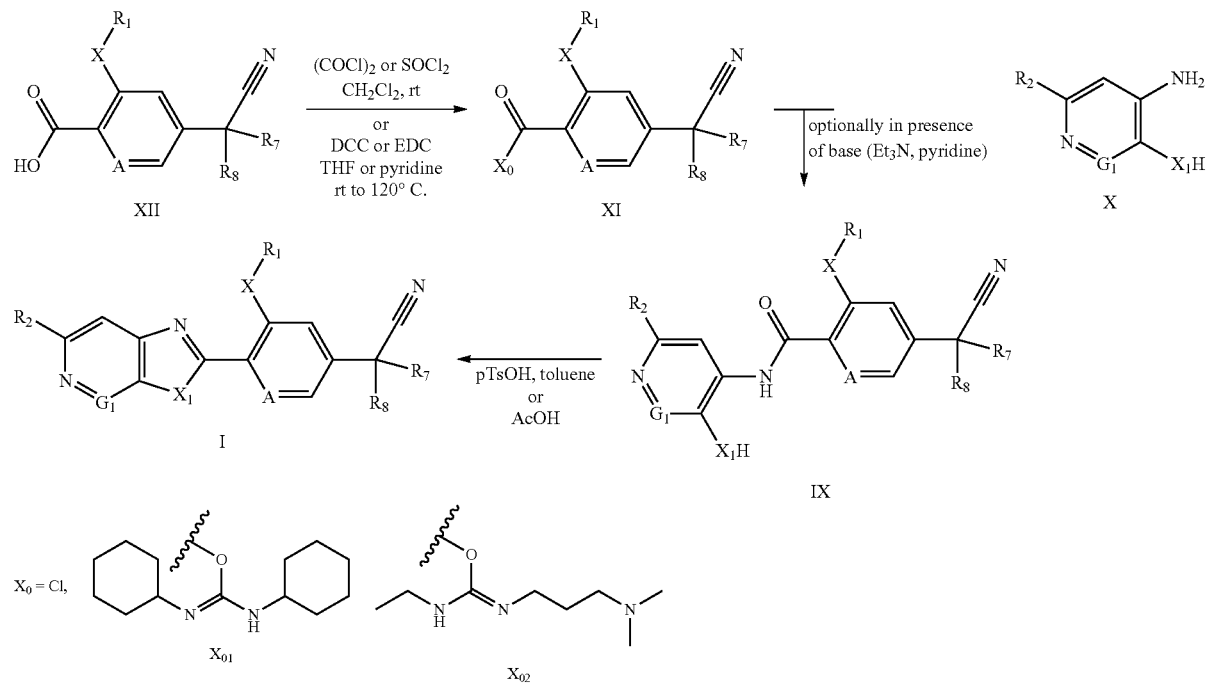

using a strong base such as LiHMDS, in an inert solvent such as THF at temperatures between −20 and 120° C. Such methods have been described in the literature, for example, *J. Am. Chem. Soc.* 2005, 127, 15824-15832; *J. Org. Chem.* 2005, 70, 10186-10189, Org. Lett. 2014, 16, 6314-6317 or *Org. Lett.* 2011, 13, 1690-1693.

Alternatively, compound of formula XIV can be obtained from compounds of formula XVI, wherein A, X, and $R_1$ are defined as under formula I above, $R_{LG}$ and $R_{11}$ independently of each other stand for a $C_1$-$C_8$alkyl group, preferably methyl or ethyl, by Krapcho decarboxylation. Such methods have been described, for example in, *Tetradehron Lett.* 1974, 15, 1091-1094. Compounds of formula XVI may be obtained by reaction of compounds of formula XV with cyanoacetates of formula VIII, wherein $R_{11}$ stands for a $C_1$-$C_6$alkyl group, preferably methyl or ethyl. This reaction may proceed in polar aprotic solvents such as dimethylsulfoxide (DMSO), N,N-dimethylformamide (DMF), or N-methylpyrrolidone (NMP), in the presence of a base, such as $K_2CO_3$ or $Na_2CO_3$, in the presence of absence of a phase-transfer catalyst ("PTC") at temperatures between 20-180° C., preferably 80-140° C. Similarly, transition metal-catalyzed processes are known, see for example, *Angew. Chem. Int. Ed.* 2011, 50, 4470-4474. Compounds of formula XIII or XIII-a can be converted to compounds of formula XII by saponification under conditions known to a person skilled in the art. Compounds of formula IV, V, VIa, VIb, and VIII are commercially available or methods to prepare those compounds are known to a person skilled in the art. Compounds of formula XV are known and their synthesis has been reported in the literature, see for example, WO2016/005263.

Compounds of formula XIII or XIII-a can be converted to compounds of formula XII by saponification under conditions known to a person skilled in the art. Compounds of formula IV, V and VIa, VIb and VIII are commercially available or methods to prepare these compounds are known to a person skilled in the art.

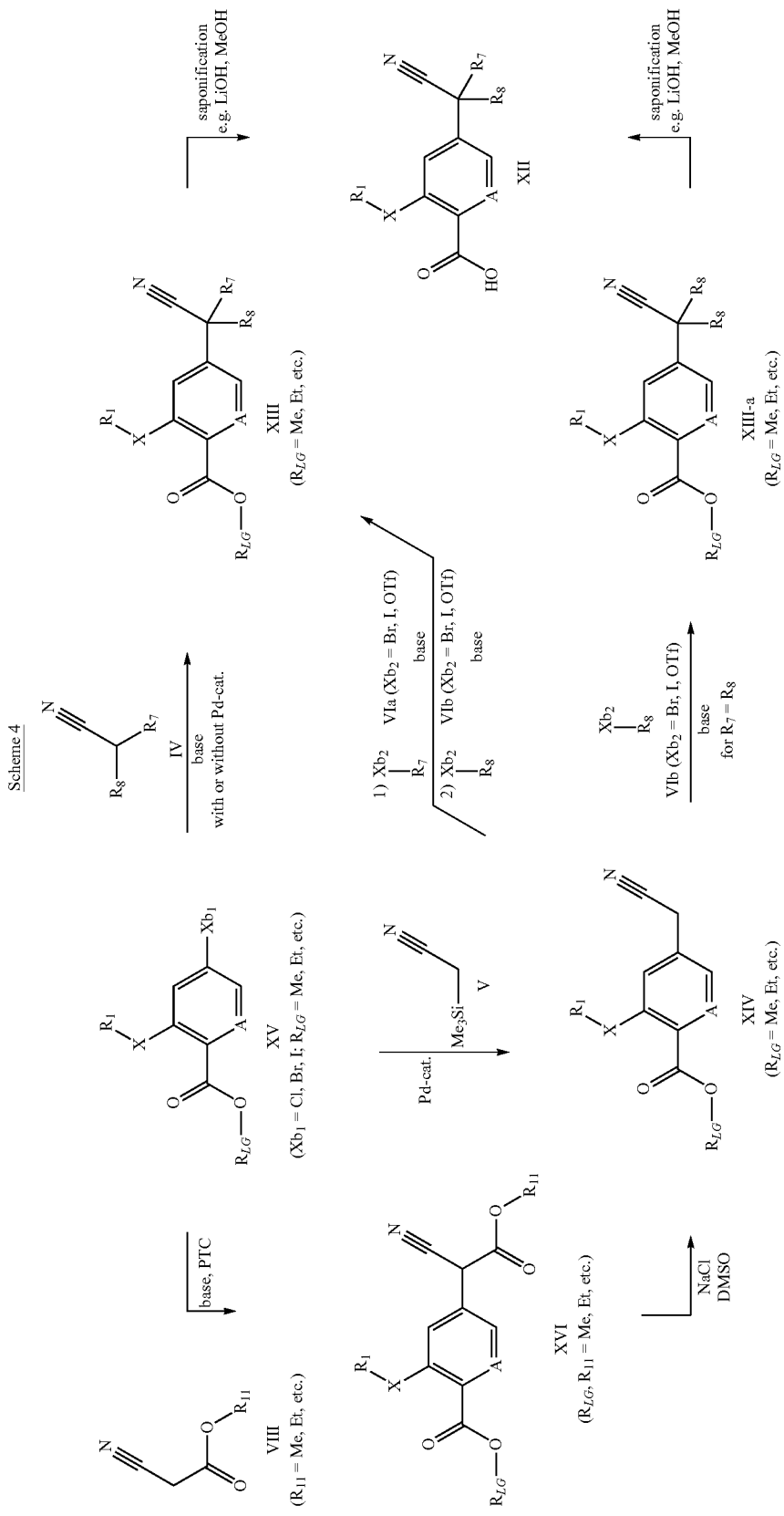

The compounds of formula IX, XI, XII, XIII, XVI are novel, especially developed for the preparation of the compounds of formula I.

Thus in a yet further aspect of the invention there is provided:

compounds of formula IX, $$(IX)$$

wherein
A is CH or N, preferably N;
X is S, SO or SO$_2$, preferably S or SO$_2$;
R$_1$ is C$_1$-C$_4$alkyl, preferably ethyl;
G$_1$ is N or CH;
R$_3$ is hydrogen or C$_1$-C$_4$alkyl, preferably methyl;
R$_2$ is halogen, C$_1$-C$_6$haloalkyl, C$_1$-C$_4$haloalkylsulfanyl, C$_1$-C$_4$haloalkylsulfinyl, C$_1$-C$_4$haloalkylsulfonyl or C$_1$-C$_6$haloalkoxy; preferably CF$_3$;
R$_7$ is hydrogen, halogen, cyano, C$_1$-C$_6$alkyl, C$_1$-C$_6$haloalkyl, C$_3$-C$_6$cycloalkyl, C$_1$-C$_4$alkoxy, C$_1$-C$_4$alkoxyC$_1$-C$_4$alkyl, C$_1$-C$_4$alkylsulfanyl, C$_1$-C$_4$alkylsulfanyl-C$_1$-C$_4$alkyl, C$_1$-C$_4$alkylsulfinyl-C$_1$-C$_4$alkyl, C$_1$-C$_4$alkylsulfonyl-C$_1$-C$_4$alkyl or C$_1$-C$_4$alkyloxycarbonyl, preferably R$_7$ is methyl or fluoro);
and
R$_8$ is halogen, cyano, C$_1$-C$_6$alkyl, C$_1$-C$_6$haloalkyl, C$_3$-C$_6$cycloalkyl, C$_1$-C$_4$alkoxy, C$_1$-C$_4$alkoxy-C$_1$-C$_4$alkyl, C$_1$-C$_4$alkylsulfanyl, C$_1$-C$_4$alkylsulfanyl-C$_1$-C$_4$alkyl, C$_1$-C$_4$alkylsulfinyl-C$_1$-C$_4$alkyl, C$_1$-C$_4$alkylsulfonyl-C$_1$-C$_4$alkyl or C$_1$-C$_4$alkyloxycarbonyl, preferably R$_8$ is methyl or fluoro; or a regioisomer thereof, or an isomeric mixture thereof;
and
compounds of formula XI, $$(XI)$$

wherein
A is CH or N, preferably N;
X is S, SO or SO$_2$, preferably S or SO$_2$;
R$_1$ is C$_1$-C$_4$alkyl, preferably ethyl;
R$_7$ is hydrogen, halogen, cyano, C$_1$-C$_6$alkyl, C$_1$-C$_6$haloalkyl, C$_3$-C$_6$cycloalkyl, C$_1$-C$_4$alkoxy, C$_1$-C$_4$alkoxyC$_1$-C$_4$alkyl, C$_1$-C$_4$alkylsulfanyl, C$_1$-C$_4$alkylsulfanyl-C$_1$-C$_4$alkyl, C$_1$-C$_4$alkylsulfinyl-C$_1$-C$_4$alkyl, C$_1$-C$_4$alkylsulfonyl-C$_1$-C$_4$alkyl or C$_1$-C$_4$alkyloxycarbonyl, preferably R$_7$ is methyl or fluoro;
and
R$_8$ is halogen, cyano, C$_1$-C$_6$alkyl, C$_1$-C$_6$haloalkyl, C$_3$-C$_6$cycloalkyl, C$_1$-C$_4$alkoxy, C$_1$-C$_4$alkoxy-C$_1$-C$_4$alkyl, C$_1$-C$_4$alkylsulfanyl, C$_1$-C$_4$alkylsulfanyl-C$_1$-C$_4$alkyl, C$_1$-C$_4$alkylsulfinyl-C$_1$-C$_4$alkyl, C$_1$-C$_4$alkylsulfonyl-C$_1$-C$_4$alkyl or C$_1$-C$_4$alkyloxycarbonyl, preferably R$_8$ is methyl or fluoro;
and
compounds of formula XII, $$(XII)$$

wherein
A is CH or N, preferably N;
X is S, SO or SO$_2$, preferably S or SO$_2$;
R$_1$ is C$_1$-C$_4$alkyl, preferably ethyl;
R$_7$ is hydrogen, halogen, cyano, C$_1$-C$_6$alkyl, C$_1$-C$_6$haloalkyl, C$_3$-C$_6$cycloalkyl, C$_1$-C$_4$alkoxy, C$_1$-C$_4$alkoxyC$_1$-C$_4$alkyl, C$_1$-C$_4$alkylsulfanyl, C$_1$-C$_4$alkylsulfanyl-C$_1$-C$_4$alkyl, C$_1$-C$_4$alkylsulfinyl-C$_1$-C$_4$alkyl, C$_1$-C$_4$alkylsulfonyl-C$_1$-C$_4$alkyl or C$_1$-C$_4$alkyloxycarbonyl, preferably R$_7$ is methyl or fluoro;
R$_8$ s is halogen, cyano, C$_1$-C$_6$alkyl, C$_1$-C$_6$haloalkyl, C$_3$-C$_6$cycloalkyl, C$_1$-C$_4$alkoxy, C$_1$-C$_4$alkoxy-C$_1$-C$_4$alkyl, C$_1$-C$_4$alkylsulfanyl, C$_1$-C$_4$alkylsulfanyl-C$_1$-C$_4$alkyl, C$_1$-C$_4$alkylsulfinyl-C$_1$-C$_4$alkyl, C$_1$-C$_4$alkylsulfonyl-C$_1$-C$_4$alkyl or C$_1$-C$_4$alkyloxycarbonyl, preferably R$_8$ is methyl or fluoro;
and
compounds of formula XIII, $$(XIII)$$

wherein
A is CH or N, preferably N;
X is S, SO or SO$_2$, preferably S or SO$_2$;
R$_1$ is C$_1$-C$_4$alkyl, preferably ethyl;
R$_7$ is hydrogen, halogen, cyano, C$_1$-C$_6$alkyl, C$_1$-C$_6$haloalkyl, C$_3$-C$_6$cycloalkyl, C$_1$-C$_4$alkoxy, C$_1$-C$_4$alkoxyC$_1$-C$_4$alkyl, C$_1$-C$_4$alkylsulfanyl, C$_1$-C$_4$alkylsulfanyl-C$_1$-C$_4$alkyl, C$_1$-C$_4$alkylsulfinyl-C$_1$-C$_4$alkyl, C$_1$-C$_4$alkylsulfonyl-C$_1$-C$_4$alkyl or C$_1$-C$_4$alkyloxycarbonyl, preferably R$_7$ is methyl or fluoro;
R$_8$ is halogen, cyano, C$_1$-C$_6$alkyl, C$_1$-C$_6$haloalkyl, C$_3$-C$_6$cycloalkyl, C$_1$-C$_4$alkoxy, C$_1$-C$_4$alkoxy-C$_1$-C$_4$alkyl, C$_1$-C$_4$alkylsulfanyl, C$_1$-C$_4$alkylsulfanyl-C$_1$-C$_4$alkyl, $C_1$-$C_4$alkylsulfinyl-$C_1$-$C_4$alkyl, $C_1$-$C_4$alkylsulfonyl-$C_1$-$C_4$alkyl or $C_1$-$C_4$alkyloxycarbonyl, preferably $R_8$ is methyl or fluoro; and $R_{LG}$ is $C_1$-$C_4$alkyl, preferably methyl or ethyl; and compounds of formula XVI,

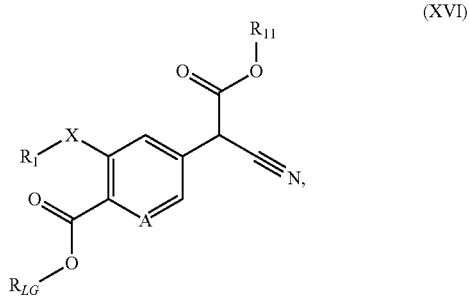

(XVI)

wherein
A is CH or N, preferably N;
X is S, SO or $SO_2$, preferably S or $SO_2$;
$R_1$ is $C_1$-$C_4$alkyl, preferably ethyl;
$R_{11}$ is $C_1$-$C_4$alkyl, preferably methyl or ethyl; and
$R_{LG}$ is $C_1$-$C_4$alkyl, preferably methyl or ethyl.

A by-product regioisomer is sometimes obtained when making compounds of formula (IX), namely compounds of formula (IX-z):

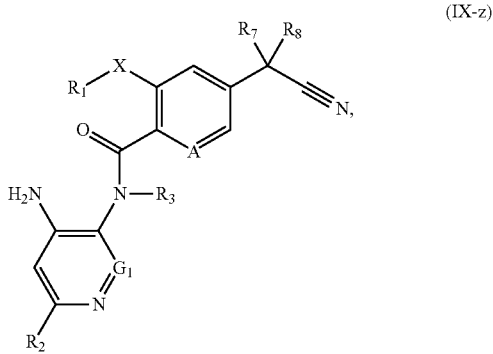

(IX-z)

wherein A, X, $R_1$, $G_1$, $R_3$, $R_2$, $R_7$ and $R_8$ are as defined above for compounds of formula (IX).

The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo [5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140° C., preferably from approximately −30° C. to approximately +100° C., in many cases in the range between ambient temperature and approximately +80° C.

A compound of formula I can be converted in a manner known per se into another compound of formula I by replacing one or more substituents of the starting compound of formula I in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula I can be prepared in a manner known per se. Thus, for example, acid addition salts of compounds of formula I are obtained by treatment with a suitable acid or a suitable ion exchanger reagent and salts with bases are obtained by treatment with a suitable base or with a suitable ion exchanger reagent.

Salts of compounds of formula I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds of formula I can be converted in a manner known per se into other salts of compounds of formula I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula I, which have salt-forming properties can be obtained in free form or in the form of salts.

The compounds of formula I and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds of formula I, in free form or in salt form, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

N-oxides can be prepared by reacting a compound of the formula I with a suitable oxidizing agent, for example the $H_2O_2$/urea adduct in the presence of an acid anhydride, e.g. trifluoroacetic anhydride. Such oxidations are known from the literature, for example from *J. Med. Chem.*, 32 (12), 2561-73, 1989 or WO 00/15615.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula I and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds of Tables X below can be prepared according to the methods described above. The examples which follow are intended to illustrate the invention and show preferred compounds of formula I.

Table X: This table discloses 15 substituent definitions X.001 to X.015 of the formula I:

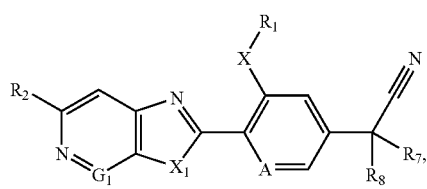

wherein $R_2$, $G_1$, $X_1$, A, $R_1$, $R_7$ and $R_8$ are as defined below:

TABLE X

| Comp. No | $R_2$ | $G_1$ | $X_1$ | A | $R_1$ | $R_7$ | $R_8$ |
|---|---|---|---|---|---|---|---|
| X.001 | $CF_3$ | CH | NMe | N | Et | H | Me |
| X.002 | $CF_3$ | CH | NMe | N | Et | H | Et |
| X.003 | $CF_3$ | CH | NMe | N | Et | H | i-Pr |
| X.004 | $CF_3$ | CH | NMe | N | Et | H | CN |
| X.005 | $CF_3$ | CH | NMe | N | Et | Me | Me |
| X.006 | $CF_3$ | CH | NMe | N | Et | Et | Et |
| X.007 | $CF_3$ | CH | NMe | N | Et | Me | C(O)OEt |
| X.008 | $CF_3$ | CH | NMe | N | Et | H | OMe |
| X.009 | $CF_3$ | CH | NMe | N | Et | Me | OMe |
| X.010 | $CF_3$ | CH | NMe | N | Et | Me | CN |
| X.011 | $CF_3$ | CH | NMe | N | Et | Me | $MeOCH_2$ |
| X.012 | $CF_3$ | CH | NMe | N | Et | F | F |
| X.013 | $CF_3$ | CH | NMe | CH | Et | Me | Me |
| X.014 | $CF_3$ | N | NMe | N | Et | Me | Me |
| X.015 | $CF_3$ | N | NMe | CH | Et | Me | Me |
| X.016 | $C_2F_5$ | CH | NMe | N | Et | Me | Me |
| X.017 | $C_2F_5$ | N | NMe | N | Et | Me | Me |
| X.018 | $SCF_3$ | CH | NMe | N | Et | Me | Me |
| X.019 | $S(O)CF_3$ | CH | NMe | N | Et | Me | Me |
| X.020 | $S(O)_2CF_3$ | CH | NMe | N | Et | Me | Me |
| X.021 | $CF_3$ | N | NMe | CH | Et | Me | Me |
| X.022 | $CF_3$ | CH | NMe | N | Et | Me | F |
| X.023 | Br | CH | NMe | N | Et | Me | Me | and the N-oxides of the compounds of Table X. Me represents the methyl group, Et is the ethyl group, i-Pr is the isopropyl group, C(O)OEt is the ethoxycarbonyl group, MeO is the methoxy group, and $MeOCH_2$ s the methoxymethyl group.

Table 1: This table discloses the 23 compounds 1.001 to 1.023 of the formula I-1, wherein X is S, and $R_2$, $G_1$, $X_1$, A, $R_1$, $R_7$ and $R_8$ are as defined in Table X. For example, compound 1.001 has the following structure:

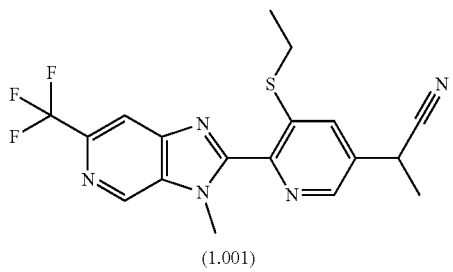 [SMILES: CCSc1cc(C(C)C#N)cnc1-c1nc2cc(C(F)(F)F)ncc2n1C]

(1.001)

Table 2: This table discloses the 23 compounds 2.001 to 2.023 of the formula I-1a, wherein X is SO, and $R_2$, $G_1$, $X_1$, A, $R_1$, $R_7$ and $R_8$ are as defined in Table X.

Table 3: This table discloses the 23 compounds 3.001 to 3.023 of the formula I-1a, wherein X is $SO_2$, and $R_2$, $G_1$, $X_1$, A, $R_1$, $R_7$ and $R_8$ are as defined in Table X.

The compounds of formula I according to the invention are preventively and/or curatively valuable active ingredients in the field of pest control, even at low rates of application, which have a very favorable biocidel spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i.e. in destruction of the pests, which takes place either immediately or only after some time has elapsed, for example during ecdysis, or indirectly, for example in a reduced oviposition and/or hatching rate.

Examples of the abovementioned animal pests are:

from the order Acarina, for example,

*Acalitus* spp., *Aculus* spp., *Acaricalus* spp., *Aceria* spp., *Acarus siro*, *Amblyomma* spp., *Argas* spp., *Boophilus* spp., *Brevipalpus* spp., *Bryobia* spp, *Calipitrimerus* spp., *Chorioptes* spp., *Dermanyssus gallinae*, *Dermatophagoides* spp., *Eotetranychus* spp, *Eriophyes* spp., *Hemitarsonemus* spp., *Hyalomma* spp., *Ixodes* spp., *Olygonychus* spp, *Ornithodoros* spp., *Polyphagotarsone latus*, *Panonychus* spp., *Phyllocoptruta oleivora*, *Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order Anoplura, for example,

*Haematopinus* spp., *Linognathus* spp., *Pediculus* spp., *Pemphigus* spp. and *Phylloxera* spp.; from the order Coleoptera, for example,

*Agriotes* spp., *Amphimallon majale*, *Anomala orientalis*, *Anthonomus* spp., *Aphodius* spp, *Astylus atromaculatus*, *Ataenius* spp, *Atomaria linearis*, *Chaetocnema tibialis*, *Cerotoma* spp, *Conoderus* spp, *Cosmopolites* spp., *Cotinis nitida*, *Curculio* spp., *Cyclocephala* spp, *Dermestes* spp., *Diabrotica* spp., *Diloboderus abderus*, *Epilachna* spp., *Eremnus* spp., *Heteronychus arator*, *Hypothenemus hampei*, *Lagria vilosa*, *Leptinotarsa decemLineata*, *Lissorhoptrus* spp., *Liogenys* spp, *Maecolaspis* spp, *Maladera castanea*, *Megascelis* spp, *Melighetes aeneus*, *Melolontha* spp., *Myochrous armatus*, *Orycaephilus* spp., *Otiorhynchus* spp., *Phyllophaga* spp, *Phlyctinus* spp., *Popillia* spp., *Psylliodes* spp., *Rhyssomatus aubtilis*, *Rhizopertha* spp., *Scarabeidae*, *Sitophilus* spp., *Sitotroga* spp., *Somaticus* spp, *Sphenophorus* spp, *Sternechus subsignatus*, *Tenebrio* spp., *Tribolium* spp. and *Trogoderma* spp.; from the order Diptera, for example,

*Aedes* spp., *Anopheles* spp, *Antherigona soccata*, *Bactrocea pleas*, *Bibio hortulanus*, *Bradysia* spp, *Calliphora erythrocephala*, *Ceratitis* spp., *Chrysomyia* spp., *Culex* spp., *Cuterebra* spp., *Dacus* spp., *Delia* spp, *Drosophila melanogaster*, *Fannia* spp., *Gastrophilus* spp., *Geomyza tripunctata*, *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit*, *Pegomyia hyoscyami*, *Phorbia* spp., *Rhagoletis* spp, *Rivelia quadrifasciata*, *Scatella* spp, *Sciara* spp., *Stomoxys* spp., *Tabanus* spp., *Tannia* spp. and *Tipula* spp.;

from the order Hemiptera, for example,

*Acanthocoris scabrator*, *Acrosternum* spp, *Adelphocoris lineolatus*, *Amblypelta nitida*, *Bathycoelia thalassina*, *Blissus* spp, *Cimex* spp., *Clavigralla tomentosicollis*, *Creontiades* spp, *Distantiella theobroma*, *Dichelops furcatus*, *Dysdercus* spp., *Edessa* spp, *Euchistus* spp., *Eurydema pulchrum*, *Eurygaster* spp., *Halyomorpha halys*, *Horcias nobilellus*, *Leptocorisa* spp., *Lygus* spp., *Margarodes* spp., *Murgantia histrionic*, *Neomegalotomus* spp, *Nesidiocoris tenuis*, *Nezara* spp., *Nysius simulans*, *Oebalus insularis*, *Piesma* spp., *Piezodorus* spp, *Rhodnius* spp., *Sahlbergella singularis*, *Scaptocoris castanea*, *Scotinophara* spp., *Thyanta* spp, *Triatoma* spp., *Vatiga illudens*;

*Acyrthosium pisum*, *Adalges* spp, *Agalliana ensigera*, *Agonoscena targionii*, *Aleurodicus* spp, *Aleurocanthus* spp, *Aleurolobus barodensis*, *Aleurothrixus floccosus*, *Aleyrodes brassicae*, *Amarasca biguttula*, *Amritodus atkinsoni*, *Aonidiella* spp., *Aphididae*, *Aphis* spp., *Aspidiotus* spp., *Aulacorthum solani*, *Bactericera cockerelli*, *Bemisia* spp, *Brachycaudus* spp, *Brevicoryne brassicae*, *Cacopsylla* spp., *Cavariella aegopodii* Scop., *Ceroplaster* spp., *Chrysomphalus aonidium*, *Chrysomphalus dictyospermi*, *Cicadella* spp, *Cofana spectra*, *Cryptomyzus* spp, *Cicadulina* spp, *Coccus hesperidum*, *Dalbulus maidis*, *Dialeurodes* spp, *Diaphorina citri*, *Diuraphis noxia*, *Dysaphis* spp., *Empoasca* spp., *Eriosoma larigerum*, *Erythroneura* spp., *Gascardia* spp., *Glycaspis brimblecombei*, *Hyadaphis pseudobrassicae*, *Hyalopterus* spp, *Hyperomyzus pallidus*, *Idioscopus clypealis*, *Jacobiasca lybica*, *Laodelphax* spp., *Lecanium corni*, *Lepidosaphes* spp., *Lopaphis erysimi*, *Lyogenys maidis*, *Macrosiphum* spp., *Mahanarva* spp, *Metcalfa pruinosa*, *Metopolophium dirhodum*, *Myndus crudus*, *Myzus* spp., *Neotoxoptera sp*, *Nephotettix* spp., *Nilaparvata* spp., *Nippolachnus piri Mats*, *Odonaspis ruthae*, *Oregma lanigera* Zehnter, *Parabemisia myricae*, *Paratrioza cockerelli*, *Parlatoria* spp., *Pemphigus* spp., *Peregrinus maidis*, *Perkinsiella* spp, *Phorodon humuli*, *Phylloxera* spp, *Planococcus* spp., *Pseudaulacaspis* spp., *Pseudococcus* spp., *Pseudatomoscelis seriatus*, *Psylla* spp., *Pulvinaria aethiopica*, *Quadraspidiotus* spp., *Quesada gigas*, *Recilia dorsalis*, *Rhopalosiphum* spp., *Saissetia* spp., *Scaphoideus* spp., *Schizaphis* spp., *Sitobion* spp., *Sogatella furcifera*, *Spissistilus festinus*, *Tarophagus Proserpina*, *Toxoptera* spp, *Trialeurodes* spp, *Tridiscus sporoboli*, *Trionymus* spp, *Trioza erytreae*, *Unaspis citri*, *Zygina flammigera*, *Zyginidia scutellaris*;

from the order Hymenoptera, for example,

*Acromyrmex*, *Arge* spp., *Atta* spp., *Cephus* spp., *Diprion* spp., *Diprionidae*, *Gilpinia polytoma*, *Hoplo-campa* spp., *Lasius* spp., *Monomorium pharaonis*, *Neodiprion* spp., *Pogonomyrmex* spp., *Slenopsis invicta*, *Solenopsis* spp. and *Vespa* spp.;

from the order Isoptera, for example,

*Coptotermes* spp, *Corniternes cumulans*, *Incisitermes* spp, *Macrotermes* spp, *Mastotermes* spp, *Microtermes* spp, *Reticulitermes* spp.; *Solenopsis geminate* from the order Lepidoptera, for example,

*Acleris* spp., *Adoxophyes* spp., *Aegeria* spp., *Agrotis* spp., *Alabama argillaceae*, *Amylois* spp., *Anticarsia gemmatalis*, *Archips* spp., *Argyresthia* spp., *Argyrotaenia* spp., *Autographa* spp., *Bucculatrix thurberiella*, *Busseola fusca*, *Cadra cautella*, *Carposina nipponensis*, *Chilo* spp., *Choristoneura* spp., *Chrysoteuchia topiaria*, *Clysia ambiguella*, *Cnaphalocrocis* spp., *Cnephasia* spp., *Cochylis* spp., *Coleophora* spp., *Colias lesbia*, *Cosmophila flava*, *Crambus* spp, *Crocidolomia binotalis*, *Cryptophlebia leucotreta*, *Cydalima perspectalis*, *Cydia* spp., *Diaphania perspectalis*, *Diatraea* spp., *Diparopsis castanea*, *Earias* spp., *Eldana saccharina*, *Ephestia* spp., *Epinotia* spp, *Estigmene acrea*, *Etiella zinckinella*, *Eucosma* spp., *Eupoecilia ambiguella*, *Euproctis* spp., *Euxoa* spp., *Feltia jaculiferia*, *Gra-pholita* spp., *Hedya nubiferana*, *Heliothis* spp., *Hellula undalis*, *Herpetogramma* spp, *Hyphantria cunea*, *Keiferia lycopersicella*, *Lasmopalpus lignosellus*, *Leucoptera scitella*, *Lithocollethis* spp., *Lobesia botrana*, *Loxostege bifidalis*, *Lymantria* spp., *Lyonetia* spp., *Malacosoma* spp., *Mamestra brassicae*, *Manduca sexta*, *Mythimna* spp, *Noctua* spp, *Operophtera* spp., *Orniodes indica*, *Ostrinia nubilalis*, *Pammene* spp., *Pandemis* spp., *Panolis flammea*, *Papaipema nebris*, *Pectinophora gossypiela*, *Perileucoptera coffeella*, *Pseudaletia unipuncta*, *Phthorimaea operculella*, *Pieris rapae*, *Pieris* spp., *Plutella xylostella*, *Prays* spp., *Pseudoplusia* spp, *Rachiplusia nu*, *Richia albicosta*, *Scirpophaga* spp., *Sesamia* spp., *Sparganothis* spp., *Spodoptera* spp., *Sylepta derogate*, *Synanthedon* spp., *Thaumetopoea* spp., *Tortrix* spp., *Trichoplusia ni*, *Tuta absoluta*, and *Yponomeuta* spp.;

from the order Mallophaga, for example,
*Damalinea* spp. and *Trichodectes* spp.;
from the order Orthoptera, for example,
*Blatta* spp., *Blattella* spp., *Gryllotalpa* spp., *Leucophaea maderae*, *Locusta* spp., *Neocurtilla hexadactyla*, *Periplaneta* spp., *Scapteriscus* spp, and *Schistocerca* spp.;
from the order Psocoptera, for example,
*Liposcelis* spp.;
from the order Siphonaptera, for example,
*Ceratophyllus* spp., *Ctenocephalides* spp. and *Xenopsylla cheopis*;
from the order Thysanoptera, for example,
*Calliothrips phaseoli*, *Frankliniella* spp., *Heliothrips* spp, *Hercinothrips* spp., *Parthenothrips* spp, *Scirtothrips aurantii*, *Sericothrips variabilis*, *Taeniothrips* spp., *Thrips* spp;
from the order Thysanura, for example, *Lepisma saccharina*.

The active ingredients according to the invention can be used for controlling, i.e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, *Asparagus*, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family and latex plants.

The compositions and/or methods of the present invention may be also used on any ornamental and/or vegetable crops, including flowers, shrubs, broad-leaved trees and evergreens. For example the invention may be used on any of the following ornamental species: *Ageratum* spp.,
*Alonsoa* spp., *Anemone* spp., *Anisodontea capsenisis*, *Anthemis* spp., *Antirrhinum* spp., *Aster* spp., *Begonia* spp. (e.g. *B. elatior*, *B. semperflorens*, *B. tubéreux*), *Bougainvillea* spp., *Brachycome* spp., *Brassica* spp. (ornamental), *Calceolaria* spp., *Capsicum annuum*, *Catharanthus roseus*, *Canna* spp., *Centaurea* spp., *Chrysanthemum* spp., *Cineraria* spp. (*C. maritime*), *Coreopsis* spp., *Crassula coccinea*, *Cuphea ignea*, *Dahlia* spp., *Delphinium* spp., *Dicentra spectabilis*, *Dorotheantus* spp., *Eustoma grandiflorum*, *Forsythia* spp., *Fuchsia* spp., *Geranium gnaphalium*, *Gerbera* spp., *Gomphrena globosa*, *Heliotropium* spp., *Helianthus* spp., *Hibiscus* spp., *Hortensia* spp., *Hydrangea* spp., *Hypoestes phyllostachya*, *Impatiens* spp. (*I. Walleriana*), *Iresines* spp., *Kalanchoe* spp., *Lantana camara*, *Lavatera trimestris*, *Leonotis leonurus*, *Lilium* spp., *Mesembryanthemum* spp., *Mimulus* spp., *Monarda* spp., *Nemesia* spp., *Tagetes* spp., *Dianthus* spp. (carnation), *Canna* spp., *Oxalis* spp., *Bellis* spp., *Pelargonium* spp. (*P. peltatum*, *P. Zonale*), *Viola* spp. (pansy), *Petunia* spp., *Phlox* spp., *Plecthranthus* spp., *Poinsettia* spp., *Parthenocissus* spp. (*P. quinquefolia*, *P. tricuspidata*), *Primula* spp., *Ranunculus* spp., *Rhododendron* spp., *Rosa* spp. (rose), *Rudbeckia* spp., *Saintpaulia* spp., *Salvia* spp., *Scaevola aemola*, *Schizanthus wisetonensis*, *Sedum* spp., *Solanum* spp., *Surfinia* spp., *Tagetes* spp., *Nicotinia* spp., *Verbena* spp., *Zinnia* spp. and other bedding plants.

For example the invention may be used on any of the following vegetable species: *Allium* spp. (*A. sativum*, *A. cepa*, *A. oschaninii*, *A. Porrum*, *A. ascalonicum*, *A. fistulosum*), *Anthriscus cerefolium*, *Apium graveolus*, *Asparagus officinalis*, *Beta vulgarus*, *Brassica* spp. (*B. Oleracea*, *B. Pekinensis*, *B. rapa*), *Capsicum annuum*, *Cicer arietinum*, *Cichorium endivia*, *Cichorum* spp. (*C. intybus*, *C. endivia*), *Citrillus lanatus*, *Cucumis* spp. (*C. sativus*, *C. melo*), *Cucurbita* spp. (*C. pepo*, *C. maxima*), *Cyanara* spp. (*C. scolymus*, *C. cardunculus*), *Daucus carota*, *Foeniculum vulgare*, *Hypericum* spp., *Lactuca sativa*, *Lycopersicon* spp. (*L. esculentum*, *L. lycopersicum*), *Mentha* spp., *Ocimum basilicum*, *Petroselinum crispum*, *Phaseolus* spp. (*P. vulgaris*, *P. coccineus*), *Pisum sativum*, *Raphanus sativus*, *Rheum rhaponticum*, *Rosemarinus* spp., *Salvia* spp., *Scorzonera hispanica*, *Solanum melongena*, *Spinacea oleracea*, *Valerianella* spp. (*V. locusta*, *V. eriocarpa*) and *Vicia faba*.

Preferred ornamental species include African violet, Begonia, Dahlia, Gerbera, Hydrangea, Verbena, Rosa, Kalanchoe, Poinsettia, Aster, Centaurea, Coreopsis, Delphinium, Monarda, Phlox, Rudbeckia, Sedum, Petunia, Viola, Impatiens, Geranium, Chrysanthemum, Ranunculus, Fuchsia, Salvia, Hortensia, rosemary, sage, St. Johnswort, mint, sweet pepper, tomato and cucumber.

The active ingredients according to the invention are especially suitable for controlling *Aphis craccivora*, *Diabrotica balteata*, *Heliothis virescens*, *Myzus persicae*, *Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatos) and *Chilo supressalis* (preferably in rice).

The active ingredients according to the invention are especially suitable for controlling *Aphis craccivora*, *Diabrotica balteata*, *Heliothis virescens*, *Myzus persicae*, *Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatos) and *Chilo supressalis* (preferably in rice).

In a further aspect, the invention may also relate to a method of controlling damage to plant and parts thereof by plant parasitic nematodes (Endoparasitic-, Semiendoparasitic- and Ectoparasitic nematodes), especially plant parasitic nematodes such as root knot nematodes, *Meloidogyne hapla*, *Meloidogyne incognita*, *Meloidogyne javanica*, *Meloidogyne arenaria* and other *Meloidogyne* species; cyst-forming nematodes, *Globodera rostochiensis* and other *Globodera* species; *Heterodera avenae*, *Heterodera glycines*, *Heterodera schachtii*, *Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor*, *Ditylenchus dipsaci* and other *Dity-* lenchus species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Pratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus, Rotylenchus reniformis* and other *Rotylenchus* species; *Scutellonema* species; Stubby root nematodes, *Trichodorus primitivus* and other *Trichodorus* species, Paratrichodorus species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina* spp., *Hypsoperine* spp., *Macroposthonia* spp., *Melinius* spp., *Punctodera* spp., and *Quinisulcius* spp.

The compounds of the invention may also have activity against the molluscs. Examples of which include, for example, Ampullariidae; Arion (*A. ater, A. circumscriptus, A. hortensis, A. rufus*); Bradybaenidae (*Bradybaena fruticum*); Cepaea (*C. hortensis, C. Nemoralis*); ochlodina; Deroceras (*D. agrestis, D. empiricorum, D. laeve, D. reticulatum*); Discus (*D. rotundatus*); Euomphalia; Galba (*G. trunculata*); Helicelia (*H. itala, H. obvia*); Helicidae Helicigona arbustorum); Helicodiscus; Helix (*H. aperta*); Limax (*L. cinereoniger, L. flavus, L. marginatus, L. maximus, L. tenellus*); Lymnaea; Milax (*M. gagates, M. marginatus, M. sowerbyi*); Opeas; Pomacea (*P. canaticulata*); Vallonia and Zanitoides.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as *Streptomycetes* toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810). Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. Cryl-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and moths (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.

4. MON 863 Maize from Monsanto Europe S. A. 270-272 Avenue de Tervuren, B-1150 Brussels, Belgium, registration number C/DE/02/9. MON 863 expresses a Cry3Bb1 toxin and has resistance to certain Coleoptera insects.

5. IPC 531 Cotton from Monsanto Europe S. A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S. A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

Transgenic crops of insect-resistant plants are also described in BATS (Zentrum für Biosicherheit und Nachhaltigkeit, Zentrum BATS, Clarastrasse 13, 4058 Basel, Switzerland) Report 2003, (http://bats.ch).

The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818 and EP-A-0 353 191. The methods of producing such transgenic plants are generally known to the person skilled in the art and are described, for example, in the publications mentioned above.

Crops may also be modified for enhanced resistance to fungal (for example *Fusarium*, Anthracnose, or *Phytophthora*), bacterial (for example *Pseudomonas*) or viral (for example potato leafroll virus, tomato spotted wilt virus, cucumber mosaic virus) pathogens.

Crops also include those that have enhanced resistance to nematodes, such as the soybean cyst nematode.

Crops that are tolerance to abiotic stress include those that have enhanced tolerance to drought, high salt, high temperature, chill, frost, or light radiation, for example through expression of NF-YB or other proteins known in the art.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Further areas of use of the compositions according to the invention are the protection of stored goods and store rooms and the protection of raw materials, such as wood, textiles, floor coverings or buildings, and also in the hygiene sector, especially the protection of humans, domestic animals and productive livestock against pests of the mentioned type.

The present invention also provides a method for controlling pests (such as mosquitoes and other disease vectors; see also http://www.who.int/malaria/vector_control/irs/en/). In one embodiment, the method for controlling pests comprises applying the compositions of the invention to the target pests, to their locus or to a surface or substrate by brushing, rolling, spraying, spreading or dipping. By way of example, an IRS (indoor residual spraying) application of a surface such as a wall, ceiling or floor surface is contemplated by the method of the invention. In another embodiment, it is contemplated to apply such compositions to a substrate such as non-woven or a fabric material in the form of (or which can be used in the manufacture of) netting, clothing, bedding, curtains and tents.

In one embodiment, the method for controlling such pests comprises applying a pesticidally effective amount of the compositions of the invention to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment, it is contemplated to apply such compositions for residual control of pests on a substrate such as a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO 2008/151984, WO 2003/034823, U.S. Pat. No. 5,631,072, WO 2005/64072, WO2006/128870, EP 1724392, WO 2005113886 or WO 2007/090739.

Further areas of use of the compositions according to the invention are the field of tree injection/trunk treatment for all ornamental trees as well all sort of fruit and nut trees.

In the field of tree injection/trunk treatment, the compounds according to the present invention are especially suitable against wood-boring insects from the order Lepidoptera as mentioned above and from the order Coleoptera, especially against woodborers listed in the following tables A and B:

TABLE A

Examples of exotic woodborers of economic importance.

| Family | Species | Host or Crop Infested |
|---|---|---|
| Buprestidae | *Agrilus planipennis* | Ash |
| Cerambycidae | *Anoplura glabripennis* | Hardwoods |
| Scolytidae | *Xylosandrus crassiusculus* | Hardwoods |
| | *X. mutilatus* | Hardwoods |
| | *Tomicus piniperda* | Conifers |

TABLE B

Examples of native woodborers of economic importance.

| Family | Species | Host or Crop Infested |
|---|---|---|
| Buprestidae | *Agrilus anxius* | Birch |
| | *Agrilus politus* | Willow, Maple |
| | *Agrilus sayi* | Bayberry, Sweetfern |
| | *Agrilus vittaticoillis* | Apple, Pear, Cranberry, Serviceberry, Hawthorn |
| | *Chrysobothris femorata* | Apple, Apricot, Beech, Boxelder, Cherry, Chestnut, Currant, Elm, Hawthorn, Hackberry, Hickory, Horsechestnut, Linden, Maple, Mountain-ash, Oak, Pecan, Pear, Peach, Persimmon, Plum, Poplar, Quince, Redbud, Serviceberry, Sycamore, Walnut, Willow |
| | *Texania campestris* | Basswood, Beech, Maple, Oak, Sycamore, Willow, Yellow-poplar |
| Cerambycidae | *Goes pulverulentus* | Beech, Elm, Nuttall, Willow, Black oak, Cherrybark oak, Water oak, Sycamore |
| | *Goes tigrinus* | Oak |
| | *Neoclytus acuminatus* | Ash, Hickory, Oak, Walnut, Birch, Beech, Maple, Eastern hophornbeam, Dogwood, Persimmon, Redbud, Holly, Hackberry, Black locust, Honeylocust, Yellow-poplar, Chestnut, Osage-orange, Sassafras, Lilac, Mountain-mahogany, Pear, Cherry, Plum, Peach, Apple, Elm, Basswood, Sweetgum |
| | *Neoptychodes trilineatus* | Fig, Alder, Mulberry, Willow, Netleaf hackberry |
| | *Oberea ocellata* | Sumac, Apple, Peach, Plum, Pear, Currant, Blackberry |
| | *Oberea tripunctata* | Dogwood, Viburnum, Elm, Sourwood, Blueberry, Rhododendron, Azalea, Laurel, Poplar, Willow, Mulberry |
| | *Oncideres cingulata* | Hickory, Pecan, Persimmon, Elm, Sourwood, Basswood, Honeylocust, Dogwood, Eucalyptus, Oak, Hackberry, Maple, Fruit trees |
| | *Saperda calcarata* | Poplar |
| | *Strophiona nitens* | Chestnut, Oak, Hickory, Walnut, Beech, Maple |
| Scolytidae | *Corthylus columbianus* | Maple, Oak, Yellow-poplar, Beech, Boxelder, Sycamore, Birch, Basswood, Chestnut, Elm |
| | *Dendroctonus frontalis* | Pine |
| | *Dryocoetes betulae* | Birch, Sweetgum, Wild cherry, Beech, Pear |
| | *Monarthrum fasciatum* | Oak, Maple, Birch, Chestnut, Sweetgum, Blackgum, Poplar, Hickory, Mimosa, Apple, Peach, Pine |
| | *Phloeotribus liminaris* | Peach, Cherry, Plum, Black cherry, Elm, Mulberry, Mountain-ash |
| | *Pseudopityophthorus pruinosus* | Oak, American beech, Black cherry, Chickasaw plum, Chestnut, Maple, Hickory, Hornbeam, Hophornbeam |
| Sesiidae | *Paranthrene simulans* | Oak, American chestnut |
| | *Sannina uroceriformis* | Persimmon |
| | *Synanthedon exitiosa* | Peach, Plum, Nectarine, Cherry, Apricot, Almond, Black cherry |
| | *Synanthedon pictipes* | Peach, Plum, Cherry, Beach, Black Cherry |
| | *Synanthedon rubrofascia* | Tupelo |
| | *Synanthedon scitula* | Dogwood, Pecan, Hickory, Oak, Chestnut, Beech, Birch, Black cherry, Elm, Mountain-ash, Viburnum, Willow, Apple, Loquat, Ninebark, Bayberry |
| | *Vitacea polistiformis* | Grape |

The present invention may be also used to control any insect pests that may be present in turfgrass, including for example beetles, caterpillars, fire ants, ground pearls, millipedes, sow bugs, mites, mole crickets, scales, mealybugs ticks, spittlebugs, southern chinch bugs and white grubs. The present invention may be used to control insect pests at various stages of their life cycle, including eggs, larvae, nymphs and adults.

In particular, the present invention may be used to control insect pests that feed on the roots of turfgrass including white grubs (such as *Cyclocephala* spp. (e.g. masked chafer, *C. lurida*), *Rhizotrogus* spp. (e.g. European chafer, *R. majalis*), *Cotinus* spp. (e.g. Green June beetle, *C. nitida*), *Popillia* spp. (e.g. Japanese beetle, *P. japonica*), *Phyllophaga* spp. (e.g. May/June beetle), *Ataenius* spp. (e.g. Black turfgrass *Ataenius, A. spretulus*), *Maladera* spp. (e.g. Asiatic garden beetle, *M. castanea*) and *Tomarus* spp.), ground pearls (*Margarodes* spp.), mole crickets (tawny, southern, and short-winged; *Scapteriscus* spp., *Gryllotalpa africana*) and leatherjackets (European crane fly, *Tipula* spp.).

The present invention may also be used to control insect pests of turfgrass that are thatch dwelling, including armyworms (such as fall armyworm *Spodoptera frugiperda*, and common armyworm *Pseudaletia unipuncta*), cutworms, billbugs (*Sphenophorus* spp., such as *S. venatus verstitus* and *S. parvulus*), and sod webworms (such as *Crambus* spp. and the tropical sod webworm, *Herpetogramma phaeopteralis*).

The present invention may also be used to control insect pests of turfgrass that live above the ground and feed on the turfgrass leaves, including chinch bugs (such as southern chinch bugs, *Blissus insularis*), Bermudagrass mite (*Eriophyes cynodoniensis*), rhodesgrass mealybug (*Antonina graminis*), two-lined spittlebug (*Propsapia bicincta*), leafhoppers, cutworms (Noctuidae family), and greenbugs. The present invention may also be used to control other pests of turfgrass such as red imported fire ants (*Solenopsis invicta*) that create ant mounds in turf.

In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis*, *Periplaneta americana*, *Blattelagermanica* and *Supella* spp.

Of the subclass Acaria (Acarida) and the orders Meta- and Meso-stigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (*Astigmata*), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus*, *Chlorophorus pilosis*, *Anobium punctatum*, *Xestobium rufovillosum*, *Ptilinuspecticornis*, *Dendrobium pertinex*, *Ernobius mollis*, *Priobium carpini*, *Lyctus brunneus*, *Lyctus africanus*, *Lyctus planicollis*, *Lyctus linearis*, *Lyctus pubescens*, *Trogoxylon aequale*, Minthesrugicollis, *Xyleborus* spec., Tryptodendron spec., *Apate monachus*, *Bostrychus capucins*, *Heterobostrychus brunneus*, *Sinoxylon* spec. and *Dinoderus minutus*, and also hymenopterans such as *Sirex juvencus*, *Urocerus gigas*, *Urocerus gigas* taignus and *Urocerus augur*, and termites such as *Kalotermes flavicollis*, *Cryptotermes brevis*, *Heterotermes indicola*, *Reticulitermes flavipes*, *Reticulitermes santonensis*, *Reticulitermes lucifugus*, *Mastotermes darwiniensis*, *Zootermopsis nevadensis* and *Coptotermes formosanus*, and bristletails such as *Lepisma saccharina*.

The compounds according to the invention can be used as pesticidal agents in unmodified form, but they are generally formulated into compositions in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO and WHO Specifications for Pesticides, United Nations, First Edition, Second Revision (2010). Such formulations can either be used directly or diluted prior to use. The dilutions can be made, for example, with water, liquid fertilisers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof.

The active ingredients can also be contained in very fine microcapsules. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances. A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in McCutcheon's Detergents and Emulsifiers Annual, MC Publishing Corp., Ridgewood N.J. (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and liquid and solid fertilisers.

The compositions according to the invention can include an additive comprising an oil of vegetable or animal origin, a mineral oil, alkyl esters of such oils or mixtures of such oils and oil derivatives. The amount of oil additive in the composition according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid (methyl laurate, methyl palmitate and methyl oleate, respectively). Many oil derivatives are known from the Compendium of Herbicide Adjuvants, 10th Edition, Southern Illinois University, 2010.

The inventive compositions generally comprise from 0.1 to 99% by weight, especially from 0.1 to 95% by weight, of compounds of the present invention and from 1 to 99.9% by weight of a formulation adjuvant which preferably includes from 0 to 25% by weight of a surface-active substance. Whereas commercial products may preferably be formulated as concentrates, the end user will normally employ dilute formulations.

The rates of application vary within wide limits and depend on the nature of the soil, the method of application, the crop plant, the pest to be controlled, the prevailing climatic conditions, and other factors governed by the method of application, the time of application and the target crop. As a general guideline compounds may be applied at a rate of from 1 to 2000 l/ha, especially from 10 to 1000 l/ha.

Preferred formulations can have the following compositions (weight %):
Emulsifiable Concentrates:
    active ingredient: 1 to 95%, preferably 60 to 90%
    surface-active agent: 1 to 30%, preferably 5 to 20%
    liquid carrier: 1 to 80%, preferably 1 to 35%
Dusts:
    active ingredient: 0.1 to 10%, preferably 0.1 to 5%
    solid carrier: 99.9% to 90%, preferably 99.9 to 99%
Suspension Concentrates:
    active ingredient: 5 to 75%, preferably 10 to 50%
    water: 94 to 24%, preferably 88 to 30%
    surface-active agent: 1 to 40%, preferably 2 to 30%
Wettable Powders:
    active ingredient: 0.5 to 90%, preferably 1 to 80%
    surface-active agent: 0.5 to 20%, preferably 1 to 15%
    solid carrier: 5 to 95%, preferably 15 to 90%
Granules:
    active ingredient: 0.1 to 30%, preferably 0.1 to 15%
    solid carrier: 99.5 to 70%, preferably 97 to 85%

The following Examples further illustrate, but do not limit, the invention.

| Wettable powders | a) | b) | c) |
|---|---|---|---|
| active ingredients | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The combination is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredients | 25% | 50% | 75% |
| light mineral oil | 5% | 5% | 5% |
| highly dispersed silicic acid | 5% | 5% | — |
| Kaolin | 65% | 40% | — |
| Talcum | — | — | 20% |

The combination is thoroughly mixed with the adjuvants and the mixture is thoroughly ground in a suitable mill, affording powders that can be used directly for seed treatment.

| Emulsifiable concentrate | |
| --- | --- |
| active ingredients | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
| --- | --- | --- | --- |
| Active ingredients | 5% | 6% | 4% |
| Talcum | 95% | — | — |
| Kaolin | — | 94% | — |
| mineral filler | — | — | 96% |

Ready-for-use dusts are obtained by mixing the combination with the carrier and grinding the mixture in a suitable mill. Such powders can also be used for dry dressings for seed.

| Extruder granules | |
| --- | --- |
| Active ingredients | 15% |
| sodium lignosulfonate | 2% |
| carboxymethylcellulose | 1% |
| Kaolin | 82% |

The combination is mixed and ground with the adjuvants, and the mixture is moistened with water. The mixture is extruded and then dried in a stream of air.

| Coated granules | |
| --- | --- |
| Active ingredients | 8% |
| polyethylene glycol (mol. wt. 200) | 3% |
| Kaolin | 89% |

The finely ground combination is uniformly applied, in a mixer, to the kaolin moistened with polyethylene glycol. Non-dusty coated granules are obtained in this manner.

Suspension Concentrate

| | |
| --- | --- |
| active ingredients | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Flowable Concentrate for Seed Treatment

| | |
| --- | --- |
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of the combination are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredients. The medium capsule diameter is 8-15 microns. The resulting formulation is applied to seeds as an aqueous suspension in an apparatus suitable for that purpose.

Formulation types include an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP), a soluble granule (SG) or any technically feasible formulation in combination with agriculturally acceptable adjuvants.

PREPARATORY EXAMPLES

"Mp" means melting point in ° C. Free radicals represent methyl groups. $^1$H NMR measurements were recorded on a Brucker 400 MHz spectrometer, chemical shifts are given in ppm relevant to a TMS standard. Spectra measured in deuterated solvents as indicated. Either one of the LCMS methods below was used to characterize the compounds. The characteristic LCMS values obtained for each compound were the retention time ("Rt", recorded in minutes) and the measured molecular ion $(M+H)^+$ or $(M-H)^-$.

LCMS Methods:

Method 1: Standard 1

Spectra were recorded on a Mass Spectrometer from Waters (SQD, SQDII Single quadrupole mass spectrometer) equipped with an electrospray source (Polarity: positive and negative ions, Capillary: 3.00 kV, Cone range: 30 V, Extractor: 2.00 V, Source Temperature: 150° C., Desolvation Temperature: 350° C., Cone Gas Flow: 50 l/h, Desolvation Gas Flow: 650 l/h, Mass range: 100 to 900 Da) and an Acquity UPLC from Waters: Binary pump, heated column compartment, diode-array detector and ELSD detector. Column: Waters UPLC HSS T3, 1.8 µm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH, gradient: 10-100% B in 1.2 min; Flow (ml/min) 0.85.

Method 2: Standard Long

Spectra were recorded on a Mass Spectrometer from Waters (SQD, SQDII Single quadrupole mass spectrometer) equipped with an electrospray source (Polarity: positive and negative ions), Capillary: 3.00 kV, Cone range: 30V, Extractor: 2.00 V, Source Temperature: 150° C., Desolvation Temperature: 350° C., Cone Gas Flow: 50 l/h, Desolvation Gas Flow: 650 l/h, Mass range: 100 to 900 Da) and an Acquity UPLC from Waters: Binary pump, heated column compartment, diode-array detector and ELSD detector. Column: Waters UPLC HSS T3, 1.8 µm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH, gradient: 10-100% B in 2.7 min; Flow (ml/min) 0.85.

Method 3: Standard 2 Long

Spectra were recorded on a Mass Spectrometer from Agilent Technologies (6410 Triple Quadruple Mass Spectrometer) equipped with an electrospray source (Polarity: Positive and Negative Polarity Switch, Capillary: 4.00 kV, Fragmentor: 100.00 V, Gas Temperature: 350° C., Gas Flow: 11 L/min, Nebulizer Gas: 45 psi, Mass range: 110-1000 Da, DAD Wavelength range: 210-400 nm). Column: KINETEX EVO C18, length 50 mm, diameter 4.6 mm, particle size 2.6 µm. Column oven temperature 40° C. Solvent gradient: A=Water with 0.1% formic acid: Acetonitrile (95:5 v/v). B=Acetonitrile with 0.1% formic acid. Gradient=0 min 90% A, 10% B; 0.9-1.8 min 0% A, 100% B, 2.2-2.5 min 90% A, 10% B. Flow rate 1.8 mL/min.

Method 4: Standard 2

Spectra were recorded on a Mass Spectrometer from Waters (Acquity SDS Mass Spectrometer) equipped with an electrospray source (Polarity: Positive and Negative Polarity Switch, Capillary: 3.00 kV, Cone Voltage: 41.00 V, Source temperature: 150° C., Desolvation Gas Flow: 1000 L/Hr, Desolvation temperature: 500° C., Gas Flow @Cone: 50 L/hr, Mass range: 110-800 Da, PDA wavelength range: 210-400 nm. Column: Acquity UPLC HSS T3 C18, length 30 mm, diameter 2.1 mm, particle size 1.8 µm. Column oven temperature 40° C. Solvent gradient: A=Water with 0.1% formic acid: Acetonitrile (95:5 v/v). B=Acetonitrile with 0.05% formic acid. Gradient=0 min 90% A, 10% B; 0.2 min 50% A, 50% B; 0.7-1.3 min 0% A, 100% B; 1.4-1.6 min 90% A, 10% B. Flow rate 0.8 mL/min.

Example P1: Preparation of 2-[5-ethylsulfonyl-6-[3-methyl-6-(trifluoromethyl)imidazo[4,5-c]pyridin-2-yl]-3-pyridyl]-2-methyl-propanedinitrile (compound P1)

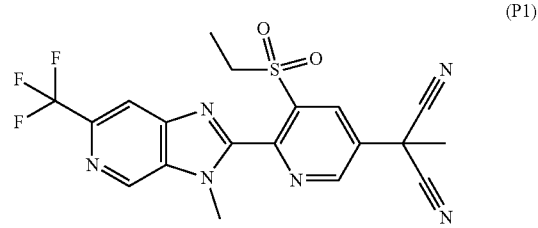 [SMILES: CCS(=O)(=O)c1cc(C(C)(C#N)C#N)cnc1-c1nc2cc(C(F)(F)F)ncc2n1C]

(P1)

Step 1: Preparation of 2-[5-ethylsulfanyl-6-[3-methyl-6-(trifluoromethyl)imidazo[4,5-c]pyridin-2-yl]-3-pyridyl]propanedinitrile (compound P7)

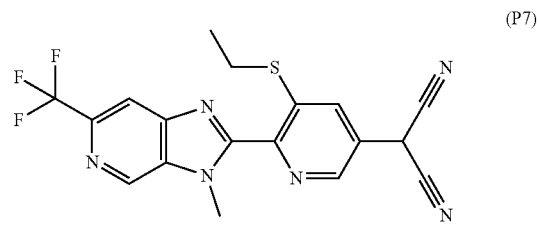 [SMILES: CCSc1cc(C(C#N)C#N)cnc1-c1nc2cc(C(F)(F)F)ncc2n1C]

(P7)

A microwave vial was charged with 2-(5-bromo-3-ethylsulfanyl-2-pyridyl)-3-methyl-6-(trifluoromethyl)imidazo[4,5-c]pyridine (prepared according to WO16096584) (5.00 g, 12.0 mmol), propanedinitrile (0.830 ml, 13.2 mmol, 1.10 equiv.), potassium hydroxide (2.02 g, 36.0 mmol, 3.00 equiv.) and bis(triphenylphosphine)palladium(II) dichloride (420 mg, 0.60 mmol, 0.05 equiv.) After addition of N-methyl-pyrrolidone (24 mL) the reaction mixture was degassed with argon for 5 min: The vessel was sealed and heated in an oil bath at 130° C. overnight. After cooling to room temperature, the reaction mixture was poured into water, the pH was carefully acidified with 2M HCl, and the aqueous phase was extracted twice with ethyl acetate. The combined organic phases were washed twice with water, and these combined aqueous phases were extracted again three times with dichloromethane. A solid precipitated from the combined dichloromethane phases, which was filtered. Both ethyl acetate and dichloromethane organic phases were combined, dried over sodium sulfate, filtered and concentrated under vacuum. The crude dark brown oil was purified by column chromatography over silica gel, eluting with pure ethyl acetate. The selected fractions were evaporated to yield the title compound as a brown solid. LCMS (method 1): 403 (M+H)$^+$; retention time: 0.86 min.

Step 2: Preparation of 2-[5-ethylsulfanyl-6-[3-methyl-6-(trifluoromethyl)imidazo[4,5-c]pyridin-2-yl]-3-pyridyl]-2-methyl-propanedinitrile (compound P8)

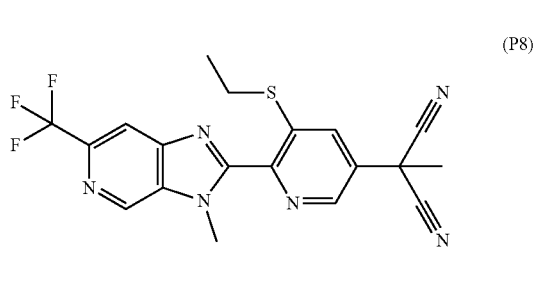 [SMILES: CCSc1cc(C(C)(C#N)C#N)cnc1-c1nc2cc(C(F)(F)F)ncc2n1C]

(P8)

To a of solution of 2-[5-ethylsulfanyl-6-[3-methyl-6-(trifluoromethyl)imidazo[4,5-c]pyridin-2-yl]-3-pyridyl]propanedinitrile (9.58 g, 10.7 mmol) in N,N-dimethylformamide (32 ml) under argon atmosphere was added potassium carbonate (1.58 g, 11.3 mmol, 1.05 equiv.), followed by dropwise addition of methyl iodide (1.00 ml, 16.1 mmol, 1.50 equiv.). The resulting brown mixture was stirred at 40° C. for 2 hours. Additional potassium carbonate (148 mg, 1.07 mmol, 0.10 equiv.) and methyl iodide (1.00 ml, 16.1 mmol, 1.50 equiv.) were added, and the reaction mixture was heated further 3 hours at 40° C. After completion of the reaction, the reaction mixture was cooled down to room temperature and diluted with water. The aqueous phase was slightly acidified with 2M HCl, and extracted twice with ethyl acetate. The combined organic phases were washed four times with water, dried over sodium sulfate, filtered and concentrated. The residue was subjected to column chromatography over silica gel, eluting with ethyl acetate in dichloromethane to yield the title compound as a tan solid. LCMS (method 1): 417 (M+H)$^+$; retention time: 1.01 min.

Step 3: Preparation of 2-[5-ethylsulfonyl-6-[3-methyl-6-(trifluoromethyl)imidazo[4,5-c]pyridin-2-yl]-3-pyridyl]-2-methyl-propanedinitrile (compound P1)

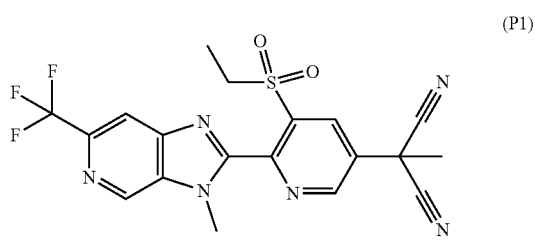 [SMILES: CCS(=O)(=O)c1cc(C(C)(C#N)C#N)cnc1-c1nc2cc(C(F)(F)F)ncc2n1C]

(P1)

To a solution of 2-[5-ethylsulfanyl-6-[3-methyl-6-(trifluoromethyl)imidazo[4,5-c]pyridin-2-yl]-3-pyridyl]-2-methyl-propanedinitrile (100 mg, 0.24 mmol) in dichloromethane (30 ml) under argon atmosphere at 0° C. was added 3-chloroperbenzoic acid (91 mg, 0.53 mmol, 2.2 equiv.). After stirring for 30 min at 0° C. then 1 hour at room temperature, the reaction mixture was slowly quenched by pouring into a saturated sodium thiosulfate solution. The aqueous phase was extracted twice with ethyl acetate, the combined organic phases were dried over sodium sulfate, filtered and concentrated. The crude material was first triturated in diisopropyl ether, and the resulting white solid was further purified by column chromatography over silica gel, eluting with ethyl acetate in dichloromethane to give the title compound as a white solid. LCMS (method 1): 449 (M+H)$^+$; retention time: 0.95 min.

Example P2: Preparation of 2-[5-ethylsulfonyl-6-[7-methyl-3-(trifluoromethyl)imidazo[4,5-c]pyridazin-6-yl]-3-pyridyl]-2-methyl-propanenitrile (compound P2)

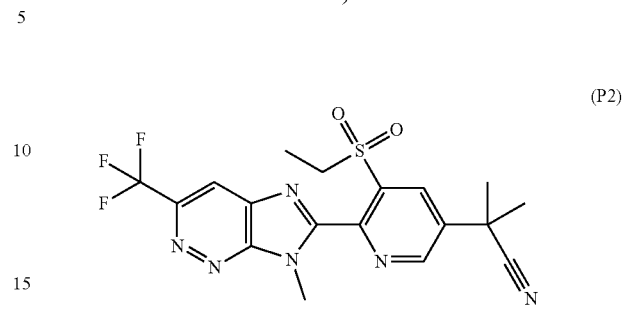

(P2)

Step 1: Preparation of methyl 5-(1-cyano-1-methyl-ethyl)-3-ethylsulfonyl-pyridine-2-carboxylate

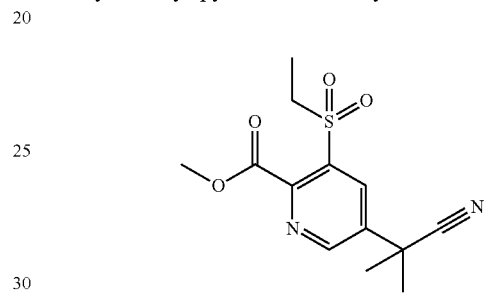

Methyl 5-(cyanomethyl)-3-ethylsulfonyl-pyridine-2-carboxylate (prepared according to WO16096584) (1.40 g, 5.22 mmol) was dissolved in DMF (21 ml) under argon. The reaction mixture was cooled to 0° C., and sodium hydride (480 mg, 12.5 mmol, 2.40 equiv.) was added portionwise. The deep red reaction mixture was stirred for 30 min at 0° C. This reaction mixture was added to a solution of methyl iodide (0.78 ml, 12.5 mmol, 2.40 equiv.) in DMF (21 ml) at 0° C. via syringe. The resulting mixture was slowly allowed to warm up to room temperature and stirred overnight. After completion of the reaction, the mixture was poured into a saturated aqueous ammonium chloride solution, and the aqueous phase was extracted with ethyl acetate. The organic phase was washed four times with water and then brine, dried over sodium sulfate, filtered and concentrated. The crude material was purified by column chromatography over silica gel, eluting with ethyl acetate in cyclohexane to yield the title compound as a white solid. LCMS (method 1): 297 (M+H)$^+$; retention time: 0.77 min.

Step 2: Preparation of 5-(1-cyano-1-methyl-ethyl)-3-ethylsulfonyl-pyridine-2-carboxylic acid

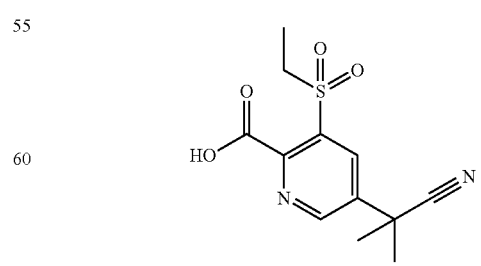

Methyl 5-(1-cyano-1-methyl-ethyl)-3-ethylsulfonyl-pyridine-2-carboxylate (1.40 g, 4.72 mmol) was dissolved in tetrahydrofurane (40 ml) and water (13 ml). Lithium hydroxide (170 mg, 7.09 mmo, 1.50 equiv.) was added and the reaction mixture was stirred at room temperature overnight. The reaction mixture was concentrated, and the pH of the aqueous residue was adjusted to pH 1 with 1M HCl. The resulting white suspension was filtered, the solid washed with a minimum of cold water and dried under vacuum, giving the desired product. The compound was used directly in the next step without further purification. LCMS (method 1): 283 (M+H)$^+$; retention time: 0.42 min.

Step 3: Preparation of 5-(1-cyano-1-methyl-ethyl)-3-ethylsulfonyl-pyridine-2-carbonyl chloride

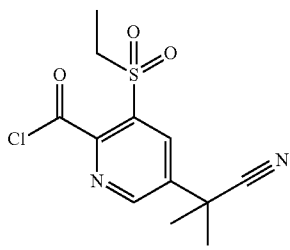 [SMILES: CCS(=O)(=O)c1cc(C(C)(C)C#N)cnc1C(=O)Cl]

5-(1-cyano-1-methyl-ethyl)-3-ethylsulfonyl-pyridine-2-carboxylic acid (1.02 g, 3.61 mmol) was dissolved in dichloromethane (24 ml) under argon, along with a catalytic amount of N,N-dimethylformamide. Oxalyl chloride (0.47 ml, 5.42 mmol, 1.50 equiv.) was added dropwise via syringe. The reaction mixture was then heated at reflux for 3 hours. After cooling down to room temperature, the reaction mixture was evaporated to dryness. The resulting brown oil was used in the next step directly.

Step 4: Preparation of 5-(1-cyano-1-methyl-ethyl)-3-ethylsulfonyl-N-[3-(methylamino)-6-(trifluoromethyl)pyridazin-4-yl]pyridine-2-carboxamide

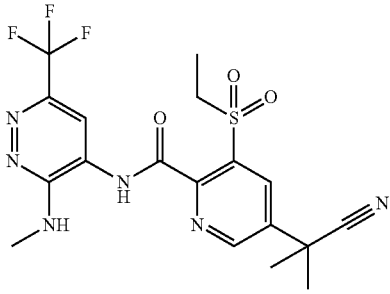 [SMILES: CCS(=O)(=O)c1cc(C(C)(C)C#N)cnc1C(=O)Nc1cc(C(F)(F)F)nnc1NC]

N-3-methyl-6-(trifluoromethyl)pyridazine-3,4-diamine (prepared according to WO2016/116338) (150 mg, 0.78 mmol) was dissolved in tetrahydrofuran (5.0 ml) along with N,N'-diisopropylethylamine. The reaction mixture was cooled to 0° C., and a solution of 5-(1-cyano-1-methyl-ethyl)-3-ethylsulfonyl-pyridine-2-carbonyl chloride (258 mg, 1.1 equiv.) in tetrahydrofuran (5.0 ml) was added dropwise. The reaction mixture was slowly warmed up to room temperature and stirred overnight. The reaction was slowly quenched by addition of a saturated aqueous ammonium chloride solution, and the aqueous phase was extracted three times with ethyl acetate. The combined organic phases were washed with water, brine, dried over sodium sulfate, filtered and concentrated. The crude material was used in the next step directly without purification. LCMS (method 1): 425 (M+H)$^+$; retention time: 1.03 min.

Step 5: Preparation of 2-[5-ethylsulfonyl-6-[7-methyl-3-(trifluoromethyl)imidazo[4,5-c]pyridazin-6-yl]-3-pyridyl]-2-methyl-propanenitrile

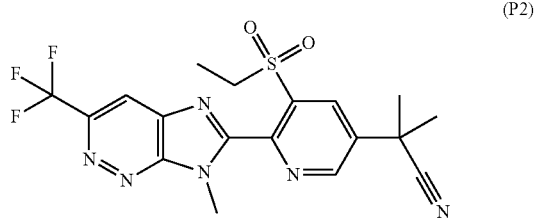 [SMILES: CCS(=O)(=O)c1cc(C(C)(C)C#N)cnc1-c1nc2cc(C(F)(F)F)nnc2n1C]

(P2)

5-(1-cyano-1-methyl-ethyl)-3-ethylsulfonyl-N-[3-(methylamino)-6-(trifluoromethyl)pyridazin-4-yl]pyridine-2-carboxamide (250 mg, 0.55 mmol) was dissolved in acetic acid (1.64 ml) and the reaction mixture was heated to 100° C. for 5 hours. The reaction mixture was concentrated, and the residue was evaporated with toluene to remove the excess of acetic acid. The crude material was purified by column chromatography over silica gel, eluting with ethyl acetate in cyclohexane followed by trituration in diethyl ether to yield the title compound as a white solid. LCMS (method 1): 439 (M+H)$^+$; retention time: 0.93 min.

Example P3: Preparation of 2-ethyl-2-[5-ethylsulfonyl-6-[3-methyl-6-(trifluoromethyl)imidazo[4,5-c]pyridin-2-yl]-3-pyridyl]butanenitrile (compound P3)

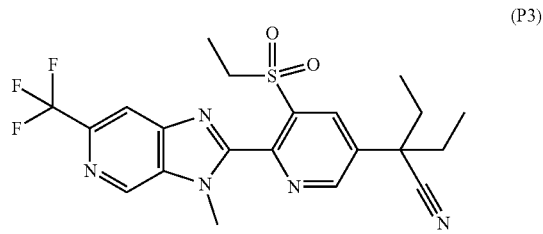 [SMILES: CCC(C#N)(CC)c1cnc(-c2nc3cc(C(F)(F)F)ncc3n2C)c(S(=O)(=O)CC)c1]

(P3)

Step 1: Preparation of 2-[5-ethylsulfonyl-6-[3-methyl-6-(trifluoromethyl)imidazo[4,5-c]pyridin-2-yl]-3-pyridyl]acetonitrile

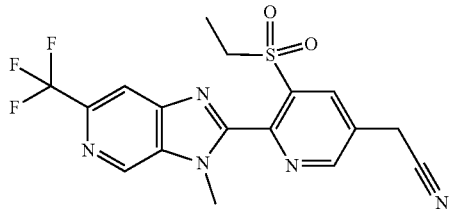

A microwave vial was charged with a solution of 2-(5-bromo-3-ethylsulfonyl-2-pyridyl)-3-methyl-6-(trifluoromethyl)imidazo[4,5-c]pyridine (prepared according to WO16096584) (6.00 g, 13.4 mmol) in N,N-dimethylformamide (27 ml). To this solution under argon atmosphere, trimethylsilyl acetonitrile (2.77 ml, 20.0 mmol, 1.50 equiv.), zinc fluoride (837 mg, 8.01 mmol, 0.60 equiv.), xantphos (315 mg, 0.53 mmol, 0.04 equiv.) and Pd$_2$(dba)$_3$ (250 mg, 0.27 mmol, 0.02 equiv.) were added. The vial was sealed and heated at 140° C. for 30 min in the microwave. The reaction mixture was diluted with ethyl acetate, washed three times with water and once with brine. The organic layer was dried over sodium sulfate, filtered and concentrated. The crude material was purified by column chromatography over silica gel, eluting with methanol in dichloromethane, to yield the title compound as a white solid. LCMS (method 1): 410 (M+H)$^+$; retention time: 0.86 min.

Step 2: Preparation of 2-ethyl-2-[5-ethylsulfonyl-6-[3-methyl-6-(trifluoromethyl)imidazo[4,5-c]pyridin-2-yl]-3-pyridyl]butanenitrile

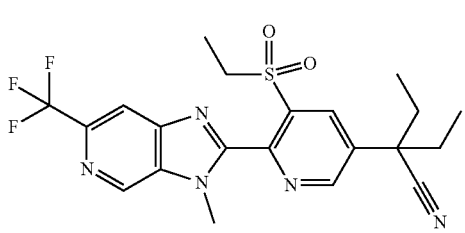

(P3)

2-[5-ethylsulfonyl-6-[3-methyl-6-(trifluoromethyl)imidazo[4,5-c]pyridin-2-yl]-3-pyridyl]acetonitrile (500 mg, 1.22 mmol) was dissolved in N,N-dimethylformamide (5 ml) under argon. The reaction mixture was cooled down to 0° C. Sodium hydride (66 mg, 1.71 mmol, 1.40 equiv.) was added carefully portionwise. The deep red reaction mixture was stirred at 0° C. for 30 min. The obtained solution was added to a solution of ethyl iodide (0.137 ml, 1.71 mmol, 1.40 equiv.) in DMF (5 ml) under argon at 0° C. via syringe. The resulting mixture was slowly warmed up to room temperature and stirred overnight. The mixture was then poured slowly into a saturated aqueous ammonium chloride solution, and the aqueous phase was extracted with ethyl acetate. The organic phase was washed four times with water then brine, dried over sodium sulfate, filtered and concentrated. The crude material was purified by column chromatography over silica gel, eluting with ethyl acetate in cyclohexane to yield the title compound as a white solid. LCMS (method 1): 466 (M+H)$^+$; retention time: 1.02 min.

Example P4: Preparation of 2-[5-ethylsulfonyl-6-[3-methyl-6-(trifluoromethyl)imidazo[4,5-c]pyridin-2-yl]-3-pyridyl]butanenitrile (compound P4)

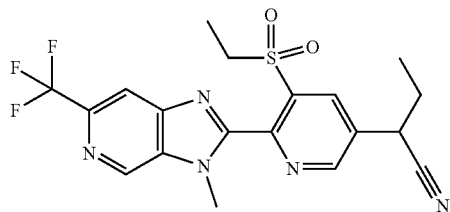

(P4)

2-[5-ethylsulfonyl-6-[3-methyl-6-(trifluoromethyl)imidazo[4,5-c]pyridin-2-yl]-3-pyridyl]acetonitrile (prepared as described in step 1 of EXAMPLE P3) (500 mg, 1.22 mmol) was dissolved in N,N-dimethylformamide (5 ml) under argon. The reaction mixture was cooled down to 0° C. Sodium hydride (66 mg, 1.71 mmol, 1.40 equiv.) was added carefully portionwise. The deep red reaction mixture was stirred at 0° C. for 30 min. The obtained reaction mixture was added dropwise to a solution of ethyl iodide (0.137 ml, 1.71 mmol, 1.40 equiv.) in DMF (5 ml) under argon at 0° C. The resulting mixture was slowly warmed up to room temperature and stirred overnight. The mixture was then poured slowly into a saturated aqueous ammonium chloride solution, and the aqueous phase was extracted with ethyl acetate. The organic phase was washed four times with water then brine, dried over sodium sulfate, filtered and concentrated. The crude material was purified by column chromatography over silica gel, eluting with ethyl acetate in cyclohexane to yield the title compound as a white solid. LCMS (method 1): 438 (M+H)$^+$; retention time: 0.94 min.

Example P5: Preparation of 2-[5-ethylsulfonyl-6-[3-methyl-6-(trifluoromethyl)imidazo[4,5-c]pyridin-2-yl]-3-pyridyl]-2-methyl-propanenitrile (compound P5)

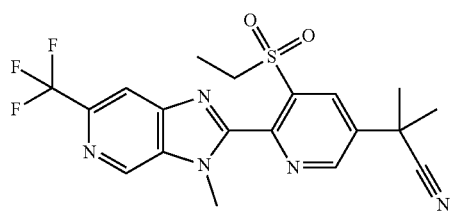

(P5)

2-[5-ethylsulfonyl-6-[3-methyl-6-(trifluoromethyl)imidazo[4,5-c]pyridin-2-yl]-3-pyridyl]acetonitrile (prepared as described in step 1 of EXAMPLE P3) (400 mg, 0.98 mmol) was dissolved in N,N-dimethylformamide (4 ml) under argon. The reaction mixture was cooled down to 0° C. Sodium hydride (52 mg, 1.37 mmol, 1.40 equiv.) was added carefully portionwise. The deep red reaction mixture was stirred at 0° C. for 30 min. The obtained mixture was added to a solution of methyl iodide (0.085 ml, 1.37 mmol, 1.40 equiv.) in DMF (4 ml) under argon at 0° C. The resulting mixture was slowly warmed up to room temperature and stirred overnight. The mixture was then poured slowly into a saturated aqueous ammonium chloride solution, and the aqueous phase was extracted with ethyl acetate. The organic phase was washed four times with water then brine, dried over sodium sulfate, filtered and concentrated. The crude material was purified by column chromatography over silica gel, eluting with ethyl acetate in cyclohexane to yield the title compound as a white solid. LCMS (method 1): 438 (M+H)$^+$; retention time: 0.93 min.

Example P6: Preparation of 2-[5-ethylsulfonyl-6-[3-methyl-6-(trifluoromethyl)imidazo[4,5-c]pyridin-2-yl]-3-pyridyl]propanenitrile (compound P6)

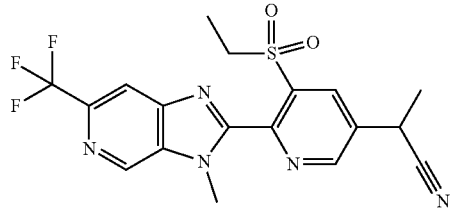 [SMILES: CCS(=O)(=O)c1cc(CC#N)cnc1-c1nc2cc(C(F)(F)F)ncc2n1C]

(P6)

22-[5-ethylsulfonyl-6-[3-methyl-6-(trifluoromethyl)imidazo[4,5-c]pyridin-2-yl]-3-pyridyl]acetonitrile (prepared as described in step 1 of EXAMPLE P3) (400 mg, 0.98 mmol) was dissolved in N,N-dimethylformamide (4 ml) under argon. The reaction mixture was cooled down to 0° C. Sodium hydride (52 mg, 1.37 mmol, 1.40 equiv.) was added carefully portionwise. The deep red reaction mixture was stirred at 0° C. for 30 min. The obtained mixture was added to a solution of methyl iodide (0.085 ml, 1.37 mmol, 1.40 equiv.) in DMF (4 ml) under argon at 0° C. The resulting mixture was slowly warmed up to room temperature and stirred overnight. The mixture was then poured slowly into a saturated aqueous ammonium chloride solution, and the aqueous phase was extracted with ethyl acetate. The organic phase was washed four times with water then brine, dried over sodium sulfate, filtered and concentrated. The crude material was purified by column chromatography over silica gel, eluting with ethyl acetate in cyclohexane to yield the title compound as a white solid. LCMS (method 1): 424 (M+H)$^+$; retention time: 1.32 min.

Alternative procedure for the preparation of 2-[5-ethylsulfonyl-6-[3-methyl-6-(trifluoromethyl)imidazo[4,5-c]pyridin-2-yl]-3-pyridyl]propanenitrile (compound P6):

To a solution of ethyl 2-cyano-2-[5-ethylsulfonyl-6-[3-methyl-6-(trifluoromethyl)imidazo[4,5-c]pyridin-2-yl]-3-pyridyl]propanoate (compound P9) (250 mg, 0.505 mmol, 1.00 equiv.) in DMSO (2.0 mL) was added sodium chloride (298 mg, 5.05 mmoL, 10.0 equiv.) in water (1.0 mL) and the obtained reaction mixture was heated to 120° C. for 2 h. After cooling to room temp. the reaction mixture was diluted with water (10 mL) and extracted with ethyl acetate (3×20 mL). The combined organic layers were dried (Na$_2$SO$_4$), filtered and concentrated in vacuo to give the crude product. Purification by flash chromatography (SiO2, 30% ethyl acetate/cyclohexane) furnished the desired product. LCMS (method 4): 424 (M+H)$^+$; retention time: 0.91 min.

Example P9: Preparation of ethyl 2-cyano-2-[5-ethylsulfonyl-6-[3-methyl-6-(trifluoromethyl)imidazo[. 4,5-c]pyridin-2-yl]-3-pyridyl]propanoate (compound P9)

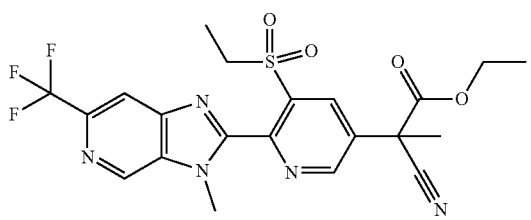

Step 1: Preparation of ethyl 2-cyano-2-[5-ethylsulfonyl-6-[3-methyl-6-(trifluoromethyl)imidazo[4,5-c]pyridin-2-yl]-3-pyridyl]acetate (compound P25):

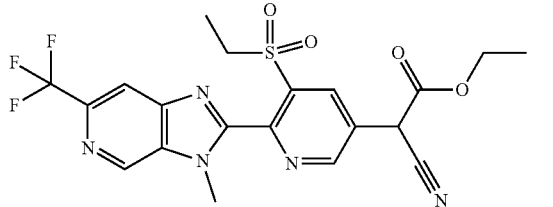

To a solution of 2-(5-bromo-3-ethylsulfonyl-2-pyridyl)-3-methyl-6-(trifluoromethyl)imidazo[4,5-c]pyridine (prepared according to WO16096584) (5.40 g, 11.1 mmol, 1.00 equiv.) in DMSO (50 mL) was added ethyl 2-cyanoacetate (3.85 g, 33.3 mmol, 3.00 equiv.) followed by potassium carbonate (3.89 g, 27.8 mmol, 2.50 equiv.), L-proline (261 mg, 2.23 mmol, 0.200 equiv.) and copper(I) iodide (212 mg, 1.11 mmol, 0.100 equiv.). The raction mixture was heated to 150° C. for 3.5 h. After cooling to room temp. the reaction mixture was acidified with 2N HCl solution (50 mL), extracted with ethyl acetate (3×100 mL) and the combined organic layers were washed with brine, dried (sodium sulfate), filtered and contracted under reduced pressure to obtain the desired product. LCMS (method 4): 482 (M+H)$^+$; retention time: 0.95 min.

Step 2: Preparation of ethyl 2-cyano-2-[5-ethylsulfonyl-6-[3-methyl-6-(trifluoromethyl)imidazo[4,5-c]pyridin-2-yl]-3-pyridyl]propanoate (corn pound P9)

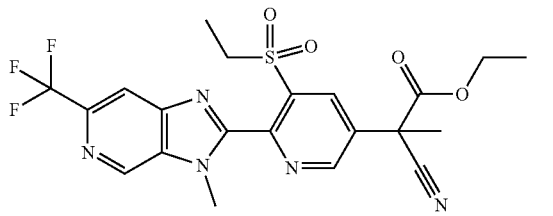

To a solution of ethyl 2-cyano-2-[5-ethylsulfonyl-6-[3-methyl-6-(trifluoromethyl)imidazo[4,5-c]pyridin-2-yl]-3-pyridyl]acetate (500 mg, 1.04 mmol, 1.00 equiv.) in DMF (6.0 mL) was added potassium carbonate (175 mg, 1.25 mmol, 1.20 equiv.) and iodomethane (78 μL, 180 mg, 1.25 mmol, 1.20 equiv.). The obtained reaction mixture was stirred at room temp. overnight. Subsequently, the reaction mixture was diluted with water (30 mL), extracted with ethyl acetate (3×30 mL) and the combined organic layers were dried over sodium sulfate, filtered and contracted under reduced pressure. The crude product was purified by flash chromatography (30% ethyl acetate/cyclohexane) to afford the title compound. LCMS (method 4): 496 (M+H)$^+$; retention time: 1.00 min.

Example P11: Preparation of 2-[3-ethylsulfanyl-4-[7-methyl-3-(trifluoromethyl)imidazo[4,5-c]pyridazin-6-yl]phenyl]-2-methyl-propanenitrile (compound P11)

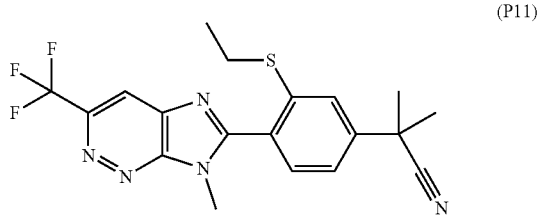 [SMILES: CCSc1cc(C(C)(C)C#N)ccc1-c1nc2cc(C(F)(F)F)nnc2n1C]

Step 1: Preparation of 4-bromo-2-ethylsulfanyl-N-[3-(methylamino)-6-(trifluoromethyl)pyridazin-4-yl]benzamide

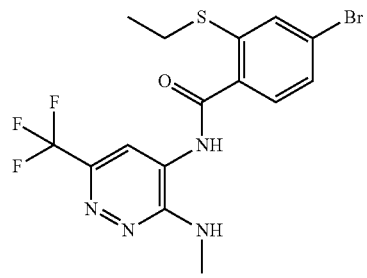 [SMILES: CCSc1cc(Br)ccc1C(=O)Nc1cc(C(F)(F)F)nnc1NC]

To a solution of N-3-methyl-6-(trifluoromethyl)pyridazine-3,4-diamine (800 mg, 4.16 mmol, 1.00 equiv.) and in tetrahydrofuran (15 mL) was added N,N-diisopropylethylamine (1.07 mL, 807 mg, 6.25 mmol, 1.50 equiv.). The reaction mixture was cooled to 0° C. and a solution of 4-bromo-2-ethylsulfanyl-benzoyl chloride (prepared according to WO2016/026848) (1.28 g, 4.58 mmol, 1.10 equiv.) in tetrahydrofuran (15 mL) was added dropwise. The reaction mixture was allowed to warm up to room temperature and stirred overnight. The reaction was slowly quenched by addition of a saturated aqueous ammonium chloride solution, and the aqueous phase was extracted three times with ethyl acetate. The combined organic phases were washed with water, brine, dried over sodium sulfate, filtered and concentrated. The crude product was purified by flash chromatography (SiO$_2$, ethyl acetate/cyclohexane) to afford the title compound. LCMS (method 1): 435 (M+H)$^+$; retention time: 1.05 min.

Step 2: Preparation of 6-(4-bromo-2-ethylsulfanyl-phenyl)-7-methyl-3-(trifluoromethyl)imidazo[4,5-c]pyridazine

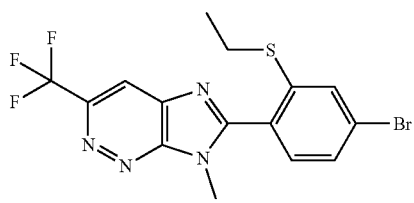 [SMILES: CCSc1cc(Br)ccc1-c1nc2cc(C(F)(F)F)nnc2n1C]

A round bottom flask equipped with reflux condenser and stir bar was charged with a solution of 4-bromo-2-ethylsulfanyl-N-[3-(methylamino)-6-(trifluoromethyl)pyridazin-4-yl]benzamide (4.40 g, 10.1 mmol, 1.00 equiv.) in glacial acetic acid (30 mL) and the reaction mixture was heated to 100° C. for 5 h. After cooling to room temp. the reaction mixture was concentrated in vacuo and remaining acetic acid was removed by repeated azeotropic distillation with toluene. The obtained crude product was purified by flash chromatography (SiO2, ethyl acetate/cyclohexane) to furnish the title compound. LCMS (method 1): 417 (M+H)$^+$; retention time: 1.09 min.

Step 3: Preparation of 2-[3-ethylsulfanyl-4-[7-methyl-3-(trifluoromethyl)imidazo[4,5-c]pyridazin-6-yl]phenyl]acetonitrile

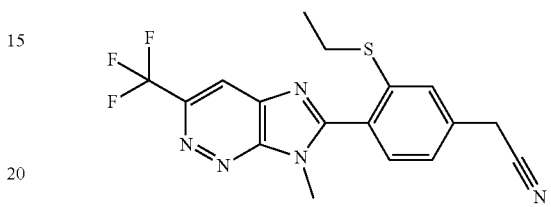

Under an argon atmosphere, a 3-neck-flask equipped with stir bar and reflux condenser was charged with a solution of 6-(4-bromo-2-ethylsulfanyl-phenyl)-7-methyl-3-(trifluoromethyl)imidazo[4,5-c]pyridazine (1.30 g, 3.12 mmol, 1.00 equiv.) in N,N-dimethylacetamide (16 mL). To this solution, trimethylsilyl acetonitrile (1.32 mL, 9.35 mmol, 3.00 equiv.), zinc fluoride (193 mg, 1.87 mmol, 0.60 equiv.), Xantphos (73.6 mg, 0.125 mmol, 0.0400 equiv.) and Pd$_2$(dba)$_3$ (44.6 mg, 0.046 mmol, 0.015 equiv.) were added. The reaction mixture was heated to 100° C. for 7 h. After cooling to room temp., the reaction mixture was diluted with ethyl acetate, filtered through a plug of Celite and washed three times with water and once with brine. The organic layers were dried over sodium sulfate, filtered and concentrated. The crude material was purified by flash column chromatography (SiO$_2$, ethyl acetate/cyclohexane) to furnish the title compound. LCMS (method 1): 378 (M+H)$^+$; retention time: 0.96 min.

Step 4: Preparation of 2-[3-ethylsulfanyl-4-[7-methyl-3-(trifluoromethyl)imidazo[4,5-c]pyridazin-6-yl]phenyl]-2-methyl-propanenitrile (compound P11)

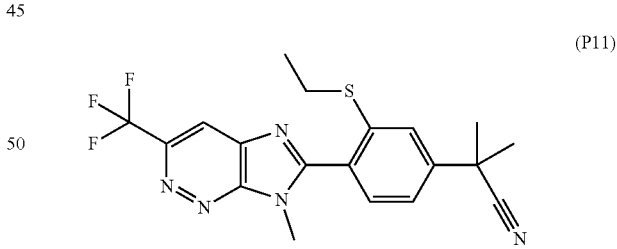

A solution of 2-[3-ethylsulfanyl-4-[7-methyl-3-(trifluoromethyl)imidazo[4,5-c]pyridazin-6-yl]phenyl]acetonitrile (192 mg, 0.509 mmol, 1.00 equiv.) in N,N-dimethylformamide (4 mL) under argon atmosphere was cooled to at 0° C. At this temperature, sodium hydride (60 wt-% in mineral oil, 273 mg, 0.712 mmol, 1.40 equiv.) was added portionwise. The deep red reaction mixture was stirred at 0° C. for 30 min. The obtained mixture was added via syringe to a solution of methyl iodide (44 μl, 101 mg, 0.712 mmol, 1.40 equiv.) in DMF (4 mL) under argon at 0° C. The resulting mixture was slowly warmed up to room temperature and stirred overnight. The mixture was then poured slowly into a saturated aqueous ammonium chloride solution, and the aqueous phase was extracted with ethyl acetate. The organic phase was washed four times with water then brine, dried over sodium sulfate, filtered and concentrated. The crude material was purified by column chromatography over silica gel, eluting with ethyl acetate in cyclohexane to yield the title compound. LCMS (method 1): 406 (M+H)$^+$; retention time: 1.03 min.

Example P12: Preparation of 2-[3-ethylsulfonyl-4-[7-methyl-3-(trifluoromethyl)imidazo[4,5-c]pyridazin-6-yl]phenyl]-2-methyl-propanenitrile (compound P12)

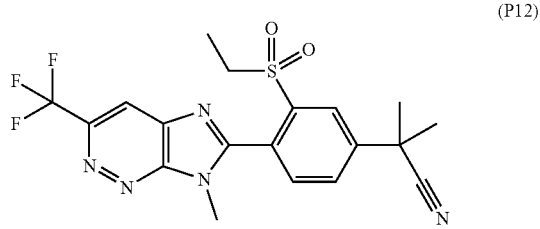 [SMILES: CCS(=O)(=O)c1cc(C(C)(C)C#N)ccc1-c1nc2cc(C(F)(F)F)nnc2n1C]

(P12)

To a solution of 2-[3-ethylsulfanyl-4-[7-methyl-3-(trifluoromethyl)imidazo[4,5-c]pyridazin-6-yl]phenyl]-2-methyl-propanenitrile (compound P11) (74.0 mg, 0.183 mmol, 1.00 equiv.) in dichloromethane (2.0 mL) was added 3-chloroperbenzoic acid (75 wt-%, 92.4 mg, 0.384 mmol, 2.10 equiv) at room temperature. Stirring was continued for 18 h at room temperature before addition of a saturated solution of sodium thiosulfate (10 mL) and saturated NaHCO$_3$ (10 mL). The reaction mixture was diluted with dichloromethane (50 mL), and the mixture was stirred for 20 min. After separation of the aqueous layer, extraction with dichloromethane (3×20 mL), the combined organic layers were washed with water and brine, dried (Na$_2$SO$_4$), and concentrated under reduced pressure. The obtained crude material was purified by flash chromatography (SiO$_2$, ethyl acetate/cyclohexane) to furnish the title compound. LCMS (method 1): 438 (M+H)$^+$; retention time: 0.93 min.

Example P15: Preparation of 2-[5-ethylsulfonyl-6-[3-methyl-6-(trifluoromethyl)imidazo[4,5-c]pyridin-2-yl]-3-pyridyl]-2,2-difluoro-acetonitrile (compound P15)

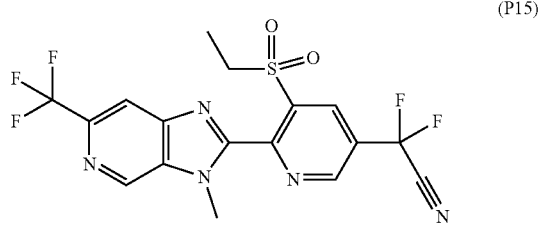 [SMILES: CCS(=O)(=O)c1cc(C(F)(F)C#N)cnc1-c1nc2cc(C(F)(F)F)ncc2n1C]

(P15)

To a solution of 2-[5-ethylsulfonyl-6-[3-methyl-6-(trifluoromethyl)imidazo[4,5-c]pyridin-2-yl]-3-pyridyl]acetonitrile (see example P3, step 1) (409 mg, 1.00 mmol, 1.00 equiv.) in tetrahydrofuran (6.0 mL), was added Cs$_2$CO$_3$ (391 mg, 1.20 mmol, 1.00 equiv.) followed by N-Fluorobenzenesulfonimide (315 mg, 1.00 mmol, 1.00 equiv.) under nitrogen. The reaction mixture was stirred at room temp. for 1 h. The obtained reaction mixture was diluted ethyl acetate (30 mL) and water (30 mL). After extraction with ethyl acetate (3×30 mL), the combined organic layers were washed with water (2×30 mL) and dried with sodium sulfate. Concentration under reduced pressure and purification by flash chromatography (SiO$_2$, ethyl acetate/cyclohexane) furnished the title compound as a white solid. LCMS (method 4): 446 (M+H)$^+$; retention time: 1.05 min.

Example P16: Preparation of 2-[3-ethylsulfanyl-4-[3-methyl-6-(trifluoromethyl)imidazo[4,5-c]pyridin-2-yl]phenyl]-2-methyl-propanenitrile (compound P16)

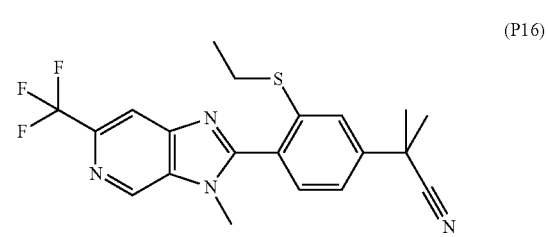 [SMILES: CCSc1cc(C(C)(C)C#N)ccc1-c1nc2cc(C(F)(F)F)ncc2n1C]

(P16)

A microwave vial was charged with 2-(4-bromo-2-ethylsulfanyl-phenyl)-3-methyl-6-(trifluoromethyl)imidazo[4,5-c]pyridine (prepared according to WO2016/026848) (500 mg, 1.20 mmol, 1.00 equiv.), rac-BINAP (77.1 mg, .0120 mmol, 0.10 equiv.), and Pd$_2$(dba)$_3$ (56.7 mg, 0.0600 mmol, 0.0500 equiv.). After flushing with argon, tetrahydrofuran (THF) (1.20 mL) and cyclopentylmethylether (CPME) (1.20 mL) followed by isobutyronitrile (119 μL, 91.7 mg, 1.32 mmol, 1.10 equiv.) were added. The vial was capped under argon atmosphere and the obtained solution was cooled to −25° C. After stirring for 25 min, LiHMDS (1M solution in THF, 1.32 mL, 1.32 mmol, 1.10 equiv.) was added dropwise over 5 min. The obtained solution was allowed to warm to room temperature before heating to 80° C. for 4 h. After cooling to room temp. the reaction mixture was quenched with water, filtered through a plug of celite and rinsed with ethyl acetate. The aqueous layer was extracted with ethyl acetate (3×), and the combined organic layers were washed with water and brine. Drying over sodium sulfate, filtration and concentration in vacuo furnished the crude material which was purified by flash chromatography (SiO$_2$, ethyl acetate/cyclohexane) to furnish the title compound. LCMS (method 1): 405 (M+H)$^+$; retention time: 1.02 min.

Example P17: Preparation of 2-[3-ethylsulfonyl-4-[3-methyl-6-(trifluoromethyl)imidazo[4,5-c]pyridin-2-yl]phenyl]-2-methyl-propanenitrile (compound P17)

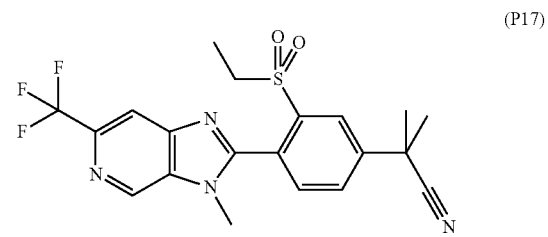 [SMILES: CCS(=O)(=O)c1cc(C(C)(C)C#N)ccc1-c1nc2cc(C(F)(F)F)ncc2n1C]

(P17)

To a solution of 2-[3-ethylsulfanyl-4-[3-methyl-6-(trifluoromethyl)imidazo[4,5-c]pyridin-2-yl]phenyl]-2-methyl-propanenitrile (compound P16) (88.8 mg, 0.220 mmol, 1.00 equiv.) in dichloromethane (1.0 mL) was added 3-chloroperbenzoic acid (75 wt-%, 103 mg, 0.461 mmol, 2.10 equiv) at room temperature. Stirring was continued for 18 h at room temperature before addition of a saturated solution of sodium thiosulfate (5 mL) and saturated NaHCO₃ (5 mL). The reaction mixture was diluted with dichloromethane (15 mL), and the mixture was stirred for 20 min. After separation of the aqueous layer, extraction with dichloromethane (3×10 mL), the combined organic layers were washed with water and brine, dried (Na₂SO₄), and concentrated under reduced pressure. The obtained crude material was purified by flash chromatography (SiO₂, MeOH/dichloromethane) to furnish the title compound. LCMS (method 1): 437 (M+H)$^+$; retention time: 0.90 min.

Example P19: Preparation of 2-[6-(6-bromo-3-methyl-imidazo[4,5-c]pyridin-2-yl)-5-ethylsulfonyl-3-pyridyl]-2-methyl-propanenitrile (compound P19)

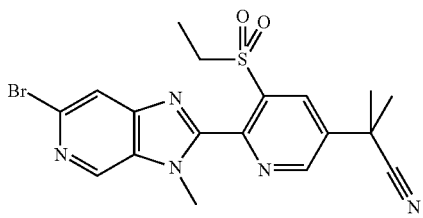

(P19)

Step 1: Preparation of methyl 5-(1-cyano-2-ethoxy-2-oxo-ethyl)-3-ethylsulfanyl-pyridine-2-carboxylate

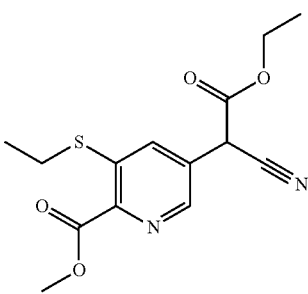

To a solution of methyl 5-bromo-3-ethylsulfanyl-pyridine-2-carboxylate (prepared according to WO2017/055147) (32.0 g, 116 mmol, 1.00 equiv.) in DMSO (350 mL) was added ethyl 2-cyanoacetate (18.5 mL, 19.7 g, 174 mmol, 1.50 equiv.), K₂CO₃ (40.4 g, 290 mmol, 2.50 equiv.) and tetrabutylammonium bromide (3.81 g, 11.6 mmol, 0.100 equiv.). The resulting suspension was heated to 90° C. overnight. After cooling to room temp., the reaction mixture was diluted with water (150 mL) and ethyl acetate (300 mL) and cooled to 0° C. To the stirred mixture, 2M HCl (200 mL) was added slowly (exothermic reaction) until pH 4-5 was reached. The aqueous layer was separated and extracted with ethyl acetate (3×500 mL). The combined organic layers were dried over sodium sulfate and concentrated in vacuo to obtain the crude material. Recrystallization from ethanol furnished the title compound as a tan solid. LCMS (method 1): 309 (M+H)$^+$; retention time: 0.86 min.

Step 2: Preparation of methyl 5-(cyanomethyl)-3-ethylsulfanyl-pyridine-2-carboxylate

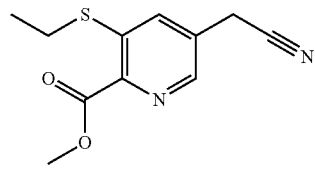 [SMILES: CCSc1cc(CC#N)cnc1C(=O)OC]

In a 3-neck-flask equipped with magnetic stir bar and reflux condenser and gas exhaust, to a solution of methyl 5-(1-cyano-2-ethoxy-2-oxo-ethyl)-3-ethylsulfanyl-pyridine-2-carboxylate (21.1 g, 68.4 mmol, 1.00 equiv.) in DMSO (210 mL) was first added sodium chloride (40.0 g, 684 mmol, 10.0 equiv.) followed by water (105 mL). The reaction mixture was heated to 125° C. internal temperature at which temperature strong gas evolution set in. Stirring was continued for 3 h. After cooling to room temp. the reaction mixture was diluted with water (50 mL) and ethyl acetate (100 mL) was added. The aqueous layer was separated, extracted with ethyl acetate (3×200 mL) and the combined organic layers were washed with water, dried (Na₂SO₄) and concentrated in vacuo to afford the crude material. The crude product was directly used as obtained. LCMS (method 1): 237 (M+H)$^+$; retention time: 0.72 min Step 3: Preparation of 5-(1-cyano-1-methyl-ethyl)-3-ethylsulfanyl-pyridine-2-carboxylic acid

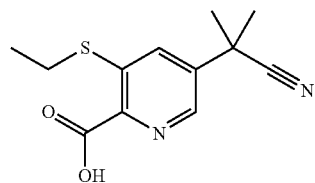 [SMILES: CCSc1cc(C(C)(C)C#N)cnc1C(=O)O]

To a solution of methyl 5-(cyanomethyl)-3-ethylsulfanyl-pyridine-2-carboxylate (20.0 g, 84.6 mmol, 1.00 equiv.) in 1,4-dioxane (170 mL) was added benzyltrimethylammonium chloride (998 mg, 4.23 mmol, 0.0500 equiv.) and the obtained solution was cooled to 0° C. This this solution, aqueous NaOH (30 wt %, 59 mL, 590 mmol, 7.0 equiv.) was added slowly followed by dropwise addition of iodomethane (10.5 mL, 24.0 g, 169 mmol, 2.00 equiv.) while maintaining the temperature between 0 and 5° C. Stirring at 0° C. was continued for 5 h before quenching the reaction mixture by slow addition of 2M HCl until pH 5 was reached. After addition of ethyl acetate (250 mL) and stirring for 30 min, the layers were separated and the aqueous layer was extracted with ethyl acetate (3×100 mL). The combined organic layers were washed with water (50 mL) and brine (50 mL), dried (Na₂SO₄) and evaporated. The crude material was purified by flash chromatography (SiO₂, ethyl acetate/cyclohexane) to furnish the title compound. LCMS (method 1): 251 (M+H)$^+$; retention time: 0.71 min.

Step 4: Preparation of N-[2-bromo-5-(methylamino)-4-pyridyl]-5-(1-cyano-1-methyl-ethyl)-3-ethylsulfanyl-pyridine-2-carboxamide

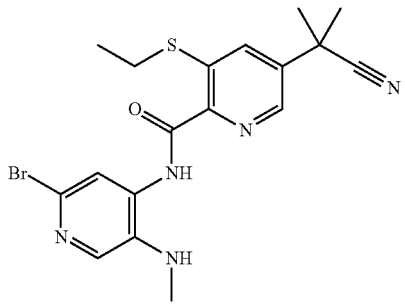 [SMILES: CCSc1cc(C(C)(C)C#N)cnc1C(=O)Nc1cc(Br)ncc1NC]

To a solution of 5-(1-cyano-1-methyl-ethyl)-3-ethylsulfanyl-pyridine-2-carboxylic acid (10.0 g, 40.0 mmol, 1.00 equiv.) and a catalytic amount of N,N-dimethylformamide in dichloromethane (24 mL) under argon was added oxalyl chloride (5.23 mL, 7.61 g, 59.9 mmol, 1.50 equiv.) dropwise via syringe. The reaction mixture was then heated to reflux for 3 h. After cooling to room temperature, the reaction mixture was evaporated to dryness. The resulting brown oil was dissolved in THF (190 mL) and slowly added at 0° C. via dropping funnel to a solution of 6-bromo-N3-methyl-pyridine-3,4-diamine (prepared according to WO2016/107831) (8.43 g, 41.7 mmol, 1.04 equiv.) and N,N-diisopropylethylamine (16.7 mL, 12.4 g, 94.9 mmol, 2.54 equiv.) in THF (300 mL). The reaction was allowed to warm to room temp. and stirring was continued for 20 h. The reaction was slowly quenched by addition of a saturated aqueous ammonium chloride solution, and the aqueous phase was extracted with ethyl acetate. The combined organic phases were washed with water, brine, dried over sodium sulfate, filtered and concentrated to furnish the title compound as a crude product. LCMS (method 1): 434 (M+H)$^+$; retention time: 0.82 min.

Step 5: Preparation of 2-[6-(6-bromo-3-methyl-imidazo[4,5-c]pyridin-2-yl)-5-ethylsulfanyl-3-pyridyl]-2-methyl-propanenitrile (compound P23)

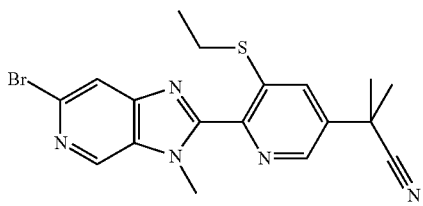

A round bottom flask equipped with reflux condenser and stir bar was charged with a solution of N-[2-bromo-5-(methylamino)-4-pyridyl]-5-(1-cyano-1-methyl-ethyl)-3-ethylsulfanyl-pyridine-2-carboxamide (13.0 g, 29.9 mmol, 1.00 equiv) in glacial acetic acid (90 mL) and the reaction mixture was heated to 100° C. for 5 h. After cooling to room temp. the reaction mixture was concentrated in vacuo and remaining acetic acid was removed by repeated azeotropic distillation with toluene. The obtained crude product was purified by flash chromatography (SiO$_2$, ethyl acetate/cyclohexane) to furnish the title compound. LCMS (method 1): 416 (M+H)$^+$; retention time: 0.94 min.

Step 6: Preparation of 2-[6-(6-bromo-3-methyl-imidazo[4,5-c]pyridin-2-yl)-5-ethylsulfonyl-3-pyridyl]-2-methyl-propanenitrile (compound P19)

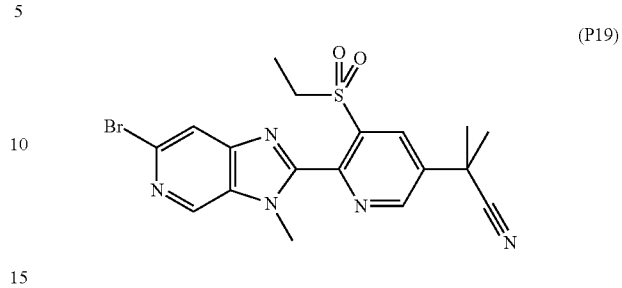

To a solution of 2-[6-(6-bromo-3-methyl-imidazo[4,5-c]pyridin-2-yl)-5-ethylsulfanyl-3-pyridyl]-2-methyl-propanenitrile (compound P23) (7.10 g, 17.1 mmol, 1.00 equiv.) in dichloromethane (171 mL) was added 3-chloroperbenzoic acid (75 wt-%, 8.04 g, 35.0 mmol, 2.05 equiv) in small portions (exothermic reaction) at 0° C. The reaction mixture was allowed to warm to room temperature and stirring was continued for 18 h at room temperature before addition of a saturated solution of sodium thiosulfate (100 mL) and saturated NaHCO$_3$ (100 mL). The reaction mixture was diluted with dichloromethane (150 mL), and the mixture was stirred for 20 min. After separation of the aqueous layer, extraction with dichloromethane (3×10 mL), the combined organic layers were washed with of saturated sodium thiosulfate (50 mL), saturated NaHCO$_3$ (50 mL), followed by water (50 mL) and brine (50 mL). Drying (Na$_2$SO$_4$) and concentration under reduced pressure yielded a crude material which was purified by flash chromatography (SiO$_2$, MeOH/dichloromethane) to furnish the title compound. LCMS (method 1): 448 (M+H)$^+$; retention time: 0.88 min.

Example P20: Preparation of 2-[5-ethylsulfonyl-6-[3-methyl-6-(1,1,2,2,2-pentafluoroethyl)imidazo[4,5-c]pyridin-2-yl]-3-pyridyl]-2-methyl-propanenitrile (compound P20)

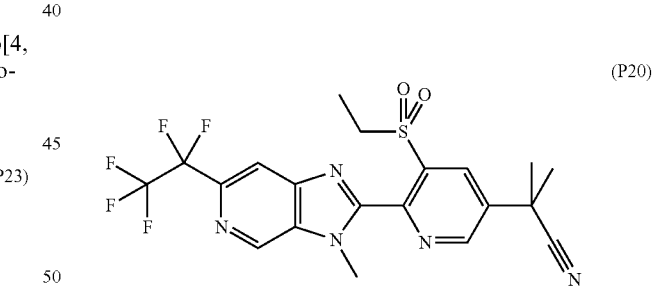

Step 1: Preparation of 2-[5-ethylsulfonyl-6-(6-iodo-3-methyl-imidazo[4,5-c]pyridin-2-yl)-3-pyridyl]-2-methyl-propanenitrile (compound P22)

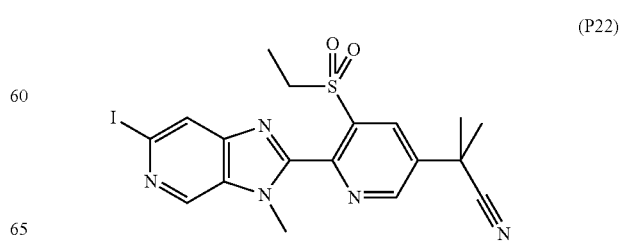

To a solution of 2-[6-(6-bromo-3-methyl-imidazo[4,5-c]pyridin-2-yl)-5-ethylsulfonyl-3-pyridyl]-2-methyl-propanenitrile (compound P19) (1.00 g, 2.23 mmol, 1.00 equiv.) in 1,4-dioxane (11 mL) was added NaI (689 mg, 4.46 mmol, 2.00 equiv.), CuI (224 mg, 1.12 mmol, 0500 equiv.) and N,N'-dimethylethylendiamine (DMEDA) (0.29 mL, 0.24 g, 2.7 mmol, 1.2 equiv.). The reaction mixture was heated to 100° C. for 40 h. After cooling to room temperature, the reaction mixture was diluted with ethyl acetate (50 mL) and a 1M aqueous solution of NH$_3$ was added. The aqueous layer was separated and extracted with ethyl acetate (2×20 mL). The combined organic layers were washed with sat. NaHCO$_3$, water and brine, and dried (Na$_2$SO$_4$). Concentration under reduced pressure furnished the title compound. LCMS (method 1): 496 (M+H)$^+$; retention time: 0.90 min.

Step 2: Preparation of 2-[5-ethylsulfonyl-6-[3-methyl-6-(1,1,2,2,2-pentafluoroethyl)imidazo[4,5-c]pyridin-2-yl]-3-pyridyl]-2-methyl-propanenitrile (compound P20)

(P20)

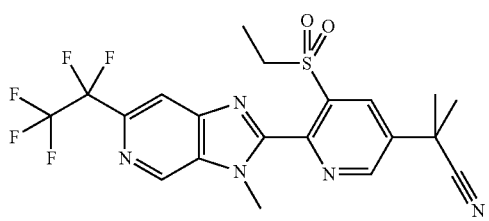

To a solution of 2-[5-ethylsulfonyl-6-(6-iodo-3-methyl-imidazo[4,5-c]pyridin-2-yl)-3-pyridyl]-2-methyl-propanenitrile (compound P22) (900 mg, 1.82 mmol, 1.00 equiv.) in DMF (6.5 mL) under an argon atmosphere was added (phen)CuC$_2$F$_5$ [1360806-59-2]. The stirred reaction mixture was heated to 90° C. for 2 h. After cooling to room temperature, the reaction mixture filtered over Celite and rinsed with ethyl acetate. The filtrate was washed with 28% aqueous ammonia (20 mL), sat. NaHCO$_3$ (20 mL), water (20 mL) and brine (20 mL). Drying over sodium sulfate, filtration and concentration under reduced pressure furnished the crude product. Purification by flash chromatography (SiO$_2$, ethyl acetate/cyclohexane) yielded the title compound as a white solid. LCMS (method 1): 488 (M+H)$^+$; retention time: 1.00 min.

Example P23: Preparation of 2-[5-ethylsulfanyl-6-[3-methyl-6-(trifluoromethyl)imidazo[4,5-c]pyridin-2-yl]-3-pyridyl]-2-methyl-propanenitrile (compound P23)

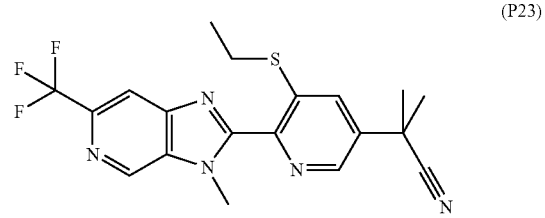

(P23)

A three-neck flask equipped with dropping funnel and argon inlet was charged with isobutyronitrile (4.30 mL, 3.31 g, 47.9 mmol, 2.00 equiv) and cooled to −25° C. At this temperature, LiHMDS (1.0M solution in THF, 72 mL, 64 g, 72 mmol, 3.0 equiv.) was added dropwise over 30 min while the stirred reaction mixture was kept at −25° C. Stirring at this temperature was continued for another 15 min. The obtained solution was then added dropwise to a stirred solution of 2-(5-bromo-3-ethylsulfanyl-2-pyridyl)-3-methyl-6-(trifluoromethyl)imidazo[4,5-c]pyridine (prepared according to WO2016/026848) (10.0 g, 24.0 mmol, 1.00 equiv.) in THF (50 mL) at −25° C. over a period of 1.5 h. Stirring at this temperature was continued for an additional 30 min before allowing to warm up to room temperature. After further 1 h at this temperature, the reaction mixture was quenched by slow addition of water (50 mL) and ethyl acetate (100 mL). The aqueous layer was separated and extracted with ethyl acetate (2×50 mL) and the combined organic layers were washed with brine and dried over sodium sulfate. Concentration in vacuo and purification by flash chromatography furnished the desired title compound. LCMS (method 1): 406 (M+H)$^+$; retention time: 0.99 min.

TABLE 4

Examples of compounds of formula (I)

| Compound No. | IUPAC Name | Structure | Melting Point | MS/NMR |
|---|---|---|---|---|
| P1 | 2-[5-ethylsulfonyl-6-[3-methyl-6-(trifluoromethyl)imidazo[4,5-c]pyridin-2-yl]-3-pyridyl]-2-methyl-propanedinitrile | 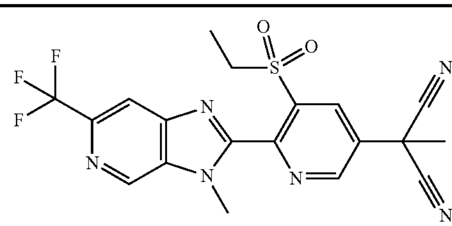 | 222-223 | LCMS (method 1): 449 (M+H)$^+$; retention time: 0.95 min |
| P2 | 2-[5-ethylsulfonyl-6-[7-methyl-6-(trifluoromethyl(imidazo[4,5-c]pyridazin-6-yl]-3-pyridil]-2-methyl-propanenitrile | 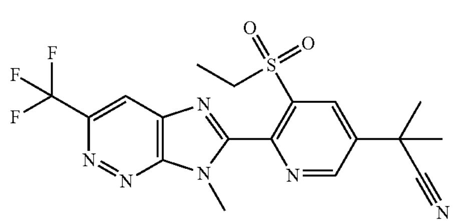 [SMILES: CCS(=O)(=O)c1cc(C(C)(C)C#N)cnc1-c1nc2cc(C(F)(F)F)nnc2n1C] | 214-215 | LCMS (method 1): 439 (M+H)$^+$; retention time: 0.93 min |

TABLE 4-continued

Examples of compounds of formula (I)

| Compound No. | IUPAC Name | Structure | Melting Point | MS/NMR |
|---|---|---|---|---|
| P3 | 2-ethyl-2-[5-ethylsulfonyl-6-[3-methyl-6-(trifluoromethyl)imidazo[4,5-c]pyridin-2-yl]-3-pyridyl]butanenitrile | 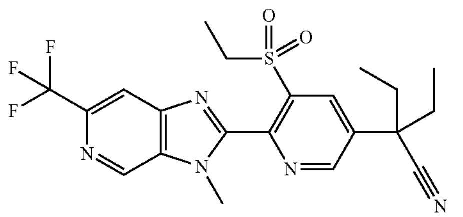 [SMILES: CCC(C#N)(CC)c1cnc(-c2nc3cc(C(F)(F)F)ncc3n2C)c(S(=O)(=O)CC)c1] | 217-218 | LCMS (method 1): 466 (M+H)+; retention time: 1.02 min |
| P4 | 2-[5-ethylsulfonyl-6-[3-methyl-6-(trifluoromethyl)imidazo[4,5-c]pyridin-2-yl]-3-pyridyl]butanenitrile | 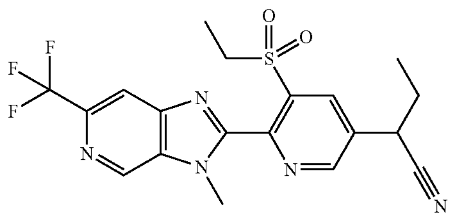 [SMILES: CCC(C#N)c1cnc(-c2nc3cc(C(F)(F)F)ncc3n2C)c(S(=O)(=O)CC)c1] | 201-202 | LCMS (method 1): 438 (M+H)+; retention time: 0.94 min |
| P5 | 2[5-ethylsulfonyl-6-[3-methyl-6-(trifluoromethyl)imidazo[4,5-c]pyridin-2-yl]-3-pyridyl]-2-methyl-propanenitrile | 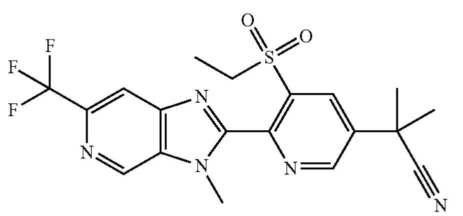 [SMILES: CCS(=O)(=O)c1cc(C(C)(C)C#N)cnc1-c1nc2cc(C(F)(F)F)ncc2n1C] | 225-226 | LCMS (method 1): 438 (M+H)+; retention time: 0.93 min |
| P6 | 2-[5-ethylsulfonyl-6-[3-methyl-6-(trifluoromethyl)imidazo[4,5-c]pyridin-2-yl]-3-pyridyl]propanenitrile | 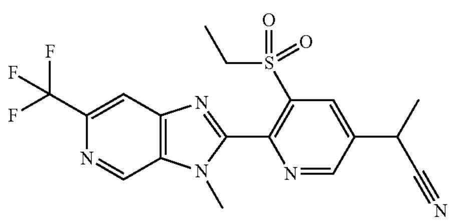 | 223-224 | LCMS (method 1): 424 (M+H)+; retention time: 1.32 min |
| P7 | 2-[5-ethylsulfanyl-6-[3-methyl-6-(trifluoromethyl)imidazo[4,5-c]pyridin-2-yl]-3-pyridyl]propanedinitrile | 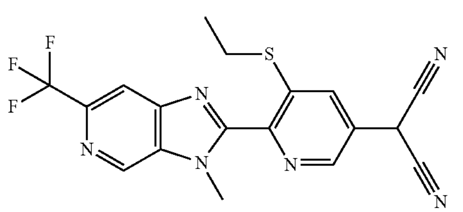 [SMILES: CCSc1cc(C(C#N)C#N)cnc1-c1nc2cc(C(F)(F)F)ncc2n1C] | | LCMS (method 1): 403 (M+H)+; retention time: 0.86 min |
| P8 | 2-[5-ethylsulfanyl-6-[3-methyl-6-(trifluoromethyl)imidazo[4,5-c]pyridin-2-yl]-3-pyridyl]-2-methyl-propanedinitrile | 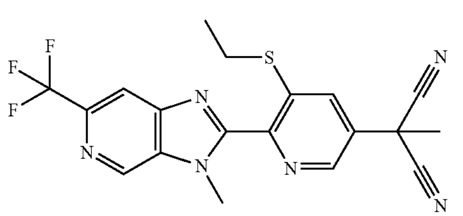 [SMILES: CCSc1cc(C(C)(C#N)C#N)cnc1-c1nc2cc(C(F)(F)F)ncc2n1C] | | LCMS (method 1): 417 (M+H)+; retention time: 1.01 min |
| P9 | ethyl 2-cyano-2-[5-ethylsulfonyl-6-[3-methyl-6-(trifluoromethyl)imidazo[4,5-c]pyridin-2-yl]-3-pyridyl]propanoate | 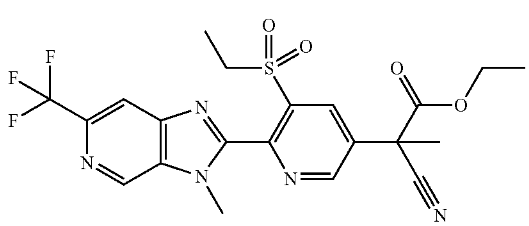 [SMILES: CCOC(=O)C(C)(C#N)c1cnc(-c2nc3cc(C(F)(F)F)ncc3n2C)c(S(=O)(=O)CC)c1] | | LCMS (method 4): 496 (M+H)+; retention time: 1.00 min. |

TABLE 4-continued

Examples of compounds of formula (I)

| Compound No. | IUPAC Name | Structure | Melting Point | MS/NMR |
|---|---|---|---|---|
| P10 | 2-[5-ethylsulfonyl-6-[3-methyl-6-(trifluoromethyl)imidazo[4,5-c]pyridin-2-yl]-3-pyridyl]-3-methyl-butanenitrile | 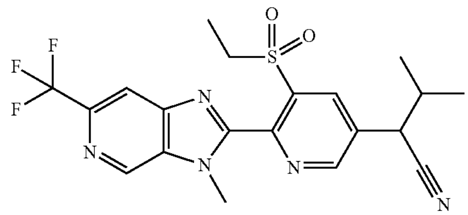 [SMILES: CCS(=O)(=O)c1cc(C(C#N)C(C)C)cnc1-c1nc2cc(C(F)(F)F)ncc2n1C] | 182-183 | LCMS (method 1): 452 (M+H)+; retention time: 0.98 min. |
| P11 | 2-[3-ethylsulfanyl-4-[7-methyl-3-(trifluoromethyl)imidazo[4,5-c]pyridazin-6-yl]phenyl]9-2-methyl-propanenitrile | 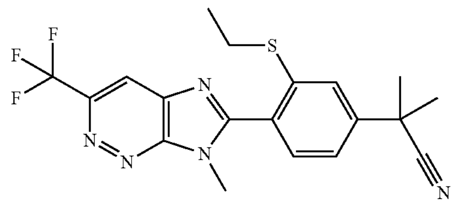 | | LCMS (method 1): 406 (M+H)+; retention time: 1.03 min |
| P12 | 2-[3-ethylsulfonyl-4-[7-methyl-3-(trifluoromethyl)imidazo[4,5-c]pyridazin-6-yl]phenyl]-2-methyl-propanenitrile | 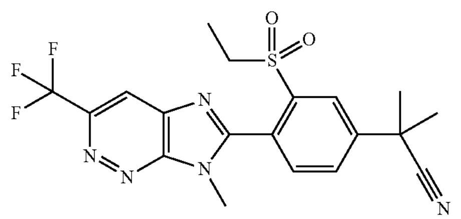 | 204-205 | LCMS (method 1): 438 (M+H)+; retention time: 0.93 min |
| P13 | 2-[3-ethylsulfanyl-4-[7-methyl-3-(trifluoromethyl)imidazo[4,5-c]pyridazin-6-yl]phenyl]propanenitrile | 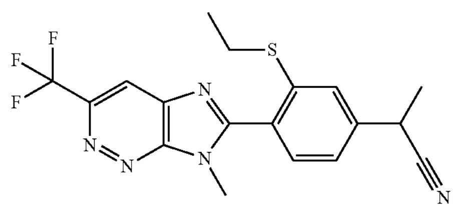 | | LCMS (method 2): 424 (M+H)+; retention time: 1.32 min |
| P14 | 2-[3-ethylsulfonyl-4-[7-methyl-3-(trifluoromethyl)imidazo[4,5-c]pyridazin-6-yl]phenyl]propanenitrile | 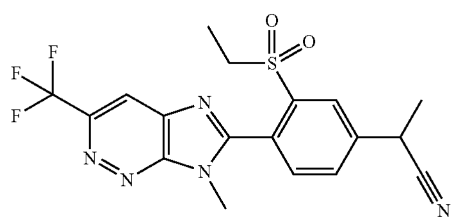 | | LCMS (method 2): 392 (M+H)+; retention time: 1.58 min |
| P15 | 2-[5-ethylsulfonyl-6-[3-methyl-6-(trifluoromethyl)imidazo[4,5-c]pyridin-2-yl]-3-pyridyl]-2,2-difluoro-acetonitrile | 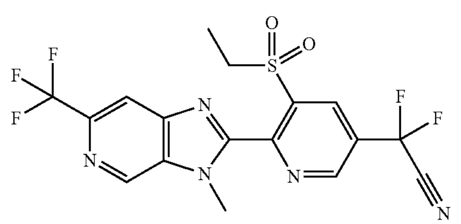 [SMILES: CCS(=O)(=O)c1cc(C(F)(F)C#N)cnc1-c1nc2cc(C(F)(F)F)ncc2n1C] | 208-210 | LCMS (method 4): 446 (M+H)+; retention time: 1.05 min |
| P16 | 2-[3-ethylsulfanyl-4-[3-methyl-6-(trifluoromethyl)imidazo[4,5-c]pyridin-2-yl]phenyl]-2-methyl-propanenitrile | 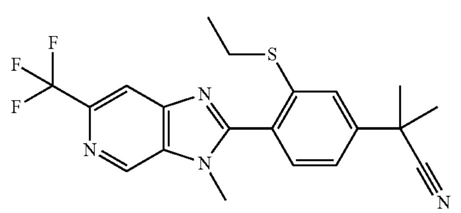 [SMILES: CCSc1cc(C(C)(C)C#N)ccc1-c1nc2cc(C(F)(F)F)ncc2n1C] | 157-158 | LCMS (method 1): 405 (M+H)+; retention time: 1.02 min |

TABLE 4-continued

Examples of compounds of formula (I)

| Compound No. | IUPAC Name | Structure | Melting Point | MS/NMR |
|---|---|---|---|---|
| P17 | 2-[3-ethylsulfonyl-4-[3-methyl-6-(trifluoromethyl)imidazo[4,5-c]pyridin-2-yl]phenyl]-2-methyl-propanenitrile | 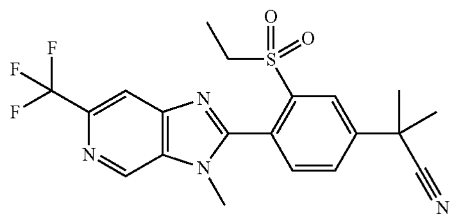 [SMILES: CCS(=O)(=O)c1cc(C(C)(C)C#N)ccc1-c1nc2cc(C(F)(F)F)ncc2n1C] | 218-219 | LCMS (method 1): 437 (M+H)+; retention time: 0.90 min |
| P18 | 2-[5-ethylsulfonyl-6-[3-methyl-6-(trifluoromethyl)imidazo[4,5-c]pyridin-2-yl]-3-pyridyl]-2-fluoro-propanenitrile | 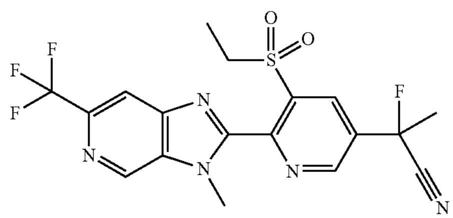 [SMILES: CCS(=O)(=O)c1cc(C(C)(F)C#N)cnc1-c1nc2cc(C(F)(F)F)ncc2n1C] | 202-204 | LCMS (method 4): 442 (M+H)+; retention time: 0.98 min |
| P19 | 246-(6-bromo-3-methyl-imidazo[4,5-c]pyridin-2-yl)-5-ethylsulfonyl-3-pyridyl]-2-methyl-propanenitrile | 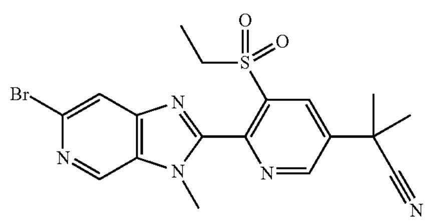 [SMILES: CCS(=O)(=O)c1cc(C(C)(C)C#N)cnc1-c1nc2cc(Br)ncc2n1C] | 261-262 | LCMS (method 1): 448 (M+H)+; retention time: 0.88 min |
| P20 | 2-[5-ethylsulfonyl-6-[3-methyl-6-(1,1,2,2,2-pentafluoroethyl)imidazo[4,5-c]pyridin-2-yl]-3-pyridyl]-2-methyl-propanenitrile | 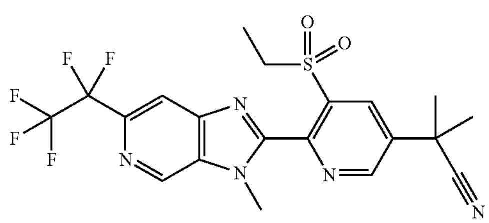 [SMILES: CCS(=O)(=O)c1cc(C(C)(C)C#N)cnc1-c1nc2cc(C(F)(F)C(F)(F)F)ncc2n1C] | 212-213 | LCMS (method 1): 488 (M+H)+; retention time: 1.00 min |
| P21 | ethyl 2-cyano-2-[5-ethylsulfanyl-6-[3-methyl-6-(trifluoromethyl)imidazo[4,5-c]pyridin-2-yl]-3-pyridyl]propanoate | 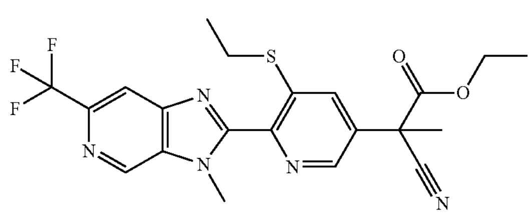 [SMILES: CCOC(=O)C(C)(C#N)c1cnc(-c2nc3cc(C(F)(F)F)ncc3n2C)c(SCC)c1] | | LCMS (method 1): 464 (M+H)+; retention time: 1.05 min |
| P22 | 2-[5-ethylsulfonyl-6-(6-iodo-3-methyl-imidazo[4,5-c]pyridin-2-yl)-3-pyridyl[-2-methyl-propanenitrile | 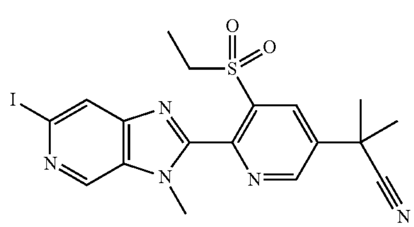 [SMILES: CCS(=O)(=O)c1cc(C(C)(C)C#N)cnc1-c1nc2cc(I)ncc2n1C] | | LCMS (method 1): 496 (M+H)+; retention time: 0.90 min |
| P23 | 2-[6-(6-bromo-3-methyl-imidazo[4,5-c]pyridin-2-yl)-5-ethylsulfanyl-3-pyridyl]-2-methyl-propanenitrile | 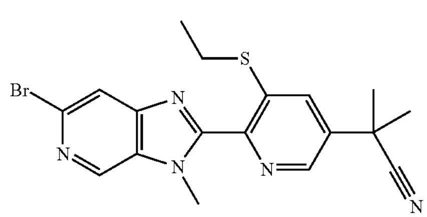 [SMILES: CCSc1cc(C(C)(C)C#N)cnc1-c1nc2cc(Br)ncc2n1C] | | LCMS (method 1): 416 (M+H)+l retention time: 0.94 min |

TABLE 4-continued

Examples of compounds of formula (I)

| Compound No. | IUPAC Name | Structure | Melting Point | MS/NMR |
|---|---|---|---|---|
| P24 | 2-[5-ethylsulfanyl-6-[3-methyl-6-(trifluoromethyl)imidazo[4,5-c]pyridin-2-yl]-3-pyridyl-2-methyl-propanenitrile | 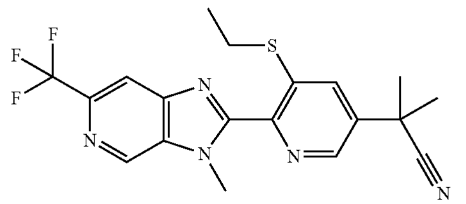 [SMILES: CCSc1cc(C(C)(C)C#N)cnc1-c1nc2cc(C(F)(F)F)ncc2n1C] | | LCMS (method 1): 406 (M+H)⁺; retention time: 0.99 min |
| P25 | ethyl 2-cyano-2-]5-ethylsulfonyl-6-]3-methyl-6-(trifluoromethyl)imidazo[4,5-c]pyridin-2-yl]-3-pyridyl]acetate | 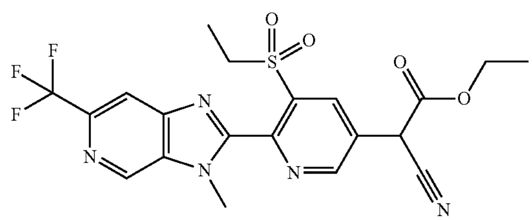 | | LCMS (method 4): 482 (M+H)⁺; retention time: 0.95 min |
| P26 | 2-[5-ethylsulfanyl-6-[7-methyl-3-(trifluoromethyl)imidazo[4,5-c]pyridazin-6-yl]-3-pyridyl]-2-methyl-propanenitrile | 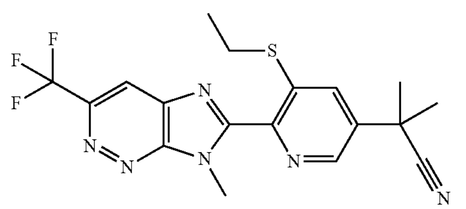 [SMILES: CCSc1cc(C(C)(C)C#N)cnc1-c1nc2cc(C(F)(F)F)nnc2n1C] | | LCMS (method 1): 407 (M+H)⁺; retention time: 1.01 min |

TABLE I1

Examples of novel intermediate compounds of formula (XVI), (XIV), (XII), (XI), (XIII), (IX), and (II):

| Compound No. | IUPAC Name | Structure | Melting Point | MS/NMR |
|---|---|---|---|---|
| XVI-1 | 5-(1-cyano-1-methyl-ethyl)-3-ethylsulfonyl-pyridine-2-carboxylic acid | 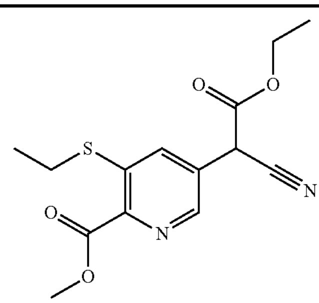 | | LCMS (method 1): 309 (M + H)⁺; retention time: 0.85 min |
| XVI-2 | methyl 4-(1-cyano-2-ethoxy-2-oxo-ethyl)-2-ethylsulfanyl-benzoate | 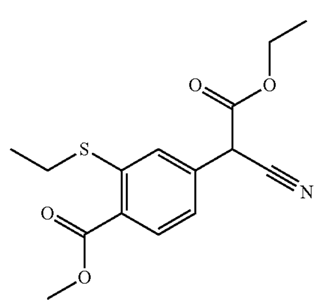 [SMILES: CCOC(=O)C(C#N)c1ccc(C(=O)OC)c(SCC)c1] | | LCMS (method 1): 308 (M + H)⁺; retention time: 0.98 min |

TABLE I1-continued

Examples of novel intermediate compounds of formula (XVI), (XIV), (XII), (XI), (XIII), (IX), and (II):

| Compound No. | IUPAC Name | Structure | Melting Point | MS/NMR |
|---|---|---|---|---|
| XVI-3 | methyl 4-(1-cyano-2-ethoxy-2-oxo-methyl)-2-ethylsulfanyl-benzoate | 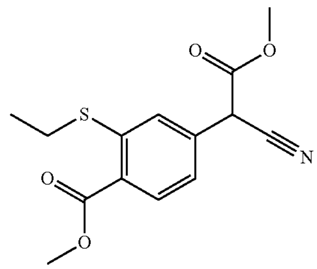 [SMILES: CCSc1cc(C(C#N)C(=O)OC)ccc1C(=O)OC] | | |
| XVI-4 | methyl 5-(1-cyano-2-ethoxy-2-oxo-ethyl)-3-ethylsulfonyl-pyridine-2-carboxylate | 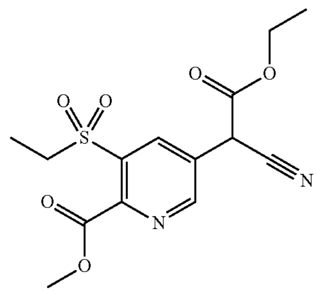 [SMILES: CCOC(=O)C(C#N)c1cnc(C(=O)OC)c(S(=O)(=O)CC)c1] | | LCMS (method 4): 341 (M + H)$^+$; retention time: 0.75 min |
| XIV-2 | methyl 4-(cyanomethyl)-2-ethylsulfanyl-benzoate | 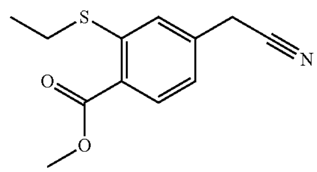 [SMILES: CCSc1cc(CC#N)ccc1C(=O)OC] | | LCMS (method 1): 236 (M + H)$^+$; retention time: 0.89 min |
| XIV-3 | methyl 5-(cyanomethyl)-3-ethylsulfonyl-pyridine-2-carboxylate | 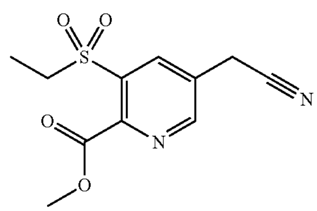 [SMILES: CCS(=O)(=O)c1cc(CC#N)cnc1C(=O)OC] | | LCMS (method 1): 269 (M + H)$^+$; retention time: 0.58 min |
| XII-1 | 5-(1-cyano-1-methyl-ethyl)-3-ethylsulfonyl-pyridine-2-carboxylic acid | 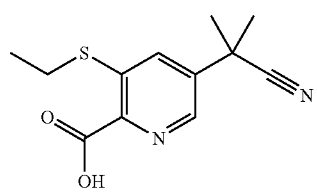 | | LCMS (method 1): 283 (M + H)$^+$; retention time: 0.42 min |
| XII-2 | 4-(1-cyano-1-methyl-ethyl)-2-ethylsulfanyl-benzoic acid | 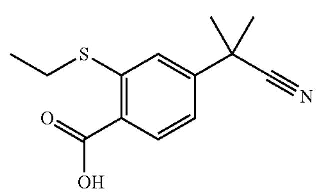 | | LCMS (method 1): 250 (M + H)$^+$; retention time: 0.85 min |
| XII-3 | 5-(1-cyano-1-methyl-ethyl)-3-ethylsulfonyl-pyridine-2-carboxylic acid | 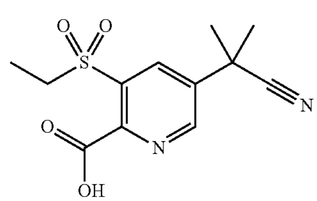 | | LCMS (method 1): 282 (M + H)$^+$; retention time: 0.42 min |

TABLE I1-continued

Examples of novel intermediate compounds of formula (XVI), (XIV), (XII), (XI), (XIII), (IX), and (II):

| Compound No. | IUPAC Name | Structure | Melting Point | MS/NMR |
|---|---|---|---|---|
| XI-1 | 5-(1-cyano-1-methyl-ethyl)-3-ethylsulfanyl-pyridine-2-carbonyl chloride | 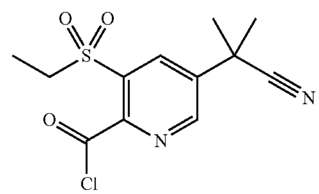 [SMILES: CCS(=O)(=O)c1cc(C(C)(C)C#N)cnc1C(=O)Cl] | | |
| XI-2 | 4-(1-cyano-1-methyl-ethyl)-2-ethylsulfanyl-benzoyl chloride | 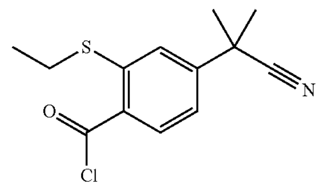 [SMILES: CCSc1cc(C(C)(C)C#N)ccc1C(=O)Cl] | | — |
| XI-3 | 5-(1-cyano-1-methyl-ethyl)-3-ethylsulfonyl-pyridine-2-carbonyl chloride | 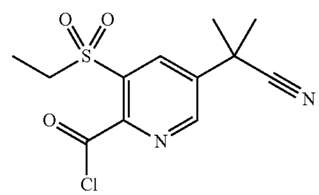 [SMILES: CCS(=O)(=O)c1cc(C(C)(C)C#N)cnc1C(=O)Cl] | | — |
| XIII-1 | methyl 5-(1-cyano-1-methyl-ethyl)-3-ethylsulfanyl-pyridine-2-carboxylate | 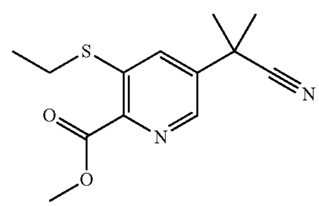 [SMILES: CCSc1cc(C(C)(C)C#N)cnc1C(=O)OC] | | LCMS (method 1): 265 (M + H)+; retention time: 0.86 min |
| XIII-2 | methyl 5-(1-cyano-1-methyl-ethyl)-3-ethylsulfonyl-pyridine-2-carboxylate | 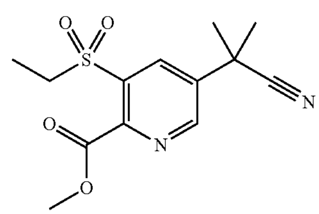 [SMILES: CCS(=O)(=O)c1cc(C(C)(C)C#N)cnc1C(=O)OC] | | LCMS (method 1): 297 (M + H)+; retention time: 0.77 min |
| XIII-3 | methyl 4-(1-cyano-1-methyl-ethyl)-2-ethylsulfanyl-benzoate | 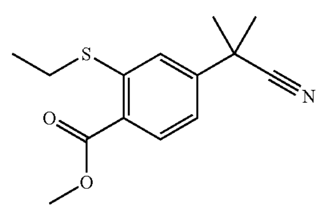 [SMILES: CCSc1cc(C(C)(C)C#N)ccc1C(=O)OC] | | LCMS (method 1): 264 (M + H)+; retention time: 1.01 min |
| IX-1 | N-[2-bromo-5-(methylamino)-4-pyridyl]-5-(1-cyano-1-methyl-ethyl)-3-ethylsulfanyl-pyridine-2-carboxamide | 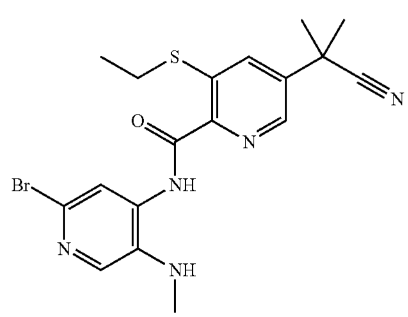 [SMILES: CCSc1cc(C(C)(C)C#N)cnc1C(=O)Nc1cc(Br)ncc1NC] | | LCMS (method 1): 434 (M + H)+; retention time: 0.82 min |

TABLE I1-continued

Examples of novel intermediate compounds of formula (XVI), (XIV), (XII), (XI), (XIII), (IX), and (II):

| Compound No. | IUPAC Name | Structure | Melting Point | MS/NMR |
|---|---|---|---|---|
| IX-2 | 5-(1-cyano-1-methyl-ethyl)-3-ethylsulfanyl-N-[5-(methylamino)-2-(trifluoromethyl)-4-pyridyl]pyridine-2-carboxamide | 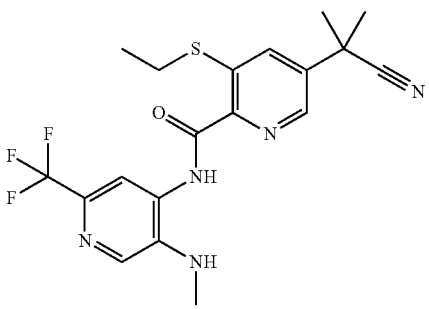 [SMILES: CCSc1cc(C(C)(C)C#N)cnc1C(=O)Nc1cc(C(F)(F)F)ncc1NC] | | LCMS (method 4): 424 (M + H)+; retention time: 0.85 min |
| IX-3 | 5-(1-cyano-1-methyl-ethyl)-3-ethylsulfanyl-N-[3-(methylamino)-6-(trifluoromethyl)pyridazin-4-yl]pyridine-2-carboxamide | 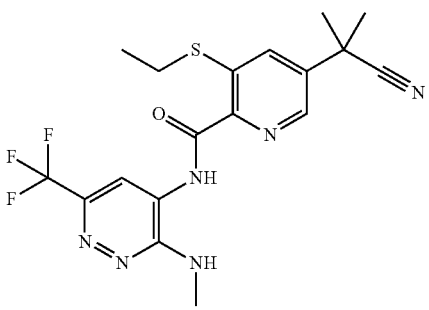 [SMILES: CCSc1cc(C(C)(C)C#N)cnc1C(=O)Nc1cc(C(F)(F)F)nnc1NC] | | LCMS (method 1): 425 (M + H)+; retention time: 1.03 min |
| IX-4 | 5-(1-cyano-1-methyl-ethyl)-3-ethylsulfonyl-N-[5-(methylamino)-2-(trifluoromethyl)-4-pyridyl]pyridine-2-carboxamide | 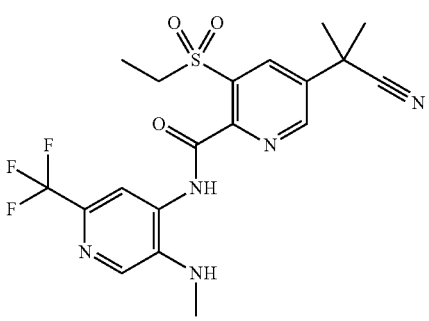 [SMILES: CCS(=O)(=O)c1cc(C(C)(C)C#N)cnc1C(=O)Nc1cc(C(F)(F)F)ncc1NC] | | LCMS (method 1): 456 (M + H)+; retention time: 0.85 min |
| IX-5 | 5-(1-cyano-1-methyl-ethyl)-3-ethylsulfonyl-N-[3-(methylamino)-6-(trifluoromethyl)pyridazin-4-yl]pyridine-2-carboxamide | 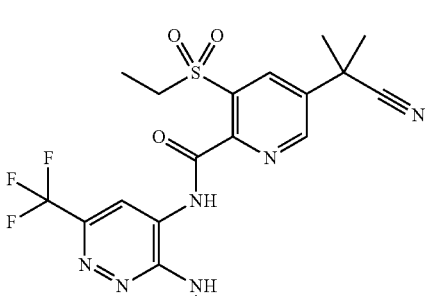 | | LCMS (method 1): 457 (M + H)+; retention time: 0.89 min |
| II-1 | 2-[5-ethylsulfanyl-6-[3-methyl-6-(trifluoromethyl)imidazo[4,5-c]pyridin-2-yl]-3-pyridyl]acetonitrile | 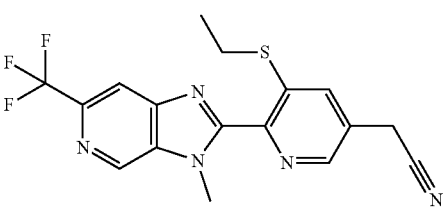 | | LCMS (method 1): 378 (M + H)+; retention time: 0.89 min |

TABLE I1-continued

Examples of novel intermediate compounds of formula (XVI), (XIV), (XII), (XI), (XIII), (IX), and (II):

| Compound No. | IUPAC Name | Structure | Melting Point | MS/NMR |
|---|---|---|---|---|
| II-2 | 2-[5-ethylsulfanyl-6-[7-methyl-3-(trifluoromethyl)imidazo-[4,5-c]pyridazin-6-yl]-3-pyridyl]acetonitrile | 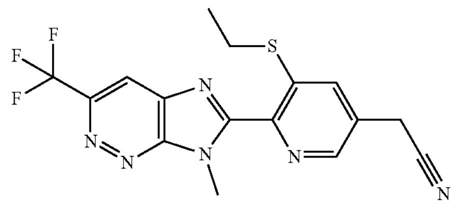 [SMILES: CCSc1cc(CC#N)cnc1-c1nc2cc(C(F)(F)F)nnc2n1C] | | LCMS (method 1): 379 (M + H)$^+$; retention time: 0.92 min |
| II-3 | 2-[3-ethylsulfanyl-4-[7-methyl-3-(trifluoromethyl)imidazo-[4,5-c]pyridazin-6-yl]phenyl]acetonitrile | 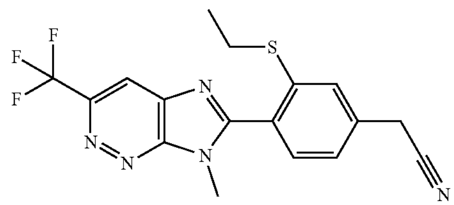 [SMILES: CCSc1cc(CC#N)ccc1-c1nc2cc(C(F)(F)F)nnc2n1C] | | LCMS (method 1): 378 (M + H)$^+$; retention time: 0.96 min |
| II-4 | 2-[3-ethylsulfanyl-4-[3-methyl-6-(trifluoromethyl)imidazo-[4,5-c]pyridin-2-yl]phenyl]acetonitrile | 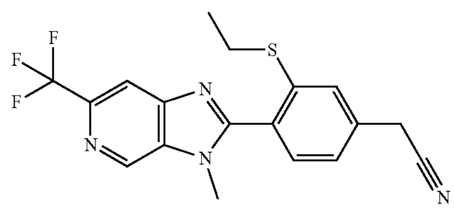 [SMILES: CCSc1cc(CC#N)ccc1-c1nc2cc(C(F)(F)F)ncc2n1C] | | LCMS (method 1): 377 (M + H)$^+$; retention time: 0.92 min |
| II-6 | 2-[5-ethylsulfonyl-6-[3-methyl-6-(trifluoromethyl)imidazo-[4,5-c]pyridin-2-yl]-3-pyridyl]acetonitrile | 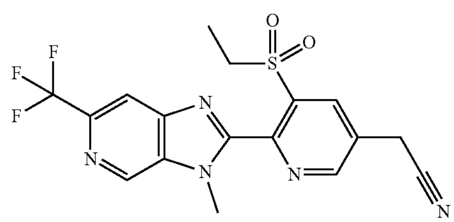 [SMILES: CCS(=O)(=O)c1cc(CC#N)cnc1-c1nc2cc(C(F)(F)F)ncc2n1C] | | LCMS (method 1): 410 (M + H)$^+$; retention time: 0.86 min |
| II-7 | 2-[5-ethylsulfonyl-6-[7-methyl-3-(trifluoromethyl)imidazo-[4,5-c]pyridazin-6-yl]-3-pyridyl]acetonitrile | 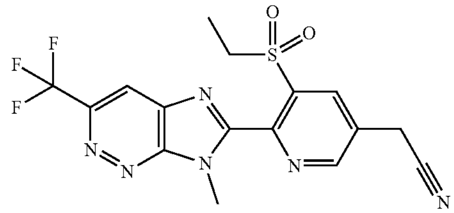 [SMILES: CCS(=O)(=O)c1cc(CC#N)cnc1-c1nc2cc(C(F)(F)F)nnc2n1C] | | LCMS (method 1): 411 (M + H)$^+$; retention time: 0.84 min |

The following mixtures of the compounds of formula I with active ingredients are preferred (the abbreviation "TX" means "one compound selected from the group consisting of the compounds described in Tables 1-4 of the present invention"):

an adjuvant selected from the group of substances consisting of petroleum oils (alternative name) (628)+TX, an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos (alternative name) [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate (alternative name)+TX, bromo-cyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben (alternative name)+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulfide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel (alternative name) [CCN]+TX, coumaphos (174)+TX, crotamiton (alternative name) [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulfon (1039)+TX, diafenthiuron (226)+TX, dialifos (1042)+TX, diazinon (227)+TX, dichlofluanid (230)+TX, dichlorvos (236)+TX, dicliphos (alternative name)+TX, dicofol (242)+TX, dicrotophos (243)+TX, dienochlor (1071)+TX, dimefox (1081)+TX, dimethoate (262)+TX, dinactin (alternative name) (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram (alternative name) [CCN]+TX, disulfoton (278)+TX, DNOC (282)+TX, dofenapyn (1113)+TX, doramectin (alternative name) [CCN]+TX, endosulfan (294)+TX, endothion (1121)+TX, EPN (297)+TX, eprinomectin (alternative name) [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad (alternative name)+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (alternative name) (473)+TX, isopropyl O-(methoxyaminothiophosphoryl)salicylate (IUPAC name) (473)+TX, ivermectin (alternative name) [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen (alternative name) [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime (alternative name) [CCN]+TX, mipafox (1293)+TX, monocrotophos (561)+TX, morphothion (1300)+TX, moxidectin (alternative name) [CCN]+TX, naled (567)+TX, NC-184 (compound code)+TX, NC-512 (compound code)+TX, nifluridide (1309)+TX, nikkomycins (alternative name) [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (alternative name) (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (alternative name) (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos (alternative name)+TX, selamectin (alternative name) [CCN]+TX, SI-0009 (compound code)+TX, sophamide (1402)+TX, spirodiclofen (738)+TX, spiromesifen (739)+TX, SSI-121 (development code) (1404)+TX, sulfiram (alternative name) [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam (alternative name)+TX, tetrachlorvinphos (777)+TX, tetradifon (786)+TX, tetranactin (alternative name) (653)+TX, tetrasul (1425)+TX, thiafenox (alternative name)+TX, thiocarboxime (1431)+TX, thiofanox (800)+TX, thiometon (801)+TX, thioquinox (1436)+TX, thuringiensin (alternative name) [CCN]+TX, triamiphos (1441)+TX, triarathene (1443)+TX, triazophos (820)+TX, triazuron (alternative name)+TX, trichlorfon (824)+TX, trifenofos (1455)+TX, trinactin (alternative name) (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX, a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa californica* NPV (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chrysoperla carnea* (alternative name) (151)+TX, *Cryptolaemus montrouzieri* (alternative name) (178)+TX, *Cydia pomonella* (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (alternative name) (575)+TX, *Orius* spp. (alternative name) (596)+TX, *Paecilomyces fumosoroseus* (alternative name) (613)+TX, *Phytoseiulus persimilis* (alternative name) (644)+TX, *Spodoptera exigua* multicapsid nuclear polyhedrosis virus (scientific name) (741)+TX, *Steinernema bibionis* (alternative name) (742)+TX, *Steinernema carpocapsae* (alternative name) (742)+TX, *Steinernema feltiae* (alternative name) (742)+TX, *Steinernema glaseri* (alternative name) (742)+TX, *Steinernema riobrave* (alternative name) (742)+TX, *Steinernema riobravis* (alternative name) (742)+TX, *Steinernema scapterisci* (alternative name) (742)+TX, *Steinernema* spp. (alternative name) (742)+TX, *Trichogramma* spp. (alternative name) (826)+TX, *Typhlodromus occidentalis* (alternative name) (844) and *Verticillium lecanii* (alternative name) (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexalure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure $B_1$ (alternative name) (839)+TX, trimedlure $B_2$ (alternative name) (839)+TX, trimedlure C (alternative name) (839) and trunc-call (alternative name) [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquinbutyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy)ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion (alternative name) [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin (alternative name) [CCN]+TX, allyxycarb (866)+TX, alpha-cypermethrin (202)+TX, alpha-ecdysone (alternative name) [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (alternative name) (41)+TX, azamethiphos (42)+TX, azinphos-ethyl (44)+TX, azinphos-methyl (45)+TX, azothoate (889)+TX, *Bacillus thuringiensis* delta endotoxins (alternative name) (52)+TX, barium hexafluorosilicate (alternative name) [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (alternative name) (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate (alternative name)+TX, bromfenvinfos (914)+TX, bromocyclen (918)+TX, bromo-DDT (alternative name) [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben (alternative name)+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (alternative name) (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin 11 (696)+TX, cinerins (696)+TX, cis-resmethrin (alternative name)+TX, cismethrin (80)+TX, clocythrin (alternative name)+TX, cloethocarb (999)+TX, closantel (alternative name) [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton (alternative name) [CCN]+TX, crotoxyphos (1010)+TX, crufomate (1011)+TX, cryolite (alternative name) (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate (alternative name) [CCN]+TX, d-limonene (alternative name) [CCN]+TX, d-tetramethrin (alternative name) (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos (alternative name)+TX, dicresyl (alternative name) [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor (alternative name) [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin (alternative name) [CCN]+TX, DSP (1115)+TX, ecdysterone (alternative name) [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin (alternative name) [CCN]+TX, esfenvalerate (302)+TX, etaphos (alternative name) [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (alternative name) (1056)+TX, ethylene dibromide (316)+TX, ethylene dichloride (chemical name)

(1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad (alternative name)+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (alternative name) (473)+TX, isodrin (1235)+TX, isofenphos (1236)+TX, isolane (1237)+TX, isoprocarb (472)+TX, isopropyl O-(methoxy-aminothiophosphoryl)salicylate (IUPAC name) (473)+TX, isoprothiolane (474)+TX, isothioate (1244)+TX, isoxathion (480)+TX, ivermectin (alternative name) [CCN]+TX, jasmolin I (696)+TX, jasmolin II (696)+TX, jodfenphos (1248)+TX, juvenile hormone I (alternative name) [CCN]+TX, juvenile hormone II (alternative name) [CCN]+TX, juvenile hormone III (alternative name) [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (alternative name) (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquin-butyl (1276)+TX, methothrin (alternative name) (533)+TX, methoxychlor (534)+TX, methoxyfenozide (535)+TX, methyl bromide (537)+TX, methyl isothiocyanate (543)+TX, methylchloroform (alternative name) [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime (alternative name) [CCN]+TX, mipafox (1293)+TX, mirex (1294)+TX, monocrotophos (561)+TX, morphothion (1300)+TX, moxidectin (alternative name) [CCN]+TX, naftalofos (alternative name) [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl 0-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemeton-methyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron (alternative name) [CCN]+TX, pentachlorophenol (623)+TX, pentachlorophenyl laurate (IUPAC name) (623)+TX, permethrin (626)+TX, petroleum oils (alternative name) (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I (alternative name) [CCN]+TX, precocene II (alternative name) [CCN]+TX, precocene Ill (alternative name) [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin I (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia (alternative name) [CCN]+TX, quinalphos (711)+TX, quinalphos-methyl (1376)+TX, quinothion (1380)+TX, quintiofos (1381)+TX, R-1492 (development code) (1382)+TX, rafoxanide (alternative name) [CCN]+TX, resmethrin (719)+TX, rotenone (722)+TX, RU 15525 (development code) (723)+TX, RU 25475 (development code) (1386)+TX, ryania (alternative name) (1387)+TX, ryanodine (traditional name) (1387)+TX, sabadilla (alternative name) (725)+TX, schradan (1389)+TX, sebufos (alternative name)+TX, selamectin (alternative name) [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+

TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (alternative name) (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam (alternative name)+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox (alternative name)+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin (alternative name) [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron (alternative name)+TX, trichlorfon (824)+TX, trichlormetaphos-3 (alternative name) [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (alternative name) (725)+TX, veratrine (alternative name) (725)+TX, XMC (853)+TX, xylylcarb (854)+TX, YI-5302 (compound code)+TX, zeta-cypermethrin (205)+TX, zetamethrin (alternative name)+TX, zinc phosphide (640)+TX, zolaprofos (1469) and ZXI 8901 (development code) (858)+TX, cyantraniliprole [736994-63-19+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, triflumezopyrim (disclosed in WO 2012/092115)+TX, fluxametamide (WO 2007/026965)+TX, epsilon-metofluthrin [240494-71-7]+TX, epsilon-momfluorothrin [1065124-65-3]+TX, fluazaindolizine [1254304-22-7]+TX, chloroprallethrin [399572-87-3]+TX, fluxametamide [928783-29-3]+TX, cyhalodiamide [1262605-53-7]+TX, tioxazafen [330459-31-9]+TX, broflanilide [1207727-04-5]+TX, flufiprole [704886-18-0]+TX, cyclaniliprole [1031756-98-5]+TX, tetraniliprole [1229654-66-3]+TX, guadipyr (described in WO2010/060231)+TX, cycloxaprid (described in WO 2005/077934)+TX, spiropidion+TX, Afidopyropen+TX, flupyrimin+TX, Momfluorothrin+TX, kappa-bifenthrin+TX, kappa-tefluthrin+TX, Dichloromezotiaz+TX, Tetrachloraniliprole+TX, benzpyrimoxan+TX;

a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (alternative name) (210)+TX, dazomet (216)+TX, DBCP (1045)+TX, DCIP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, *Myrothecium verrucaria* composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, fluensulfone [318290-98-1]+TX, fluopyram+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (alternative name) (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin (alternative name) [CCN] and ribavirin (alternative name) [CCN]+TX, a wound protectant selected from the group of substances consisting of mercuric oxide (512)+TX, octhilinone (590) and thiophanate-methyl (802)+TX, and biologically active compounds selected from the group consisting of azaconazole (60207-31-0]+TX, bitertanol [70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imibenconazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-30-7]+TX, meta-laxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3] [112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzo-lar-S-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-L190 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pyroquilon [57369-32-1]+TX, quinoxyfen [124495-18-7]+TX, quintozene [82-68-8]+TX, sulfur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, 3-difluoromethyl-1-methyl-1H-pyrazole-4-carboxylic acid (9-dichloromethylene-1,2,3,4-tetrahydro-1,4-methano-naphthalen-5-yl)-amide (disclosed in WO 2007/048556)+TX, 3-difluoromethyl-1-methyl-1H-pyrazole-4-carboxylic acid (3',4',5'-trifluoro-biphenyl-2-yl)-amide (disclosed in WO 2006/087343)+TX, [(3S,4R,4aR,6S,6aS,12R,12aS,12bS)-3-[(cyclopropylcarbonyl)oxy]-1,3,4,4a,5,6,6a,12,12a, 12b-decahydro-6,12-dihydroxy-4,6a,12b-trimethyl-11-oxo-9-(3-pyridinyl)-2H,11Hnaphtho[2,1-b]pyrano[3,4-e]pyran-4-yl] methyl-cyclopropanecarboxylate [915972-17-7]+TX and 1,3,5-trimethyl-N-(2-methyl-1-oxopropyl)-N-[3-(2-methyl-propyl)-4-[2,2,2-trifluoro-1-methoxy-1-(trifluoromethyl) ethyl]phenyl]-1H-pyrazole-4-carboxamide [926914-55-8]+TX; and microbials including: *Acinetobacter lwoffii*+TX, *Acremonium alternatum*+TX+TX, *Acremonium cephalosporium*+TX+TX, *Acremonium diospyri*+TX, *Acremonium obclavatum*+TX, *Adoxophyes orana* granulovirus (AdoxGV) (Capex®)+TX, *Agrobacterium radiobacter* strain K84 (Galltrol-A®)+TX, *Alternaria alternate*+TX, *Alternaria cassia*+TX, *Alternaria destruens* (Smolder®)+TX, *Ampelomyces quisqualis* (AQ10®)+TX, *Aspergillus flavus* AF36 (AF36®)+TX, *Aspergillus flavus* NRRL 21882 (Aflaguard®)+TX, *Aspergillus* spp.+TX, *Aureobasidium pullulans*+TX, *Azospirillum*+TX, (MicroAZ®+TX, TAZO B®)+TX, *Azotobacter*+TX, *Azotobacter chroocuccum* (Azotomeal®)+TX, *Azotobacter* cysts (Bionatural Blooming Blossoms®)+TX, *Bacillus amyloliquefaciens*+TX, *Bacillus cereus*+TX, *Bacillus chitinosporus* strain CM-1+TX, *Bacillus chitinosporus* strain AQ746+TX, *Bacillus licheniformis* strain HB-2 (Biostart™ Rhizoboost®)+TX, *Bacillus licheniformis* strain 3086 (EcoGuard®+TX, Green Releaf®)+TX, *Bacillus circulans*+TX, *Bacillus firmus* (BioSafe®+TX, BioNem-WP®+TX, VOTiVO®)+TX, *Bacillus firmus* strain 1-1582+TX, *Bacillus macerans*+TX, *Bacillus marismortui*+TX, *Bacillus megaterium*+TX, *Bacillus mycoides* strain AQ726+TX, *Bacillus papillae* (Milky Spore Powder®)+TX, *Bacillus pumilus* spp.+TX, *Bacillus pumilus* strain GB34 (Yield Shield®)+TX, *Bacillus pumilus* strain AQ717+TX, *Bacillus pumilus* strain QST 2808 (Sonata®+TX, Ballad Plus®)+TX, *Bacillus spahericus* (VectoLex®)+TX, *Bacillus* spp.+TX, *Bacillus* spp. strain AQ175+TX, *Bacillus* spp. strain AQ177+TX, *Bacillus* spp. strain AQ178+TX, *Bacillus subtilis* strain QST 713 (CEASE®+TX, Serenade®+TX, Rhapsody®)+TX, *Bacillus subtilis* strain QST 714 (JAZZ®)+TX, *Bacillus subtilis* strain AQ153+TX, *Bacillus subtilis* strain AQ743+TX, *Bacillus subtilis* strain QST3002+TX, *Bacillus subtilis* strain QST3004+TX, *Bacillus subtilis* var. *amyloliquefaciens* strain FZB24 (Taegro®+TX, Rhizopro®)+TX, *Bacillus thuringiensis* Cry 2Ae+TX, *Bacillus thuringiensis* Cry1Ab+TX, *Bacillus thuringiensis aizawai* GC 91 (Agree®)+TX, *Bacillus thuringiensis israelensis* (BMP123®+TX, Aquabac®+TX, VectoBac®)+TX, *Bacillus thuringiensis kurstaki* (Javelin®+TX, Deliver®+TX, CryMax®+TX, Bonide®+TX, Scutella WP®+TX, Turilav WP®+TX, Astuto®+TX, Dipel WP®+TX, Biobit®+TX, Foray®)+TX, *Bacillus thuringiensis kurstaki* BMP 123 (Baritone®)+TX, *Bacillus thuringiensis kurstaki* HD-1 (Bioprotec-CAF/3P®)+TX, *Bacillus thuringiensis* strain BD #32+TX, *Bacillus thuringiensis* strain AQ52+TX, *Bacillus thuringiensis* var. *aizawai* (XenTari®+TX, DiPel®)+TX, bacteria spp. (GROWMEND®+TX, GROWSWEET@+TX, Shootup®)+TX, bacteriophage of *Clavipacter michiganensis* (AgriPhage®)+TX, Bakflor®+TX, *Beauveria bassiana* (Beaugenic®+TX, Brocaril WP®)+TX, *Beauveria bassiana* GHA (Mycotrol ES®+TX, Mycotrol O®+TX, BotaniGuard®)+TX, *Beauveria brongniartii* (Engerlingspilz®+TX, Schweizer Beauveria®+TX, Melocont®)+TX, *Beauveria* spp.+TX, *Botrytis cineria*+TX, *Bradyrhizobium japonicum* (TerraMax®)+TX, *Brevibacillus brevis*+TX, *Bacillus thuringiensis tenebrionis* (Novodor®)+TX, BtBooster+TX, *Burkholderia cepacia* (Deny®+TX, Intercept®+TX, Blue Circle®)+TX, *Burkholderia gladii*+TX, *Burkholderia gladioli*+TX, *Burkholderia* spp.+TX, Canadian thistle fungus (CBH Canadian Bioherbicide®)+TX, *Candida butyri*+TX, *Candida famata*+TX, *Candida fructus*+TX, *Candida glabrata*+TX, *Candida guilliermondii*+TX, *Candida melibiosica*+TX, *Candida oleophila* strain O+TX, *Candida parapsilosis*+TX, *Candida pelliculosa*+TX, *Candida pulcherrima*+TX, *Candida reukaufii*+TX, *Candida saitoana* (Bio-Coat®+TX, Biocure®)+TX, *Candida sake*+TX, *Candida* spp.+TX, *Candida tenius*+TX, *Cedecea dravisae*+TX, *Cellulomonas flavigena*+TX, *Chaetomium cochliodes* (Nova-Cide®)+TX, *Chaetomium globosum* (Nova-Cide®)+TX, *Chromobacterium subtsugae* strain PRAA4-1T (Grandevo®)+TX, *Cladosporium cladosporioides*+TX, *Cladosporium oxysporum*+TX, *Cladosporium chlorocephalum*+TX, *Cladosporium* spp.+TX, *Cladosporium tenuissimum*+TX, *Clonostachys rosea* (EndoFine®)+TX, *Colletotrichum acutatum*+TX, *Coniothyrium minitans* (Cotans WG®)+TX, *Coniothyrium* spp.+TX, *Cryptococcus albidus* (YIELDPLUS®)+TX, *Cryptococcus humicola*+TX, *Cryptococcus infirmo-miniatus*+TX, *Cryptococcus laurentii*+TX, *Cryptophlebia leucotreta* granulovirus (Cryptex®)+TX, *Cupriavidus campinensis*+TX, *Cydia pomonella* granulovirus (CYD-X®)+TX, *Cydia pomonella* granulovirus (Madex®+TX, Madex Plus®+TX, Madex Max/Carpovirusine®)+TX, *Cylindrobasidium laeve* (Stumpout®)+TX, *Cylindrocladium*+TX, *Debaryomyces hansenii*+TX, *Drechslera hawaiinensis*+TX, *Enterobacter cloacae*+TX, *Enterobacteriaceae*+TX, *Entomophora virulenta* (Vektor®)+TX, *Epicoccum nigrum*+TX, *Epicoccum purpurascens*+TX, *Epicoccum* spp.+TX, *Filobasidium floriforme*+TX, *Fusarium acuminatum*+TX, *Fusarium chlamydosporum*+TX, *Fusarium oxysporum* (Fusaclean®/Biofox C®)+TX, *Fusarium proliferatum*+TX, *Fusarium* spp.+TX, *Galactomyces geotrichum*+TX, *Gliocladium catenulatum* (Primastop®+TX, Prestop®)+TX, *Gliocladium roseum*+TX, *Gliocladium* spp. (SoilGard®)+TX, *Gliocladium virens* (Soilgard®)+TX, Granulovirus (Granupom®)+TX, *Halobacillus halophilus*+TX, *Halobacillus litoralis*+TX, *Halobacillus trueperi*+TX, *Halomonas* spp.+TX, *Halomonas subglaciescola*+TX, *Halovibrio variabilis*+TX, *Hanseniaspora uvarum*+TX, *Helicoverpa armigera* nucleopolyhedrovirus (Helicovex®)+TX, *Helicoverpa zea* nuclear polyhedrosis virus (Gemstar®)+TX, Isoflavone-formononetin (Myconate®)+TX, *Kloeckera apiculata*+TX, *Kloeckera* spp.+TX, *Lagenidium giganteum* (Laginex®)+TX, *Lecanicillium longisporum* (Vertiblast®)+TX, *Lecanicillium muscarium* (Vertikil®)+TX, *Lymantria Dispar* nucleopolyhedrosis virus (Disparvirus®)+TX, *Marinococcus halophilus*+TX, *Meira geulakonigii*+TX, *Metarhizium anisopliae* (Met52®)+TX, *Metarhizium anisopliae* (Destruxin WP®)+TX, *Metschnikowia fruticola* (Shemer®)+TX, *Metschnikowia pulcherrima*+TX, *Microdochium dimerum* (Antibot®)+TX, *Micromonospora coerulea*+TX, *Microsphaeropsis ochracea*+TX, *Muscodor albus* 620 (Muscudor®)+TX, *Muscodor roseus* strain A3-5+TX, *Mycorrhizae* spp. (AMykor®+TX, Root Maximizer®)+TX, *Myrothecium verrucaria* strain AARC-0255 (DiTera®)+TX, BROS PLUS®+TX, *Ophiostoma piliferum* strain D97 (Sylvanex®)+TX, *Paecilomyces farinosus*+TX, *Paecilomyces fumosoroseus* (PFR-97®+TX, PreFeRal®)+TX, *Paecilomyces linacinus* (Biostat WP®)+TX, *Paecilomyces lilacinus* strain 251 (MeloCon WG®)+TX, *Paenibacillus polymyxa*+TX, *Pantoea agglomerans* (BlightBan C$_9$-1®)+TX, *Pantoea* spp.+TX,

*Pasteuria* spp. (Econem®)+TX, *Pasteuria nishizawae*+TX, *Penicillium aurantiogriseum*+TX, *Penicillium billai* (Jumpstart®+TX, TagTeam®)+TX, *Penicillium brevicompactum*+TX, *Penicillium frequentans*+TX, *Penicillium griseofulvum*+TX, *Penicillium purpurogenum*+TX, *Penicillium* spp.+TX, *Penicillium viridicatum*+TX, *Phlebiopsis gigantean* (Rotstop®)+TX, phosphate solubilizing bacteria (Phosphomeal®)+TX, *Phytophthora cryptogea*+TX, *Phytophthora palmivora* (Devine®)+TX, *Pichia anomala*+TX, *Pichia guilermondii*+TX, *Pichia membranaefaciens*+TX, *Pichia onychis*+TX, *Pichia stipites*+TX, *Pseudomonas aeruginosa*+TX, *Pseudomonas aureofasciens* (Spot-Less Biofungicide®)+TX, *Pseudomonas cepacia*+TX, *Pseudomonas chlororaphis* (AtEze®)+TX, *Pseudomonas corrugate*+TX, *Pseudomonas fluorescens* strain A506 (BlightBan A506®)+TX, *Pseudomonas putida*+TX, *Pseudomonas reactans*+TX, *Pseudomonas* spp.+TX, *Pseudomonas syringae* (Bio-Save®)+TX, *Pseudomonas viridiflava*+TX, *Pseudomons fluorescens* (Zequanox®)+TX, *Pseudozyma flocculosa* strain PF-A22 UL (Sporodex L®)+TX, *Puccinia canaliculata*+TX, *Puccinia thlaspeos* (Wood Warrior®)+TX, *Pythium paroecandrum*+TX, *Pythium oligandrum* (Polygandron®+TX, Polyversum®)+TX, *Pythium periplocum*+TX, *Rhanella aquatilis*+TX, *Rhanella* spp.+TX, *Rhizobia* (Dormal®+TX, Vault®)+TX, *Rhizoctonia*+TX, *Rhodococcus globerulus* strain AQ719+TX, *Rhodosporidium diobovatum*+TX, *Rhodosporidium toruloides*+TX, *Rhodotorula* spp.+TX, *Rhodotorula glutinis*+TX, *Rhodotorula graminis*+TX, *Rhodotorula mucilagnosa*+TX, *Rhodotorula rubra*+TX, *Saccharomyces cerevisiae*+TX, *Salinococcus roseus*+TX, *Sclerotinia minor*+TX, *Sclerotinia minor* (SARRITOR®)+TX, *Scytalidium* spp.+TX, *Scytalidium uredinicola*+TX, *Spodoptera exigua nuclear polyhedrosis virus* (Spod-X®+TX, Spexit®)+TX, *Serratia marcescens*+TX, *Serratia plymuthica*+TX, *Serratia* spp.+TX, *Sordaria fimicola*+TX, *Spodoptera littoralis nucleopolyhedrovirus* (Littovir®)+TX, *Sporobolomyces roseus*+TX, *Stenotrophomonas maltophilia*+TX, *Streptomyces ahygroscopicus*+TX, *Streptomyces albaduncus*+TX, *Streptomyces exfoliates*+TX, *Streptomyces galbus*+TX, *Streptomyces griseoplanus*+TX, *Streptomyces griseoviridis* (Mycostop®)+TX, *Streptomyces lydicus* (Actinovate®)+TX, *Streptomyces lydicus* WYEC-108 (ActinoGrow®)+TX, *Streptomyces violaceus*+TX, *Tilletiopsis minor*+TX, *Tilletiopsis* spp.+TX, *Trichoderma asperellum* (T34 Biocontrol®)+TX, *Trichoderma gamsii* (Tenet®)+TX, *Trichoderma atroviride* (Plantmate®)+TX, *Trichoderma hamatum* TH 382+TX, *Trichoderma harzianum rifai* (Mycostar®)+TX, *Trichoderma harzianum* T-22 (Trianum-P®+TX, PlantShield HC®+TX, RootShield®+TX, Trianum-G®)+TX, *Trichoderma harzianum* T-39 (Trichodex®)+TX, *Trichoderma inhamatum*+TX, *Trichoderma koningii*+TX, *Trichoderma* spp. LC 52 (Sentinel®)+TX, *Trichoderma lignorum*+TX, *Trichoderma longibrachiatum*+TX, *Trichoderma polysporum* (Binab T®)+TX, *Trichoderma taxi*+TX, *Trichoderma virens*+TX, *Trichoderma virens* (formerly *Gliocladium virens* GL-21) (SoilGuard®)+TX, *Trichoderma viride*+TX, *Trichoderma viride* strain ICC 080 (Remedier®)+TX, *Trichosporon pullulans*+TX, *Trichosporon* spp.+TX, *Trichothecium* spp.+TX, *Trichothecium roseum*+TX, *Typhula phacorrhiza* strain 94670+TX, *Typhula phacorrhiza* strain 94671+TX, *Ulocladium atrum*+TX, *Ulocladium oudemansii* (Botry-Zen®)+TX, *Ustilago maydis*+TX, various bacteria and supplementary micronutrients (Natural II®)+TX, various fungi (Millennium Microbes®)+TX, *Verticillium chlamydosporium*+TX, *Verticillium lecanii* (Mycotal®+TX, Vertalec®)+TX, Vip3Aa20 (VIPtera®)+TX, *Virgibacillus marismortui*+TX, *Xanthomonas campestris* pv. *Poae* (Camperico®)+TX, *Xenorhabdus bovienii*+TX, *Xenorhabdus nematophilus*; and Plant extracts including: pine oil (Retenol®)+TX, azadirachtin (Plasma Neem Oil®+TX, AzaGuard®+TX, MeemAzal®+TX, Molt-X®+TX, Botanical IGR (Neemazad®+TX, Neemix®)+TX, canola oil (Lilly Miller Vegol®)+TX, *Chenopodium ambrosioides* near *ambrosioides* (Requiem®)+TX, *Chrysanthemum* extract (Crisant®)+TX, extract of neem oil (Trilogy®)+TX, essentials oils of *Labiatae* (Botania®)+TX, extracts of clove rosemary peppermint and thyme oil (Garden insect killer®)+TX, *Glycinebetaine* (Greenstim®)+TX, garlic+TX, lemongrass oil (GreenMatch®)+TX, neem oil+TX, *Nepeta cataria* (Catnip oil)+TX, Nepeta catarina+TX, nicotine+TX, oregano oil (MossBuster®)+TX, *Pedaliaceae* oil (Nematon®)+TX, pyrethrum+TX, *Quillaja saponaria* (NemaC$_{20}$)+TX, *Reynoutria sachalinensis* (Regalia®+TX, Sakalia®)+TX, rotenone (Eco Roten®)+TX, *Rutaceae* plant extract (Soleo®)+TX, soybean oil (Ortho ecosense®)+TX, tea tree oil (Timorex Gold®)+TX, thymus oil+TX, AGNIQUE® MMF+TX, BugOil®+TX, mixture of rosemary sesame pepermint thyme and cinnamon extracts (EF 300®)+TX, mixture of clove rosemary and peppermint extract (EF 400®)+TX, mixture of clove pepermint garlic oil and mint (Soil Shot®)+TX, kaolin (Screen®)+TX, storage glucam of brown algae (Laminarin®); and pheromones including: blackheaded fireworm pheromone (3M Sprayable Blackheaded Fireworm Pheromone®)+TX, Codling Moth Pheromone (Paramount dispenser-(CM)/Isomate C-Plus®)+TX, Grape Berry Moth Pheromone (3M MEC-GBM Sprayable Pheromone®)+TX, Leafroller pheromone (3M MEC—LR Sprayable Pheromone®)+TX, Muscamone (Snip7 Fly Bait®+TX, Starbar Premium Fly Bait®)+TX, Oriental Fruit Moth Pheromone (3M oriental fruit moth sprayable pheromone®)+TX, Peachtree Borer Pheromone (Isomate-P®)+TX, Tomato Pinworm Pheromone (3M Sprayable pheromone®)+TX, Entostat powder (extract from palm tree) (Exosex CM®)+TX, (E+TX,Z+TX, Z)-3+TX,8+TX,11 Tetradecatrienyl acetate+TX, (Z+TX,Z+TX,E)-7+TX,11+TX,13-Hexadecatrienal+TX, (E+TX,Z)-7+TX,9-Dodecadien-1-yl acetate+TX, 2-Methyl-1-butanol+TX, Calcium acetate+TX, Scenturion®+TX, Biolure®+TX, Check-Mate®+TX, Lavandulyl senecioate; and Macrobials including: *Aphelinus abdominalis*+TX, *Aphidius ervi* (Aphelinus-System®)+TX, *Acerophagus papaya*+TX, *Adalia bipunctata* (Adalia-System®)+TX, *Adalia bipunctata* (Adaline®)+TX, *Adalia bipunctata* (Aphidalia®)+TX, *Ageniaspis citricola*+TX, *Ageniaspis fuscicollis*+TX, *Amblyseius andersoni* (Anderline®+TX, Andersoni-System®)+TX, *Amblyseius califomicus* (Amblyline®+TX, Spical®)+TX, *Amblyseius cucumeris* (Thripex®+TX, Bugline cucumeris®)+TX, *Amblyseius fallacis* (Fallacis®)+TX, *Amblyseius swirskii* (Bugline swirskii®+TX, Swirskii-Mite®)+TX, *Amblyseius womersleyi* (WomerMite®)+TX, *Amitus hesperidum*+TX, *Anagrus atomus*+TX, *Anagyrus fusciventris*+TX, *Anagyrus kamali*+TX, *Anagyrus loecki*+TX, *Anagyrus pseudococci* (Citripar®)+TX, *Anicetus benefices*+TX, *Anisopteromalus calandrae*+TX, *Anthocoris nemoralis* (Anthocoris-System®)+TX, *Aphelinus abdominalis* (Apheline®+TX, Aphiline®)+TX, *Aphelinus asychis*+TX, *Aphidius colemani* (Aphipar®)+TX, *Aphidius ervi* (Ervipar®)+TX, *Aphidius gifuensis*+TX, *Aphidius matricariae* (Aphipar-M®)+TX, *Aphidoletes aphidimyza* (Aphidend®)+TX, *Aphidoletes aphidimyza* (Aphidoline®)+TX, *Aphytis lingnanensis*+TX, *Aphytis melinus*+TX, *Aprostocetus hagenowii*+TX, *Atheta coriaria*

(Staphyline®)+TX, *Bombus* spp.+TX, *Bombus terrestris* (Natupol Beehive®)+TX, *Bombus terrestris* (Beeline®+TX, Tripol®)+TX, *Cephalonomia stephanoderis*+TX, *Chilocorus nigritus*+TX, *Chrysoperla carnea* (Chrysoline®)+TX, *Chrysoperla carnea* (Chrysopa®)+TX, *Chrysoperla rufilabris*+TX, *Cirrospilus ingenuus*+TX, *Cirrospilus quadristriatus*+TX, *Citrostichus phyllocnistoides*+TX, *Closterocerus chamaeleon*+TX, *Closterocerus* spp.+TX, *Coccidoxenoides perminutus* (Planopar®)+TX, *Coccophagus cowperi*+TX, *Coccophagus lycimnia*+TX, *Cotesia flavipes*+TX, *Cotesia plutellae*+TX, *Cryptolaemus montrouzieri* (Cryptobug®+TX, Cryptoline®)+TX, *Cybocephalus nipponicus*+TX, *Dacnusa sibirica*+TX, *Dacnusa sibirica* (Minusa®)+TX, *Diglyphus isaea* (Diminex®)+TX, *Delphastus catalinae* (Delphastus®)+TX, *Delphastus pusillus*+TX, *Diachasmimorpha krausii*+TX, *Diachasmimorpha longicaudata*+TX, *Diaparsis jucunda*+TX, *Diaphorencyrtus aligarhensis*+TX, *Diglyphus isaea*+TX, *Diglyphus isaea* (Miglyphus®+TX, Digline®)+TX, *Dacnusa sibirica* (Dac-Digline®+TX, Minex®)+TX, *Diversinervus* spp.+TX, *Encarsia citrina*+TX, *Encarsia formosa* (Encarsia max®+TX, Encarline®+TX, En-Strip®)+TX, *Eretmocerus eremicus* (Enermix®)+TX, *Encarsia guadeloupae*+TX, *Encarsia haitiensis*+TX, *Episyrphus balteatus* (Syrphidend®)+TX, *Eretmoceris siphonini*+TX, *Eretmocerus californicus*+TX, *Eretmocerus eremicus* (Ercal®+TX, Eretline e®)+TX, *Eretmocerus eremicus* (Bemimix®)+TX, *Eretmocerus hayati*+TX, *Eretmocerus mundus* (Bemipar®+TX, Eretline m®)+TX, *Eretmocerus siphonini*+TX, *Exochomus quadripustulatus*+TX, *Feltiella acarisuga* (Spidend®)+TX, *Feltiella acarisuga* (Feltiline®)+TX, *Fopius arisanus*+TX, *Fopius ceratitivorus*+TX, Formononetin (Wirless Beehome®)+TX, *Franklinothrips vespiformis* (Vespop®)+TX, *Galendromus occidentalis*+TX, *Goniozus legneri*+TX, *Habrobracon hebetor*+TX, *Harmonia axyridis* (Harmo-Beetle®)+TX, *Heterorhabditis* spp. (Lawn Patrol®)+TX, *Heterorhabditis bacteriophora* (NemaShield HB®+TX, Nemaseek®+TX, Terranem-Nam®+TX, Terranem®+TX, Larvanem®+TX, B-Green®+TX, NemAttack®+TX, Nematop®)+TX, *Heterorhabditis megidis* (Nemasys H®+TX, BioNem H®+TX, Exhibitline hm®+TX, Larvanem-M®)+TX, *Hippodamia convergens*+TX, *Hypoaspis aculeifer* (Aculeifer-System®+TX, Entomite-A®)+TX, *Hypoaspis miles* (Hypoline m®+TX, Entomite-M®)+TX, *Lbalia leucospoides*+TX, *Lecanoideus floccissimus*+TX, *Lemophagus errabundus*+TX, *Leptomastidea abnormis*+TX, *Leptomastix dactylopfi* (Leptopar®)+TX, *Leptomastix epona*+TX, *Lindorus lophanthae*+TX, *Lipolexis oregmae*+TX, *Lucilia caesar* (Natufly®)+TX, *Lysiphlebus testaceipes*+TX, *Macrolophus caliginosus* (Mirical-N®+TX, Macroline c®+TX, Mirical®)+TX, *Mesoseiulus longipes*+TX, *Metaphycus flavus*+TX, *Metaphycus lounsburyi*+TX, *Micromus angulatus* (Milacewing®)+TX, *Microterys flavus*+TX, *Muscidifurax raptorellus* and *Spalangia cameroni* (Biopar®)+TX, *Neodryinus typhlocybae*+TX, *Neoseiulus californicus*+TX, *Neoseiulus cucumeris* (THRYPEX®))+TX, *Neoseiulus fallacis*+TX, *Nesideocoris tenuis* (Nesidio-Bug®+TX, Nesibug®)+TX, *Ophyra aenescens* (Biofly®)+TX, *Orius insidiosus* (Thripor-I®+TX, Oriline i®)+TX, *Orius laevigatus* (Thripor-L®+TX, Oriline I®)+TX, *Orius majusculus* (Oriline m®)+TX, *Orius strigicollis* (Thripor-S®)+TX, *Pauesia juniperorum*+TX, *Pediobius foveolatus*+TX, *Phasmarhabditis hermaphrodita* (Nemaslug®)+TX, *Phymastichus coffea*+TX, *Phytoseiulus macropilus*+TX, *Phytoseiulus persimilis* (Spidex®+TX, Phytoline p®)+TX, *Podisus maculiventris* (Podisus®)+TX, *Pseudacteon curvatus*+TX, *Pseudacteon obtusus*+TX, *Pseudacteon tricuspis*+TX, *Pseudaphycus maculipennis*+TX, *Pseudleptomastix mexicana*+TX, *Psyllaephagus pilosus*+TX, *Psyttalia concolor* (complex)+TX, *Quadrastichus* spp.+TX, *Rhyzobius lophanthae*+TX, *Rodolia cardinalis*+TX, *Rumina decollate*+TX, *Semielacher petiolatus*+TX, *Sitobion avenae* (Ervibank®)+TX, *Steinernema carpocapsae* (Nematac C®+TX, Millenium®+TX, BioNem C®+TX, NemAttack®+TX, Nemastar®+TX, Capsanem®)+TX, *Steinernema feltiae* (NemaShield®+TX, Nemasys F®+TX, BioNem F®+TX, Steinernema-System®+TX, NemAttack®+TX, Nemaplus®+TX, Exhibitline sf®+TX, Scia-rid®+TX, Entonem®)+TX, *Steinernema kraussei* (Nemasys L®+TX, BioNem L®+TX, Exhibitline srb®)+TX, *Steinernema riobrave* (BioVector®+TX, BioVektor®)+TX, *Steinernema scapterisci* (Nematac S®)+TX, *Steinernema* spp.+TX, *Steinernematid* spp. (Guardian Nematodes®)+TX, *Stethorus punctillum* (Stethorus®)+TX, *Tamarixia radiate*+TX, *Tetrastichus setifer*+TX, *Thripobius semiluteus*+TX, *Torymus sinensis*+TX, *Trichogramma brassicae* (Tricholine b®)+TX, *Trichogramma brassicae* (Tricho-Strip®)+TX, *Trichogramma evanescens*+TX, *Trichogramma minutum*+TX, *Trichogramma ostriniae*+TX, *Trichogramma platneri*+TX, *Trichogramma pretiosum*+TX, *Xanthopimpla stemmator*; and other biologicals including: abscisic acid+TX, bioSea®+TX, *Chondrostereum purpureum* (Chontrol Paste®)+TX, *Colletotrichum gloeosporioides* (Callego®)+TX, Copper Octanoate (Cueva®)+TX, Delta traps (Trapline d®)+TX, *Erwinia amylovora* (Harpin) (ProAct®+TX, Ni-HIBIT Gold CST®)+TX, Ferri-phosphate (Ferramol®)+TX, Funnel traps (Trapline y®)+TX, Gallex®+TX, Grower's Secret®+TX, Homo-brassonolide+TX, Iron Phosphate (Lilly Miller Worry Free Ferramol Slug & Snail Bait®)+TX, MCP hail trap (Trapline f®)+TX, *Microctonus hyperodae*+TX, *Mycoleptodiscus terrestris* (Des-X®)+TX, BioGain®+TX, Aminomite®+TX, Zenox®+TX, Pheromone trap (Thripline ams®)+TX, potassium bicarbonate (MilStop®)+TX, potassium salts of fatty acids (Sanova®)+TX, potassium silicate solution (Sil-Matrix®)+TX, potassium iodide+potassium-thiocyanate (Enzicur®)+TX, SuffOil-X®+TX, Spider venom+TX, *Nosema locustae* (Semaspore Organic Grasshopper Control®)+TX, Sticky traps (Trapline YF®+TX, Rebell Amarillo®)+TX and Traps (Takitrapline y+b®)+TX;

or a biologically active compound or agent selected from: Brofluthrinate+TX, Diflovidazine+TX, Flometoquin+TX, Fluhexafon+TX, *Plutella xylostella* Granulosis virus+TX, *Cydia pomonella* Granulosis virus+TX, Imicyafos+TX, *Heliothis virescens* Nucleopolyhedrovirus+TX, *Heliothis punctigera* Nucleopolyhedrovirus+TX, *Helicoverpa zea* Nucleopolyhedrovirus+TX, *Spodoptera frugiperda* Nucleopolyhedrovirus+TX, *Plutella xylostella* Nucleopolyhedrovirus+TX, p-cymene+TX, Pyflubumide+TX, Pyrafluprole+TX, QRD 420+TX, QRD 452+TX, QRD 460+TX, Terpenoid blends+TX, Terpenoids+TX, Tetraniliprole+TX, and α-terpinene+TX; or an active substance referenced by a code+TX, such as code AE 1887196 (BSC-BX60309)+TX, code NNI-0745 GR+TX, code IKI-3106+TX, code JT-L001+TX, code ZNQ-08056+TX, code IPPA152201+TX, code HNPC-A9908 (CAS: [660411-21-2])+TX, code HNPC-A2005 (CAS: [860028-12-2])+TX, code JS118+TX, code ZJ0967+TX, code ZJ2242+TX, code JS7119 (CAS: [929545-74-4])+TX, code SN-1172+TX, code HNPC-A9835+TX, code HNPC-A9955+TX, code HNPC-A3061+TX, code Chuanhua 89-1+TX, code IPP-10+TX, code ZJ3265+TX, code JS9117+TX, code ZJ3757+TX, code ZJ4042+TX, code ZJ4014+TX, code ITM-121+TX, code DPX-RAB55 (DKI-2301)+TX, code NA-89+TX, code MIE-1209+TX, code MCI-8007+TX, code BCS-CL73507+TX, code S-1871+TX, code DPX-RDS63+TX, and code AKD-1193+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The active ingredient mixture of the compounds of formula I selected from Tables 1-4 with active ingredients described above comprises a compound selected from Tables 1-4 and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula I selected from Tables 1-4 and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from Tables 1-4 and the active ingredients as described above is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compounds of the invention and compositions thereof are also be suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound of formula I. The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula (I). Further, it is hereby made available, a composition comprising a plant propagation material treated with a compound of formula (I).

Seed treatment comprises all suitable seed treatment techniques known in the art, such as seed dressing, seed coating, seed dusting, seed soaking and seed pelleting. The seed treatment application of the compound formula (I) can be carried out by any known methods, such as spraying or by dusting the seeds before sowing or during the sowing/planting of the seeds.

BIOLOGICAL EXAMPLES

The Examples which follow serve to illustrate the invention. Certain compounds of the invention can be distinguished from known compounds by virtue of greater efficacy at low application rates, which can be verified by the person skilled in the art using the experimental procedures outlined in the Examples, using lower application rates if necessary, for example 50 ppm, 25 ppm, 12.5 ppm, 6 ppm, 3 ppm, 1.5 ppm, 0.8 ppm, 0.2 ppm or 0.05 ppm.

Example B1: *Spodoptera Littoralis* (Egyptian Cotton Leaf Worm)

Cotton leaf discs were placed onto agar in 24-well microtiter plates and sprayed with aqueous test solutions prepared from 10'000 ppm DMSO stock solutions. After drying the leaf discs were infested with five L1 larvae. The samples were assessed for mortality, anti-feeding effect, and growth inhibition in comparison to untreated samples 3 days after infestation. Control of *Spodoptera littoralis* by a test sample is given when at least one of the categories mortality, anti-feedant effect, and growth inhibition is higher than the untreated sample.

The following compounds resulted in at least 80% control at an application rate of 200 ppm: P2, P5.

Example B2: *Spodoptera Littoralis* (Egyptian Cotton Leaf Worm)

Test compounds were applied by pipette from 10'000 ppm DMSO stock solutions into 24-well plates and mixed with agar. Lettuce seeds were placed onto the agar and the multi well plate was closed by another plate which contained also agar. After 7 days the compound was absorbed by the roots and the lettuce grew into the lid plate. The lettuce leaves were then cut off into the lid plate. *Spodoptera* eggs were pipetted through a plastic stencil onto a humid gel blotting paper and the lid plate was closed with it. The samples were assessed for mortality, anti-feedant effect and growth inhibition in comparison to untreated samples 6 days after infestation.

The following compounds gave an effect of at least 80% in at least one of the three categories (mortality, anti-feeding, or growth inhibition) at a test rate of 12.5 ppm: P2.

Example B3: *Plutella Xylostella* (Diamond Back Moth)

24-well microtiter plates with artificial diet were treated with aqueous test solutions prepared from 10'000 ppm DMSO stock solutions by pipetting. After drying, the plates were infested with L2 larvae (10 to 15 per well). The samples were assessed for mortality and growth inhibition in comparison to untreated samples 5 days after infestation.

The following compounds gave an effect of at least 80% in at least one of the two categories (mortality or growth inhibition) at an application rate of 200 ppm: P2, P3, P4, P5, P9, P10, P12 and P17.

Example B4: *Diabrotica Balteata* (Corn Root Worm)

Maize sprouts placed onto an agar layer in 24-well microtiter plates were treated with aqueous test solutions prepared from 10'000 ppm DMSO stock solutions by spraying. After drying, the plates were infested with L2 larvae (6 to 10 per well). The samples were assessed for mortality and growth inhibition in comparison to untreated samples 4 days after infestation.

The following compounds gave an effect of at least 80% in at least one of the two categories (mortality or growth inhibition) at an application rate of 200 ppm: P2, P3, P4, P5, P6, P10, P11, P12, P15, P16 and P17.

Example B5: *Myzus Persicae* (Green Peach Aphid)

Sunflower leaf discs were placed onto agar in a 24-well microtiter plate and sprayed with aqueous test solutions prepared from 10'000 ppm DMSO stock solutions. After drying, the leaf discs were infested with an aphid population of mixed ages. The samples were assessed for mortality 6 days after infestation.

The following compounds resulted in at least 80% mortality at an application rate of 200 ppm: P2, P4, P5, P10, P12, P15 and P17.

Example B6: *Myzus Persicae* (Green Peach Aphid)

Roots of pea seedlings infested with an aphid population of mixed ages were placed directly into aqueous test solutions prepared from 10'000 DMSO stock solutions. The samples were assessed for mortality 6 days after placing seedlings into test solutions.

The following compounds resulted in at least 80% mortality at a test rate of 24 ppm: P2, P5, P6, P10, P12, P15, P17 and P19.

Example B7: Bemisia Tabaci (Cotton White Fly)

Cotton leaf discs were placed on agar in 24-well microtiter plates and sprayed with aqueous test solutions prepared from 10'000 ppm DMSO stock solutions. After drying the leaf discs were infested with adult white flies. The samples were checked for mortality 6 days after incubation.

The following compounds resulted in at least 80% mortality at an application rate of 200 ppm: P2, P5, P11, P12 and P17.

Example B8: Euschistus Heros (Neotropical Brown Stink Bug)

Soybean leaves on agar in 24-well microtiter plates were sprayed with aqueous test solutions prepared from 10'000 ppm DMSO stock solutions. After drying the leaves were infested with N2 nymphs. The samples were assessed for mortality and growth inhibition in comparison to untreated samples 5 days after infestation.

The following compounds gave an effect of at least 80% in at least one of the two categories (mortality or growth inhibition) at an application rate of 200 ppm: P2, P5, P6, P9, P11, P12, P13, P15, P16, P17 and P19.

Example B10: *Tetranychus Urticae* (Two-Spotted Spider Mite)

Bean leaf discs on agar in 24-well microtiter plates were sprayed with aqueous test solutions prepared from 10'000 ppm DMSO stock solutions. After drying the leaf discs were infested with a mite population of mixed ages. The samples were assessed for mortality on mixed population (mobile stages) 8 days after infestation.

Example B11: *Thrips Tabaci* (Onion *Thrips*)

Sunflower leaf discs were placed on agar in 24-well microtiter plates and sprayed with aqueous test solutions prepared from 10'000 ppm DMSO stock solutions. After drying the leaf discs were infested with a *thrips* population of mixed ages. The samples were assessed for mortality 6 days after infestation.

Example B12: *Frankliniella Occidentalis* (Western Flower *Thrips*)

Sunflower leaf discs were placed on agar in 24-well microtiter plates and sprayed with aqueous test solutions prepared from 10'000 DMSO stock solutions. After drying the leaf discs were infested with a Frankliniella population of mixed ages. The samples were assessed for mortality 7 days after infestation.

Example B13: Comparison of the Insecticidal Activity of Compound P17 According to the Invention with the Structurally Most Closely Comparable Compound from the State of the Art Activity of compound P17 according to the present invention and of compound P15 from WO2016/026848 against Euschistus heros is summarized in Table B13.

TABLE B13

| Compound | Concentration (ppm) | Insect | Mortality (%) |
|---|---|---|---|
| Compound No. P15, known from WO2016/026848 | 3 | Euschistus heros | 65 |
| (state of the art) | | | |
| Compound No. P17 | 3 | Euschistus heros | 95 |
| (present invention) | | | |

Test Description:

2 week old soybean plants were sprayed with diluted aqueous test solutions. Afterwards plants were infested with 10 stink bug nymphs (N2). Soybean seeds were added as additional food source to the test system. 5 days after treatment the samples were assessed for mortality.

What is claimed is:
1. A compound of formula I,

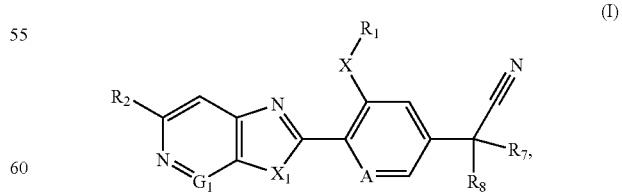

wherein
A is CH or N;
X is S, SO or $SO_2$;
$R_1$ is $C_1$-$C_4$alkyl, $C_1$-$C_4$haloalkyl or $C_3$-$C_6$cycloalkyl-$C_1$-$C_4$alkyl;

99

$G_1$ is N or CH;

$X_1$ is O, S or $NR_3$; wherein $R_3$ is hydrogen or $C_1$-$C_4$alkyl;

$R_2$ is halogen, $C_1$-$C_6$haloalkyl, $C_1$-$C_4$haloalkylsulfanyl, $C_1$-$C_4$haloalkylsulfinyl, $C_1$-$C_4$haloalkylsulfonyl or $C_1$-$C_6$haloalkoxy;

$R_7$ is hydrogen, halogen, cyano, $C_1$-$C_6$alkyl, $C_1$-$C_6$haloalkyl, $C_3$-$C_6$cycloalkyl, $C_1$-$C_4$alkoxy, $C_1$-$C_4$alkoxy-$C_1$-$C_4$alkyl, $C_1$-$C_4$alkylsulfanyl, $C_1$-$C_4$alkylsulfanyl-$C_1$-$C_4$alkyl, $C_1$-$C_4$alkylsulfinyl-$C_1$-$C_4$alkyl, $C_1$-$C_4$alkylsulfonyl-$C_1$-$C_4$alkyl or $C_1$-$C_4$alkyloxycarbonyl; and $R_8$ is chlorine, bromine, iodine, cyano, $C_1$-$C_6$alkyl, $C_1$-$C_6$haloalkyl, $C_3$-$C_6$cycloalkyl, $C_1$-$C_4$alkoxy, $C_1$-$C_4$alkoxy-$C_1$-$C_4$alkyl, $C_1$-$C_4$alkylsulfanyl, $C_1$-$C_4$alkylsulfanyl-$C_1$-$C_4$alkyl, $C_1$-$C_4$alkylsulfinyl-$C_1$-$C_4$alkyl, $C_1$-$C_4$alkylsulfonyl-$C_1$-$C_4$alkyl or $C_1$-$C_4$alkyloxycarbonyl; and agrochemically acceptable salts, stereoisomers, enantiomers, tautomers and N-oxides of the compounds of formula I.

2. The compound, or an agrochemically acceptable salt, stereoisomer, enantiomer, tautomer or N-oxide thereof, according to claim 1 wherein $R_1$ is $C_1$-$C_4$alkyl or $C_3$-$C_6$cycloalkyl-$C_1$-$C_4$alkyl.

3. The compound, or an agrochemically acceptable salt, stereoisomer, enantiomer, tautomer or N-oxide thereof, according to claim 1 wherein $R_2$ is halogen, $C_1$-$C_4$haloalkyl, $C_1$-$C_4$haloalkylsulfanyl, $C_1$-$C_4$haloalkylsulfinyl or $C_1$-$C_4$haloalkylsulfonyl.

4. The compound, or an agrochemically acceptable salt, stereoisomer, enantiomer, tautomer or N-oxide thereof, according to claim 1 wherein $R_7$ is hydrogen, fluoro, cyano, $C_1$-$C_4$alkoxycarbonyl, $C_1$-$C_4$alkyl.

5. The compound, or an agrochemically acceptable salt, stereoisomer, enantiomer, tautomer or N-oxide thereof, according to claim 1 wherein $R_8$ is cyano or $C_1$-$C_4$alkyl.

6. The compound, or an agrochemically acceptable salt, stereoisomer, enantiomer, tautomer or N-oxide thereof, according to claim 1 wherein $X_1$ is $NR_3$, wherein $R_3$ is $C_1$-$C_4$alkyl.

7. The compound, or an agrochemically acceptable salt, stereoisomer, enantiomer, tautomer or N-oxide thereof, according to claim 1 wherein X is S or $SO_2$.

8. The compound, or an agrochemically acceptable salt, stereoisomer, enantiomer, tautomer or N-oxide thereof, according to claim 1 wherein $R_1$ is $C_1$-$C_4$alkyl or cyclopropylmethyl and $R_2$ is halogen or $C_1$-$C_3$haloalkyl.

9. The compound, or an agrochemically acceptable salt, stereoisomer, enantiomer, tautomer or N-oxide thereof, according to claim 1 wherein $R_7$ is hydrogen methyl, ethyl or fluoro and $R_8$ is methyl or ethyl.

10. The compound, or an agrochemically acceptable salt, stereoisomer, enantiomer, tautomer or N-oxide thereof, according to claim 1 wherein A is CH or N;

X is S or $SO_2$;

$G_1$ is N or CH;

$X_1$ is $NCH_3$;

$R_1$ is methyl, ethyl, n-propyl, i-propyl or cyclopropylmethyl;

$R_2$ is $C_1$-$C_2$haloalkyl;

$R_7$ is methyl; and $R_8$ is methyl or ethyl.

11. A compound, or an agrochemically acceptable salt, stereoisomer, enantiomer, tautomer or N-oxide thereof, of formula I,

100

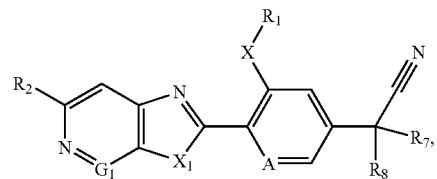

wherein A is N;

X is S, SO or $SO_2$;

$R_1$ is $C_1$-$C_4$alkyl, $C_1$-$C_4$haloalkyl or $C_3$-$C_6$cycloalkyl-$C_1$-$C_4$alkyl;

$G_1$ is N or CH;

$X_1$ is O, S or $NR_3$; wherein $R_3$ is hydrogen or $C_1$-$C_4$alkyl;

$R_2$ is halogen, $C_1$-$C_6$haloalkyl, $C_1$-$C_4$haloalkylsulfanyl, $C_1$-$C_4$haloalkylsulfinyl, $C_1$-$C_4$haloalkylsulfonyl or $C_1$-$C_6$haloalkoxy;

$R_7$ is hydrogen, halogen, cyano, $C_1$-$C_6$alkyl, $C_1$-$C_6$haloalkyl, $C_3$-$C_6$cycloalkyl, $C_1$-$C_4$alkoxy, $C_1$-$C_4$alkoxy-$C_1$-$C_4$alkyl, $C_1$-$C_4$alkylsulfanyl, $C_1$-$C_4$alkylsulfanyl-$C_1$-$C_4$alkyl, $C_1$-$C_4$alkylsulfinyl-$C_1$-$C_4$alkyl, $C_1$-$C_4$alkylsulfonyl-$C_1$-$C_4$alkyl or $C_1$-$C_4$alkyloxycarbonyl; and $R_8$ is halogen, cyano, $C_1$-$C_6$alkyl, $C_1$-$C_6$haloalkyl, $C_3$-$C_6$cycloalkyl, $C_1$-$C_4$alkoxy, $C_1$-$C_4$alkoxy-$C_1$-$C_4$alkyl, $C_1$-$C_4$alkylsulfanyl, $C_1$-$C_4$alkylsulfanyl-$C_1$-$C_4$alkyl, $C_1$-$C_4$alkylsulfinyl-$C_1$-$C_4$alkyl, $C_1$-$C_4$alkylsulfonyl-$C_1$-$C_4$alkyl or $C_1$-$C_4$alkyloxycarbonyl.

12. A compound of formula IX,

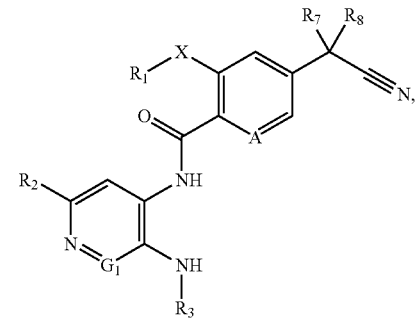

wherein

A is CH or N;

X is S, SO or $SO_2$;

$R_1$ is $C_1$-$C_4$alkyl;

$G_1$ is N or CH;

$R_3$ is hydrogen or $C_1$-$C_4$alkyl;

$R_2$ is halogen, $C_1$-$C_6$haloalkyl, $C_1$-$C_4$haloalkylsulfanyl, $C_1$-$C_4$haloalkylsulfinyl, $C_1$-$C_4$haloalkylsulfonyl or $C_1$-$C_6$haloalkoxy;

$R_7$ is hydrogen, halogen, cyano, $C_1$-$C_6$alkyl, $C_1$-$C_6$haloalkyl, $C_3$-$C_6$cycloalkyl, $C_1$-$C_4$alkoxy, $C_1$-$C_4$alkoxy$C_1$-$C_4$alkyl, $C_1$-$C_4$alkylsulfanyl, $C_1$-$C_4$alkylsulfanyl-$C_1$-$C_4$alkyl, $C_1$-$C_4$alkylsulfinyl-$C_1$-$C_4$alkyl, $C_1$-$C_4$alkylsulfonyl-$C_1$-$C_4$alkyl or $C_1$-$C_4$alkyloxycarbonyl; and $R_8$ is halogen, cyano, $C_1$-$C_6$alkyl, $C_1$-$C_6$haloalkyl, $C_3$-$C_6$cycloalkyl, $C_1$-$C_4$alkoxy, $C_1$-$C_4$alkoxy-$C_1$-

$C_4$alkyl, $C_1$-$C_4$alkylsulfanyl, $C_1$-$C_4$alkylsulfanyl-$C_1$-$C_4$alkyl, $C_1$-$C_4$alkylsulfinyl-$C_1$-$C_4$alkyl, $C_1$-$C_4$alkylsulfonyl-$C_1$-$C_4$alkyl or $C_1$-$C_4$alkyloxycarbonyl; or a regioisomer thereof, or an isomeric mixture thereof; or a compound of formula XI,

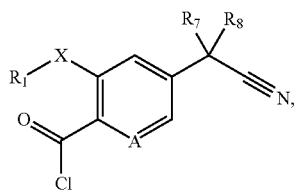

(XI)

wherein

A is CH or N;

X is S, SO or $SO_2$;

$R_1$ is $C_1$-$C_4$alkyl;

$R_7$ is hydrogen, halogen, cyano, $C_1$-$C_6$alkyl, $C_1$-$C_6$haloalkyl, $C_3$-$C_6$cycloalkyl, $C_1$-$C_4$alkoxy, $C_1$-$C_4$alkoxy-$C_1$-$C_4$alkyl, $C_1$-$C_4$alkylsulfanyl, $C_1$-$C_4$alkylsulfanyl-$C_1$-$C_4$alkyl, $C_1$-$C_4$alkylsulfinyl-$C_1$-$C_4$alkyl, $C_1$-$C_4$alkylsulfonyl-$C_1$-$C_4$alkyl or $C_1$-$C_4$alkyloxycarbonyl; and $R_8$ is halogen, cyano, $C_1$-$C_6$alkyl, $C_1$-$C_6$haloalkyl, $C_3$-$C_6$cycloalkyl, $C_1$-$C_4$alkoxy, $C_1$-$C_4$alkoxy-$C_1$-$C_4$alkyl, $C_1$-$C_4$alkylsulfanyl, $C_1$-$C_4$alkylsulfanyl-$C_1$-$C_4$alkyl, $C_1$-$C_4$alkylsulfinyl-$C_1$-$C_4$alkyl, $C_1$-$C_4$alkylsulfonyl-$C_1$-$C_4$alkyl or $C_1$-$C_4$alkyloxycarbonyl; or a compound of formula XII,

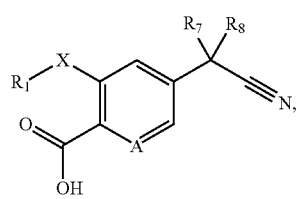

(XII)

wherein

A is CH or N;

X is S, SO or $SO_2$;

$R_1$ is $C_1$-$C_4$alkyl;

$R_7$ is hydrogen, halogen, cyano, $C_1$-$C_6$alkyl, $C_1$-$C_6$haloalkyl, $C_3$-$C_6$cycloalkyl, $C_1$-$C_4$alkoxy, $C_1$-$C_4$alkoxy-$C_1$-$C_4$alkyl, $C_1$-$C_4$alkylsulfanyl, $C_1$-$C_4$alkylsulfanyl-$C_1$-$C_4$alkyl, $C_1$-$C_4$alkylsulfinyl-$C_1$-$C_4$alkyl, $C_1$-$C_4$alkylsulfonyl-$C_1$-$C_4$alkyl or $C_1$-$C_4$alkyloxycarbonyl; and $R_8$ is halogen, cyano, $C_1$-$C_6$alkyl, $C_1$-$C_6$haloalkyl, $C_3$-$C_6$cycloalkyl, $C_1$-$C_4$alkoxy, $C_1$-$C_4$alkoxy-$C_1$-$C_4$alkyl, $C_1$-$C_4$alkylsulfanyl, $C_1$-$C_4$alkylsulfanyl-$C_1$-$C_4$alkyl, $C_1$-$C_4$alkylsulfinyl-$C_1$-$C_4$alkyl, $C_1$-$C_4$alkylsulfonyl-$C_1$-$C_4$alkyl or $C_1$-$C_4$alkyloxycarbonyl; or a compound of formula XIII,

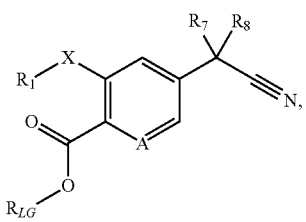

(XIII)

wherein

A is CH or N;

X is S, SO or $SO_2$;

$R_1$ is $C_1$-$C_4$alkyl;

$R_7$ is hydrogen, halogen, cyano, $C_1$-$C_6$alkyl, $C_1$-$C_6$haloalkyl, $C_3$-$C_6$cycloalkyl, $C_1$-$C_4$alkoxy, $C_1$-$C_4$alkoxy-$C_1$-$C_4$alkyl, $C_1$-$C_4$alkylsulfanyl, $C_1$-$C_4$alkylsulfanyl-$C_1$-$C_4$alkyl, $C_1$-$C_4$alkylsulfinyl-$C_1$-$C_4$alkyl, $C_1$-$C_4$alkylsulfonyl-$C_1$-$C_4$alkyl or $C_1$-$C_4$alkyloxycarbonyl; and $R_8$ is halogen, cyano, $C_1$-$C_6$alkyl, $C_1$-$C_6$haloalkyl, $C_3$-$C_6$cycloalkyl, $C_1$-$C_4$alkoxy, $C_1$-$C_4$alkoxy-$C_1$-$C_4$alkyl, $C_1$-$C_4$alkylsulfanyl, $C_1$-$C_4$alkylsulfanyl-$C_1$-$C_4$alkyl, $C_1$-$C_4$alkylsulfinyl-$C_1$-$C_4$alkyl, $C_1$-$C_4$alkylsulfonyl-$C_1$-$C_4$alkyl or $C_1$-$C_4$alkyloxycarbonyl; and $R_{LG}$ is $C_1$-$C_4$alkyl and wherein the compound is not

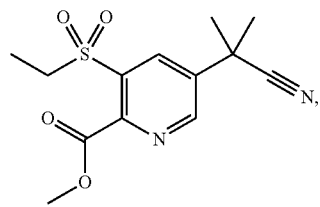 [SMILES: CCS(=O)(=O)c1cc(C(C)(C)C#N)cnc1C(=O)OC]

or a compound of formula XVI,

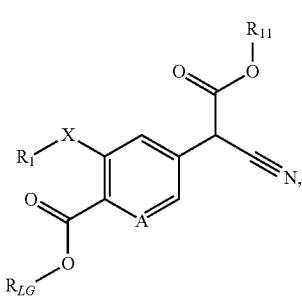

(XVI)

wherein

A is CH or N;

X is S, SO or $SO_2$;

$R_1$ is $C_1$-$C_4$alkyl;

$R_{11}$ is $C_1$-$C_4$alkyl; and $R_{LG}$ is $C_1$-$C_4$alkyl.

13. The compound of claim 12, wherein the compound is the compound of formula IX.

14. The compound of claim 13, wherein
A is N;
X is S or $SO_2$;
$R_1$ is ethyl;
$R_3$ is methyl;
$R_2$ is $CF_3$;
$R_7$ is methyl of fluoro; and
$R_8$ is methyl or fluoro.

15. The compound of claim 12, wherein the compound is the compound of formula XI.

16. The compound of claim 15, wherein
A is N;
X is S or $SO_2$;
$R_1$ is ethyl;
$R_7$ is methyl of fluoro; and
$R_8$ is methyl or fluoro.

17. The compound of claim 12, wherein the compound is the compound of formula XVI.

18. The compound of claim 17, wherein
A is N;
X is S or $SO_2$;
$R_1$ is ethyl;
$R_7$ is methyl of fluoro; and
$R_8$ is methyl or fluoro.

19. The compound of claim 12, wherein the compound is the compound of formula XIII.

20. The compound of claim 19, wherein
A is N;
X is S or $SO_2$;
$R_1$ is ethyl;
$R_7$ is methyl of fluoro;
$R_8$ is methyl or fluoro; and
$R_{LG}$ is methyl or ethyl.

21. The compound of claim 12, wherein the compound is the compound of formula XIII.

22. The compound of claim 21, wherein
A is N;
X is S or $SO_2$;
$R_1$ is ethyl;
$R_{11}$ is methyl or ethyl; and
$R_{LG}$ is methyl or ethyl.

23. A compound of formula I, wherein
A is CH or N;
X is S, SO or $SO_2$;
$R_1$ is $C_1$-$C_4$alkyl, $C_1$-$C_4$haloalkyl or $C_3$-$C_6$cycloalkyl-$C_1$-$C_4$alkyl;
$G_1$ is N or CH;
$X_1$ is O, S or $NR_3$; wherein $R_3$ is hydrogen or $C_1$-$C_4$alkyl;
$R_2$ is halogen, $C_1$-$C_6$haloalkyl, $C_1$-$C_4$haloalkylsulfanyl, $C_1$-$C_4$haloalkylsulfinyl, $C_1$-$C_4$haloalkylsulfonyl or $C_1$-$C_6$haloalkoxy;
$R_7$ is halogen, cyano, $C_1$-$C_6$alkyl, $C_1$-$C_6$haloalkyl, $C_3$-$C_6$cycloalkyl, $C_1$-$C_4$alkoxy, $C_1$-$C_4$alkoxy-$C_1$-$C_4$alkyl, $C_1$-$C_4$alkylsulfanyl, $C_1$-$C_4$alkylsulfanyl-$C_1$-$C_4$alkyl, $C_1$-$C_4$alkylsulfinyl-$C_1$-$C_4$alkyl, $C_1$-$C_4$alkylsulfonyl-$C_1$-$C_4$alkyl or $C_1$-$C_4$alkyloxycarbonyl; and
$R_8$ is halogen, cyano, $C_1$-$C_6$alkyl, $C_1$-$C_6$haloalkyl, $C_3$-$C_6$cycloalkyl, $C_1$-$C_4$alkoxy, $C_1$-$C_4$alkoxy-$C_1$-$C_4$alkyl, $C_1$-$C_4$alkylsulfanyl, $C_1$-$C_4$alkylsulfanyl-$C_1$-$C_4$alkyl, $C_1$-$C_4$alkylsulfinyl-$C_1$-$C_4$alkyl, $C_1$-$C_4$alkylsulfonyl-$C_1$-$C_4$alkyl or $C_1$-$C_4$alkyloxycarbonyl;

and agrochemically acceptable salts, stereoisomers, enantiomers, tautomers and N-oxides of the compounds of formula I.

24. A composition comprising an insecticidally, acaricidally, nematicidally or molluscicidally effective amount of the compound of formula (I), or an agrochemically acceptable salt, stereoisomer, enantiomer, tautomer or N-oxide thereof, as defined in claim 23 and, optionally, an auxiliary or diluent.

25. A method of combating and controlling insects, acarines, nematodes or molluscs which comprises applying to a pest, to a locus of the pest, or to a plant susceptible to attack by the pest an insecticidally, acaricidally, nematicidally or molluscicidally effective amount of the compound of formula (I), or an agrochemically acceptable salt, stereoisomer, enantiomer, tautomer or N-oxide thereof, as defined in claim 23.

26. A method for the protection of plant propagation material from the attack by insects, acarines, nematodes or molluscs, which comprises treating the propagation material or the site, where the propagation material is planted, with the composition according to claim 24.

27. The compound, or an agrochemically acceptable salt, stereoisomer, enantiomer, tautomer or N-oxide thereof, according to claim 23 wherein
A is CH or N;
X is S or $SO_2$;
$G_1$ is N or CH;
$X_1$ is $NCH_3$;
$R_1$ is methyl, ethyl, n-propyl, i-propyl or cyclopropylmethyl;
$R_2$ is $C_1$-$C_2$haloalkyl;
$R_7$ is methyl or fluoro; and
$R_8$ is fluoro, methyl or ethyl.

28. A compound selected from
2-[5-ethylsulfonyl-6-[3-methyl-6-(trifluoromethyl)imidazo[4,5-c]pyridin-2-yl]-3-pyridyl]-2-methyl-propanedinitrile;
2-[5-ethylsulfonyl-6-[7-methyl-3-(trifluoromethyl)imidazo[4,5-c]pyridazin-6-yl]-3-pyridyl]-2-methyl-propanenitrile;
2-ethyl-2-[5-ethylsulfonyl-6-[3-methyl-6-(trifluoromethyl)imidazo[4,5-c]pyridin-2-yl]-3-pyridyl]butanenitrile;
2-[5-ethylsulfonyl-6-[3-methyl-6-(trifluoromethyl)imidazo[4,5-c]pyridin-2-yl]-3-pyridyl]butanenitrile;
2-[5-ethylsulfonyl-6-[3-methyl-6-(trifluoromethyl)imidazo[4,5-c]pyridin-2-yl]-3-pyridyl]-2-methyl-propanenitrile;
2-[5-ethylsulfonyl-6-[3-methyl-6-(trifluoromethyl)imidazo[4,5-c]pyridin-2-yl]-3-pyridyl]propanenitrile;
2-[5-ethylsulfanyl-6-[3-methyl-6-(trifluoromethyl)imidazo[4,5-c]pyridin-2-yl]-3-pyridyl]propanedinitrile;
2-[5-ethylsulfanyl-6-[3-methyl-6-(trifluoromethyl)imidazo[4,5-c]pyridin-2-yl]-3-pyridyl]-2-methyl-propanedinitrile;
ethyl 2-cyano-2-[5-ethylsulfonyl-6-[3-methyl-6-(trifluoromethyl)imidazo[4,5-c]pyridin-2-yl]-3-pyridyl]propanoate;

2-[5-ethylsulfonyl-6-[3-methyl-6-(trifluoromethyl)imidazo[4,5-c]pyridin-2-yl]-3-pyridyl]-3-methyl-butanenitrile;

2-[3-ethylsulfanyl-4-[7-methyl-3-(trifluoromethyl)imidazo[4,5-c]pyridazin-6-yl]phenyl]-2-methyl-propanenitrile;

2-[3-ethylsulfonyl-4-[7-methyl-3-(trifluoromethyl)imidazo[4,5-c]pyridazin-6-yl]phenyl]-2-methyl-propanenitrile;

2-[3-ethylsulfanyl-4-[7-methyl-3-(trifluoromethyl)imidazo[4,5-c]pyridazin-6-yl]phenyl]propanenitrile;

2-[3-ethylsulfonyl-4-[7-methyl-3-(trifluoromethyl)imidazo[4,5-c]pyridazin-6-yl]phenyl]propanenitrile;

2-[5-ethylsulfonyl-6-[3-methyl-6-(trifluoromethyl)imidazo[4,5-c]pyridin-2-yl]-3-pyridyl]-2,2-difluoro-acetonitrile;

2-[3-ethylsulfanyl-4-[3-methyl-6-(trifluoromethyl)imidazo[4,5-c]pyridin-2-yl]phenyl]-2-methyl-propanenitrile;

2-[3-ethylsulfonyl-4-[3-methyl-6-(trifluoromethyl)imidazo[4,5-c]pyridin-2-yl]phenyl]-2-methyl-propanenitrile;

2-[5-ethylsulfonyl-6-[3-methyl-6-(trifluoromethyl)imidazo[4,5-c]pyridin-2-yl]-3-pyridyl]-2-fluoro-propanenitrile;

2-[6-(6-bromo-3-methyl-imidazo[4,5-c]pyridin-2-yl)-5-ethylsulfonyl-3-pyridyl]-2-methyl-propanenitrile;

2-[5-ethylsulfonyl-6-[3-methyl-6-(1,1,2,2,2-pentafluoroethyl)imidazo[4,5-c]pyridin-2-yl]-3-pyridyl]-2-methyl-propanenitrile;

ethyl 2-cyano-2-[5-ethylsulfanyl-6-[3-methyl-6-(trifluoromethyl)imidazo[4,5-c]pyridin-2-yl]-3-pyridyl]propanoate;

2-[5-ethylsulfonyl-6-(6-iodo-3-methyl-imidazo[4,5-c]pyridin-2-yl)-3-pyridyl]-2-methyl-propanenitrile;

2-[6-(6-bromo-3-methyl-imidazo[4,5-c]pyridin-2-yl)-5-ethylsulfanyl-3-pyridyl]-2-methyl-propanenitrile;

2-[5-ethylsulfanyl-6-[3-methyl-6-(trifluoromethyl)imidazo[4,5-c]pyridin-2-yl]-3-pyridyl]-2-methyl-propanenitrile;

ethyl 2-cyano-2-[5-ethylsulfonyl-6-[3-methyl-6-(trifluoromethyl)imidazo[4,5-c]pyridin-2-yl]-3-pyridyl]acetate; and 2-[5-ethylsulfanyl-6-[7-methyl-3-(trifluoromethyl)imidazo[4,5-c]pyridazin-6-yl]-3-pyridyl]-2-methyl-propanenitrile.

\* \* \* \* \*